US012404517B2

(12) United States Patent
Ma et al.

(10) Patent No.: US 12,404,517 B2
(45) Date of Patent: Sep. 2, 2025

(54) RHIZOBIAL tRNA-DERIVED SMALL RNAs AND USES THEREOF FOR REGULATING PLANT NODULATION

(71) Applicant: Purdue Research Foundation, West Lafayette, IN (US)

(72) Inventors: Jianxin Ma, West Lafayette, IN (US); Bo Ren, Beijing (CN); Jingbo Duan, West Lafayette, IN (US); Xutong Wang, West Lafayete, IN (US)

(73) Assignee: Purdue Research Foundation, West Lafayette, IN (US)

( * ) Notice: Subject to any disclaimer, the term of this patent is extended or adjusted under 35 U.S.C. 154(b) by 387 days.

(21) Appl. No.: 17/611,802

(22) PCT Filed: May 18, 2020

(86) PCT No.: PCT/US2020/033464
§ 371 (c)(1),
(2) Date: Nov. 16, 2021

(87) PCT Pub. No.: WO2020/232448
PCT Pub. Date: Nov. 19, 2020

(65) Prior Publication Data
US 2022/0251589 A1  Aug. 11, 2022

Related U.S. Application Data

(60) Provisional application No. 62/848,672, filed on May 16, 2019.

(51) Int. Cl.
*C12N 15/82* (2006.01)
(52) U.S. Cl.
CPC ..... *C12N 15/8262* (2013.01); *C12N 15/8218* (2013.01)

(58) Field of Classification Search
None
See application file for complete search history.

(56) References Cited

U.S. PATENT DOCUMENTS

2013/0267429 A1  10/2013  Gardner et al.
2014/0141044 A1  5/2014  Bhatt et al.

FOREIGN PATENT DOCUMENTS

CN  101490266 A  7/2009
WO  2018107103 A1  6/2018

OTHER PUBLICATIONS

Bandillo et al. "Dissecting the Genetic Basis of Local Adaptation in Soybean" 2017 Scientific Reports 7:17195 DOI:10.1038/s41598-017-17342-w (12 total pages). (Year: 2017).*

(Continued)

*Primary Examiner* — Matthew R Keogh
*Assistant Examiner* — Rebecca Stephens
(74) *Attorney, Agent, or Firm* — Reichel Stohry Dean LLP; Natalie J. Dean

(57) ABSTRACT

Rhizobial infection is the key process for initiating symbiotic nitrogen-fixing root nodules in legumes, which requires specific recognition of signal molecules produced by the bacteria and their hosts. Here, it is established that rhizobial tRNA-derived small RNA fragments (tRFs) are crucial signal molecules modulating host nodulation, which uncovers a bacterial small RNA-mediated mechanism for prokaryote-eukaryote interaction. Transgenic plants are also provided that express a construct encoding rhizobial-derived tRNA, which is subsequently cleaved to produce artificial tRFs. Constructs and methods of producing the same are also provided, as well as modifications for repressing a mechanism for the negative regulation of nodulation present within plants.

10 Claims, 29 Drawing Sheets
Specification includes a Sequence Listing.

(56) References Cited

OTHER PUBLICATIONS

Wang et al. "Symbiosis specificity in the legume—rhizobial mutualism" 2012 Cellular Microbiology 14(3):334-342. (Year: 2012).*

Tian et al. "Comparative genomics of rhizobia nodulating soybean suggests extensive recruitment of lineage-specific genes in adaptations" 2012 PNAS 109(22):8629-8634. (Year: 2012).*

Ren et al. "Rhizobial tRNA-derived small RNAs are signal molecules regulating plant nodulation" 2019 Science 365:919-922 (Year: 2019).*

Smith et al. ("Nodulation of Glycine max by Six *Bradyrhizobium japonicum* Strains with Different Competitive Abilities" 1989 App. & Env. Microbio. 55(8):1957-1962). (Year: 1989).*

Wang et al. "MicroRNA167-Directed Regulation of the Auxin Response Factors GmARF8a and GmARF8b Is Required for Soybean Nodulation and Lateral Root Development" 2015 Plant Physiology 168:101-116. (Year: 2015).*

Zhou et al. "A Robust and Rapid Candidate Gene Mapping Pipeline Based on M2 Populations" 2021 Frontiers in Plant Sci. 12: 681816 doi: 10.3389/fpls.2021.681816. (Year: 2021).*

International Searching Authority, International Search Report, PCT Application No. PCT/US2020/033464, dated Sep. 11, 2020, US.

International Searching Authority, Written Opinion of the International Searching Authority, PCT Application No. PCT/US2020/033464, dated Sep. 11, 2020, US.

Wang et al., MicroRNA167-Directed Regulation of the Auxin Response Factors GmARF8a and GmARF8b is Required for Soybean Nodulation and Lateral Root Development, Plant Physiology, Jul. 2015, 168: 101-116, American Society of Plant Biologists, US.

Madhugiri et al., Small RNAs of the Bradyrhizobium/Rhodopseudomonas Lineage and Their Analysis, RNA Biology, Jan. 2012, 9(1): 47-58, Taylor & Francis, UK.

Borges and Martienssen, The Expanding World of Small RNAs in Plants, National Review of Molecular Cellular Biology, Dec. 2015, 16(12) 727-741, US.

Jin et al., Computational Investigation of Small RNAs in the Establishment of Root Nodules and Arbuscular Mycorrhiza in Leguminous Plants, Science China Life Sciences, Jun. 2018, 61(6): 706-717, Springer/Science China Press, CN.

Yuen et al., Loss-of-Function Mutations of Root Hair Defective3 Suppress Root Waving, Skewing, and Epidermal Cell File Rotation in *Arabidopsis*, Plant Physiology, Jun. 2005, 138: 701-714, American Society of Plant Biologists, US.

Ren et al., Rhizobial tRNA-Derived Small RNAs are Signal Molecules Regulating Plant Modulation, Science, Aug. 30, 2019, 365(6456): 919-922, American Association for the Advancement of Science, US.

Ledermann et al., Stable Fluorescent and Enzyamatic Tagging of Bradyrhizobium diazoefficiens to Analyze Host-Plant Infection and Colonization, Molecular Plant-Microbe Interactions 28(9): 959-967 (2015), US.

* cited by examiner

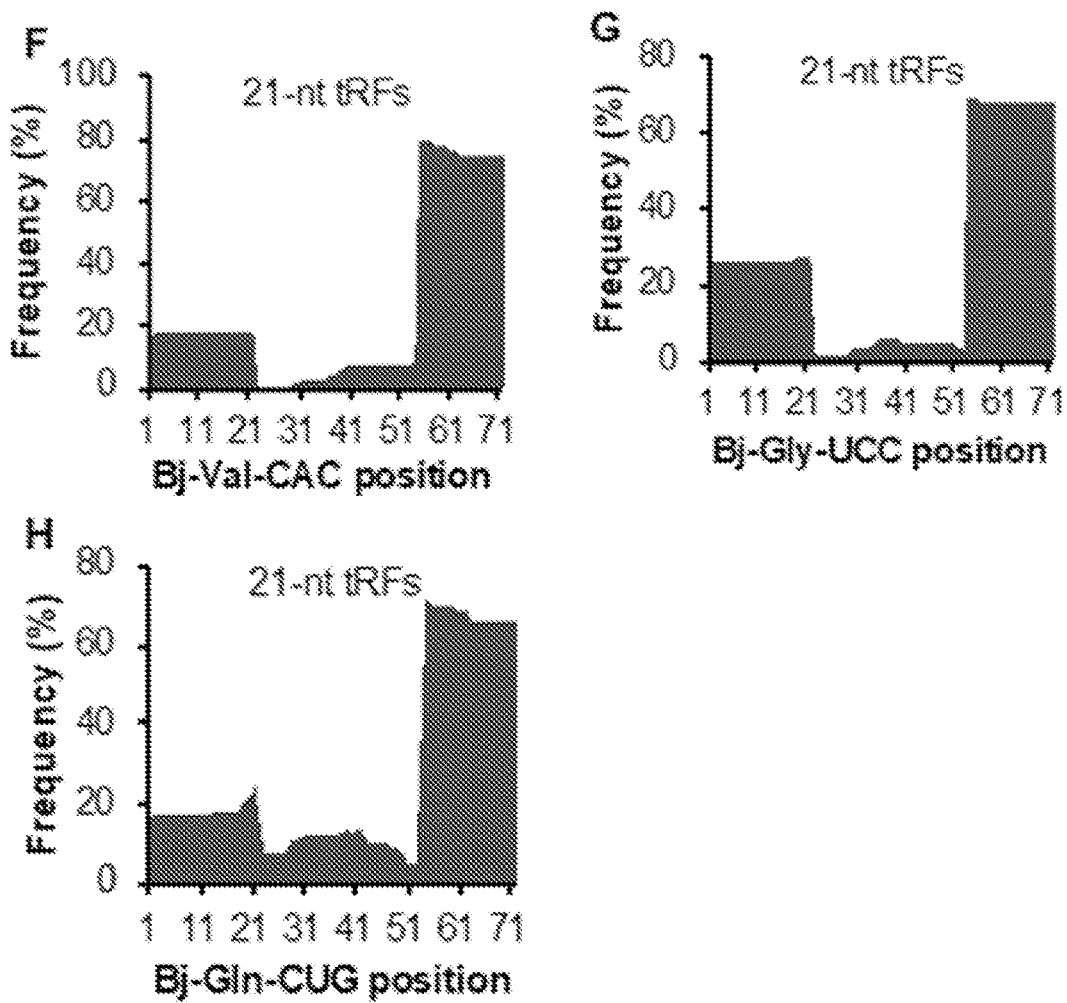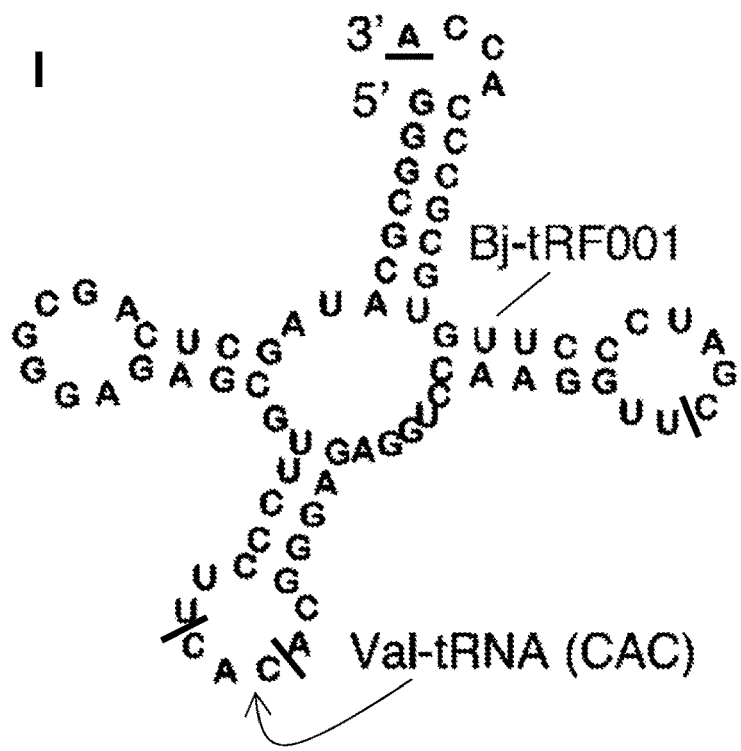
Figure 2

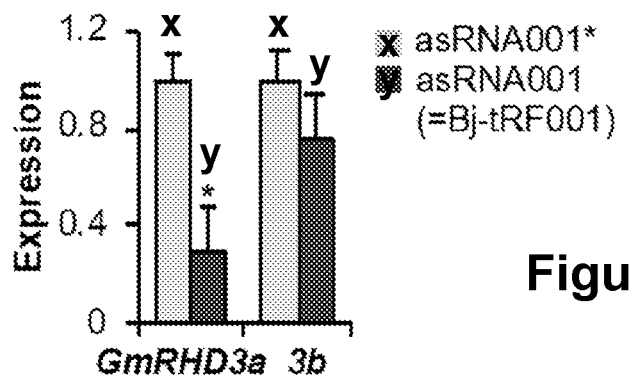

Figure 7A

Figure 8B
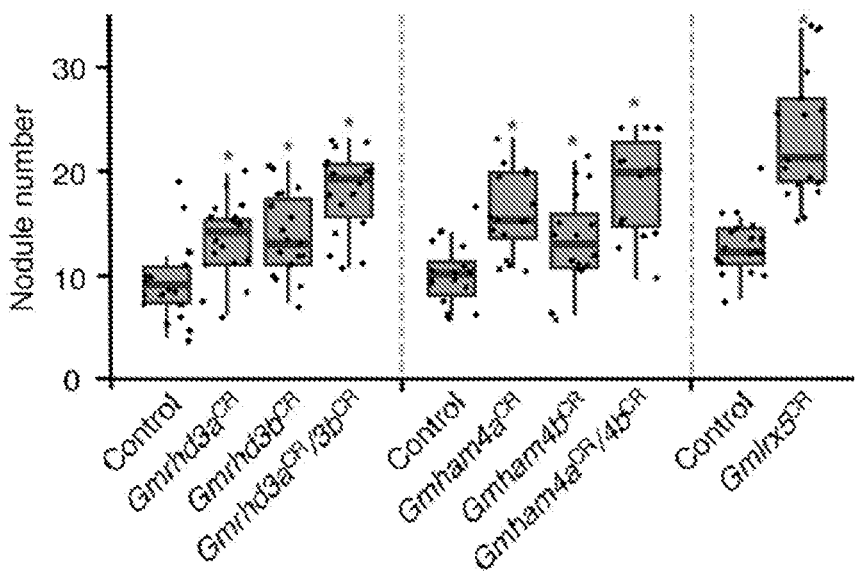
Figure 9A
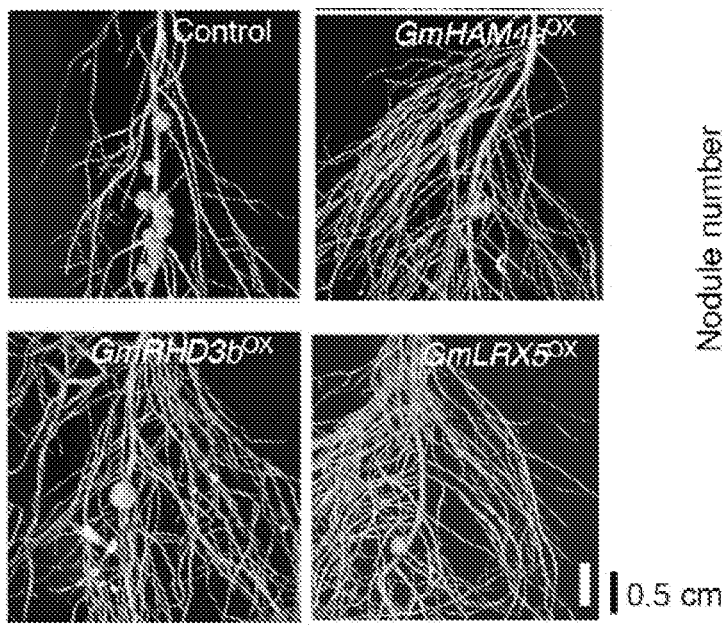
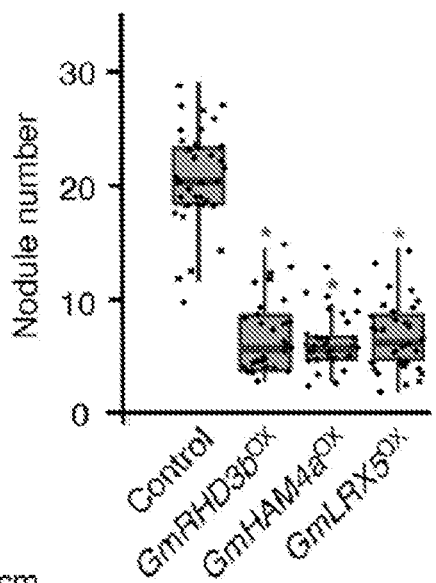
Figure 9B
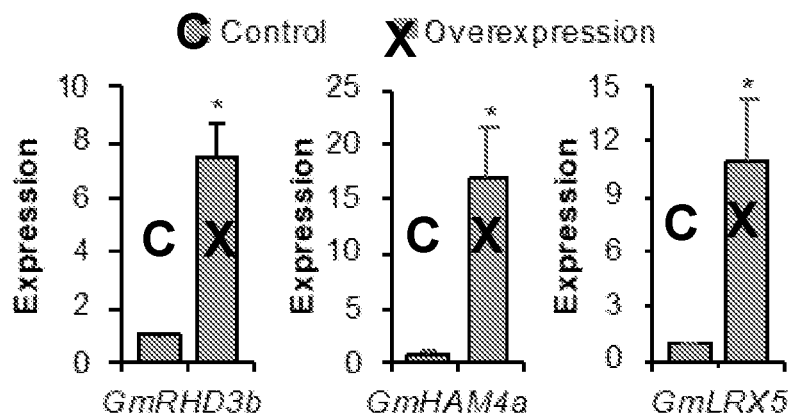
Figure 9C

⬢ Control
⬢ STTM tRF-silencing

A

```
Bj-tRF001:                            3' ACCACCCGCGUGUUCCCUAGC 5'
Construct-Wild type (W1):  p35S::GFP-5' TGGTGGGCTT[AC]AGGGGATCG 3'
Construct-Mutation (M1):   p35S::GFP-5' TGGTGGGCTGTGTGGGGATCG 3'
                                                    *

Bj-tRF002:                            3' ACCUCGCCCACUUCCCUUAGC 5'
Construct-Wild type (W2):  p35S::GFP-5' GGGAGTGGGT[GA]GGAGAATCG 3'
Construct-Mutation (M2):   p35S::GFP-5' GGGAGTGGGACTTGAGAATCG 3'
                                                    *

Bj-tRF003:                            3' GAUGGCAAUGUGGUAAGGGGU 5'
Construct-Wild type (W3)   p35S::GFP-5' CCACCGGTAT[AC]CATTCTCCA 3'
Construct-Mutation (M3):   p35S::GFP-5' CCACCGGTAGTGGATTCTCCA 3'
                                                    *
```

B

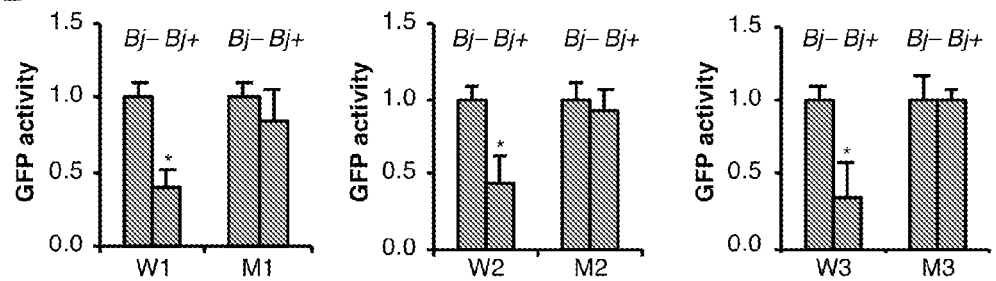

C

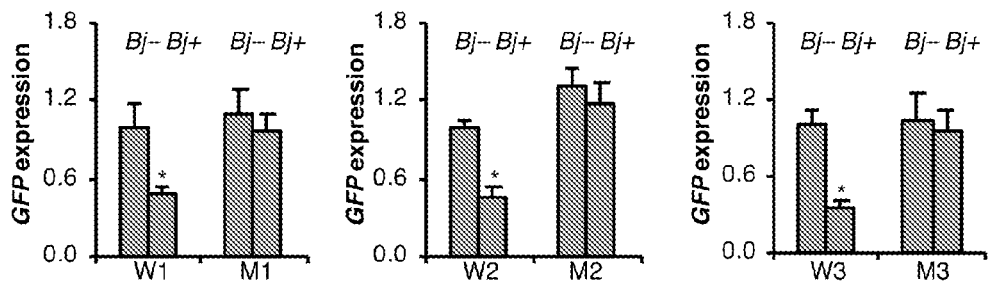

D

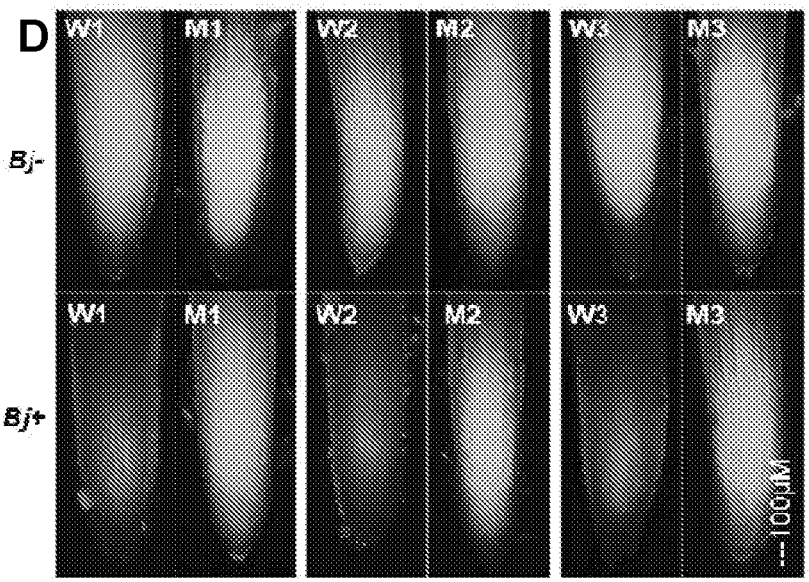

Figure 15

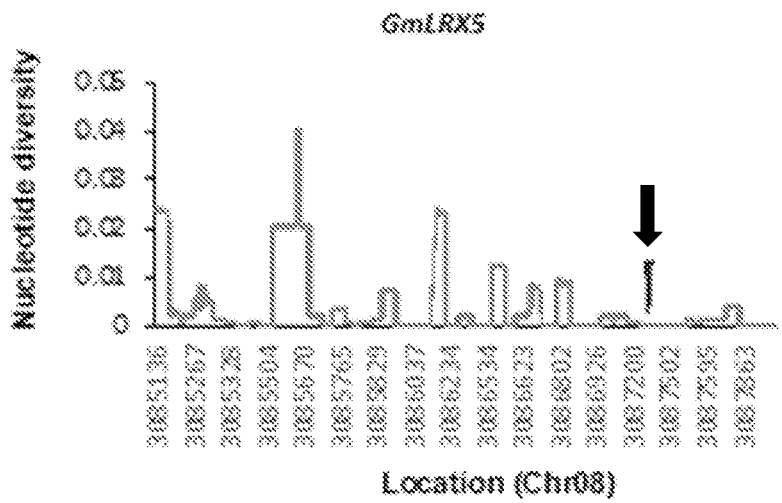

Figure 18

CAC
Sinorhizobium meliloti AK83
Sinorhizobium meliloti SM11
Sinorhizobium meliloti BL225c
Bradyrhizobium japonicum USDA110
Bradyrhizobium japonicum E109
Bradyrhizobium japonicum SEMIA 5079
Bradyrhizobium japonicum USDA6
Bradyrhizobium oligotrophicum S58
Bradyrhizobium sp BTAi1
Bradyrhizobium sp ORS278
Bradyrhizobium sp S23321
Mesorhizobium australicum WSM2073
Mesorhizobium huakuii 7653R
Mesorhizobium loti MAFF303099
Mesorhizobium opportunistum WSM2075

UCC

Bradyrhizobium japonicum USDA110
Bradyrhizobium japonicum E109
Bradyrhizobium japonicum SEMIA 5079
Bradyrhizobium japonicum USDA6
Bradyrhizobium oligotrophicum S58
Bradyrhizobium sp BTAi1
Bradyrhizobium sp ORS278
Bradyrhizobium sp S23321
Mesorhizobium australicum WSM2073
Mesorhizobium huakuii 7653R
Mesorhizobium loti MAFF303099
Mesorhizobium opportunistum WSM2075
Rhizobium etli CFN 42
Rhizobium etli CIAT652
Rhizobium etli bv mimosae str IE4771
Rhizobium etli bv mimosae str Mim1
Rhizobium etli bv phaseoli str IE4803
Rhizobium gallicum bv gallicum R602
Rhizobium leguminosarum bv trifolii CB782
Rhizobium leguminosarum bv trifolii WSM1325
Rhizobium leguminosarum bv trifolii WSM1689
Rhizobium leguminosarum bv trifolii WSM2304
Rhizobium leguminosarum bv viciae 3841
Rhizobium sp IRBG74
Rhizobium sp LPU83
Rhizobium sp NT-26
Rhizobium tropici CIAT899
Sinorhizobium fredii NGR234
Sinorhizobium medicae WSM419
Sinorhizobium meliloti 1021
Sinorhizobium meliloti 2011
Sinorhizobium meliloti AK83
Sinorhizobium meliloti BL225c
Sinorhizobium meliloti GR4
Sinorhizobium meliloti RMO17
Sinorhizobium meliloti Rm41
Sinorhizobium meliloti SM11

Figure 19C

CUG

Bradyrhizobium japonicum USDA110
Bradyrhizobium japonicum E109
Bradyrhizobium japonicum SEMIA 5079
Bradyrhizobium japonicum USDA6
Bradyrhizobium oligotrophicum S58
Bradyrhizobium sp BTAi1
Bradyrhizobium sp ORS278
Bradyrhizobium sp S23321
Mesorhizobium australicum WSM2073
Mesorhizobium huakuii 7653R
Mesorhizobium loti MAFF303099
Mesorhizobium opportunistum WSM2075
Rhizobium etli CFN 42
Rhizobium etli CIAT652
Rhizobium etli bv mimosae str IE4771
Rhizobium etli bv mimosae str Mim1
Rhizobium etli bv phaseoli str IE4803
Rhizobium gallicum bv gallicum R602
Rhizobium leguminosarum bv trifolii CB782
Rhizobium leguminosarum bv trifolii WSM1325
Rhizobium leguminosarum bv trifolii WSM1689
Rhizobium leguminosarum bv trifolii WSM2304
Rhizobium leguminosarum bv viciae 3841
Rhizobium sp IRBG74
Rhizobium sp LPU83
Rhizobium sp NT-26
Rhizobium tropici CIAT899
Sinorhizobium fredii NGR234
Sinorhizobium medicae WSM419
Sinorhizobium meliloti 1021
Sinorhizobium meliloti 2011
Sinorhizobium meliloti AK83
Sinorhizobium meliloti BL225c
Sinorhizobium meliloti GR4
Sinorhizobium meliloti RMO17
Sinorhizobium meliloti Rm41
Sinorhizobium meliloti SM11

RHIZOBIAL tRNA-DERIVED SMALL RNAs AND USES THEREOF FOR REGULATING PLANT NODULATION

PRIORITY

This patent application is related to, claims the priority benefit of, and is a 35 U.S.C. 371 national stage application of International Patent Application Serial No. PCT/US2020/033464 to Ma et al., filed May 18, 2020, which relates to and claims the priority benefit of U.S. Provisional Patent Application Ser. No. 62/848,672, filed May 16, 2019. The entire contents of each of the aforementioned priority applications are hereby expressly incorporated herein by reference in their entireties into this disclosure.

STATEMENT OF GOVERNMENT SUPPORT

This invention was made with government support under 2015-67013-22811 and 2018-67013-27425, both awarded by the United States Department of Agriculture National Institute of Food and Agriculture (USDA-NIFA). The government has certain rights in the invention.

FIELD

This disclosure is related to enhancing nodulation efficiency in legumes and for extending symbiotic nitrogen fixation capabilities to non-legumes. Particularly, Rhizobial tRNA-derived small RNA fragments (tRFs) and their impacts on soybean root nodule initiation provide alternative targets and mechanisms to increase nitrogen fixation capability in plants.

BACKGROUND

This section introduces aspects that may help facilitate a better understanding of the disclosure. Accordingly, these statements are to be read in this light and are not to be understood as admissions about what is or is not prior art.

Legumes are plants, such as soybeans, alfalfa, clover, peas, beans, lentils, lupins, mesquite, and peanuts, that form a symbiotic relationship between their roots and bacteria, specifically of the family Rhizobiaceae. Rhizobial lipo-chitooligosaccharidic nodulation (Nod) factors are the key signal molecules responsible for induction of plant responses that lead to nodule formulation. Upon perception of plant flavonoids, *Rhizobia* secrete Nod factors, which induce root hair curling around the bacteria and the subsequent development of infection treads that allow the bacteria to penetrate the cortical cells of the roots to form nodules.

Nodulation in legumes provides a major conduit of available nitrogen into the biosphere. More specifically, the plant provides the bacteria both sustenance and an energy source in the form of adenosine triphosphate (ATP) that is generated by photosynthesis. In return, the bacteria fix elemental nitrogen from the atmosphere into ammonia, a usable form of nitrogen that is digestible by plants. This interaction, called symbiotic nitrogen fixation (SNF), is important because it enables the plant hosts to access atmospheric nitrogen and, thus, provides a rich nitrogen source to the plant. SNF occurs in specialized root organs known as nodules of legumes and is a major source of nitrogen in agricultural and natural eco-systems. As nitrogen is the nutrient that most frequently limits the growth of green plants, optimizing its application is a key to optimizing plant yield.

Legumes are generally higher in protein content than other plant families due to the availability of nitrogen from nitrogen fixation. The high protein content makes legumes one of the most important food crops for both human consumption and animal feed. Further, legumes are used in crop rotation practice to increase the nitrogen content of soils, through SNF, for future growth seasons and to reduce the amount of fertilizer required. This has cost benefits to the grower and can reduce nitrogen runoff.

To optimize legume crop yield, it is important to increase efficiencies of nodulation and nitrogen fixation, which maintain adequate nitrogen levels in the plants. Accordingly, what is needed is an efficient and cost-effective approach to improve nodulation of legumes and, thus, increase the plant's yield potential.

BRIEF SUMMARY

Transgenic leguminous plants, plant roots, and plant cells are provided. In at least one exemplary embodiment, such leguminous plants, plant roots, and plant cells comprise at least one mutation to express a polynucleotide construct encoding rhizobial-derived RNA having a hairpin structure that is cleaved in vivo in the plant root into an artificial small RNA fragment (i.e. "artificial tRFs"). The artificial small RNA fragments/tRFs downregulate or repress one or more target genes of the leguminous plant, plant root or plant cell that are negative regulators of nodulation. In this manner, the transgenic leguminous plant, plant root, or plant cell produces increased nodules when inoculated with a *rhizobium* as compared to nodules produced from a corresponding inoculated wild type legume plant, plant root, or plant cell. In certain embodiments, the leguminous plant, plant root, or plant cell is *Glycine max* and the artificial small RNA fragment has a nucleotide sequence selected from a group consisting of SEQ ID NOs: 1-3, SEQ ID NOs: 50-70, and a substantially homologous nucleic acid sequence of SEQ ID NOs: 1-3, SEQ ID NOs: 50-70. In at least one exemplary embodiment, the nucleotide sequence of the artificial small RNA fragment is SEQ ID NO: 1, SEQ ID NO: 2, SEQ ID NO: 3, or a substantially homologous nucleic acid sequence of SEQ ID NOs: 1-3. In an alternative embodiment, the leguminous plant, plant root, or plant cell is *Rhizobium etli* and the nucleotide sequence of the artificial small RNA fragment is SEQ ID NOs: 34-49 or a substantially homologous nucleic acid sequence of SEQ ID NOs: 34-49.

In other embodiments, the least one mutation may further comprise a second mutation in at least one of the one or more target genes of the leguminous plant, plant root or plant cell. There, the second mutation can be designed to downregulate or repress the one or more target genes. Such target genes may comprise any host plant genes that are negative regulators of the nodulation mechanism such as, by way of nonlimiting example, GmRHD3a, GmRHD3b, GmHAM4a, GmHAM4b, GmLRX5, or an ortholog of the any of the foregoing. It will further be appreciated that one or any combination of the foregoing genes may also comprise this second mutation. For example, the second mutation may be at both GmRHD3a and GmRHD3b, or both GmHAM4a and GmHAM4b. Additionally or alternatively, the second mutation may comprise a deletion. There, all of the target genes may be deleted or, one or more of the target genes may be deleted while other target genes are simply repressed or unmodified.

Methods for increasing nodulation activity in a leguminous plant root are also provided. Such methods may comprise repressing or downregulating expression of one or more target genes of a host plant root or cell, each of the target genes being a negative regulator of nodulation in the host, and inoculating, or having inoculated, the modified plant host root or cell with at least one *rhizobium* to initiate nodulation. In at least one embodiment, the target gene(s) may be one or more of: RHD3, HAM4, LRX5, an ortholog of RHD3, an ortholog of HAM4, and an ortholog of LRX5 and/or the species or strain(s) of the at least one *rhizobium* is selected from a group consisting of: *Bradyrhizobium japonicum, Rhizobium etli, Sinorhizobium meliloti, Rhizobium leguminosarum, Parasponia rhizobium*, and *Mesorhizobium loti*. In at least one exemplary embodiment, the host root or cell is *Glycine max* and each target gene is selected from a group consisting of: GmRHD3a, GmRHD3b, GmHAM4a, GmHAM4b, and GmLRX5.

The repressing or downregulating step may comprise introducing and expressing a first polynucleotide construct encoding rhizobial-derived RNA, the rhizobial-derived RNA for producing one or more artificial small RNA fragments ("artificial tRFs") in the plant root that downregulate at least one of the target genes. In at least one embodiment, such rhizobial-derived RNA may have a hairpin structure that is cleaved in vivo to produce the artificial tRFs in the plant root. Furthermore, each of the artificial tRFs may have a nucleotide sequence selected from a group consisting of: SEQ ID NOs: 1-3, SEQ ID NOs: 34-70, or a substantially homologous nucleic acid sequence of SEQ ID NOs: 1-3 or SEQ ID NOs: 34-70. Still further, each of the artificial tRFs may have a nucleotide sequence of SEQ ID NO. 1, SEQ ID NO. 2, SEQ ID NO. 3, or a substantially homologous nucleic acid sequence of SEQ ID NO. 1, SEQ ID NO. 2, or SEQ ID NO. 3. Additionally or alternatively, the repressing or downregulating step may comprise constructing a CRISPR-Cas9 vector to silence one or more of the target genes and expressing the vector in the host plant root or cell. In at least one exemplary embodiment, the host root or cell is *Glycine max* and each target gene is selected from a group consisting of: GmRHD3a (which encodes SEQ ID NO: 80), GmRHD3b (which encodes SEQ ID NO: 81), GmHAM4a (which encodes SEQ ID NO: 82), GmHAM4b (which encodes SEQ ID NO: 83), GmLRX5 (which encodes SEQ ID NO: 84).

In yet another embodiment, where the target gene(s) are GmRHD3a, GmRHD3b, or both, the CRISPR-Cas9 vector comprises SEQ ID NOs. 74 and 75; where the target gene(s) are GmHAM4a, GmHAM4b, or both, the CRISPR-Cas9 vector comprises SEQ ID NOs. 76 and 77; and/or where at least one of the target genes is GmLRX5, the CRISPR-Cas9 vector comprises SEQ ID NOs. 78 and 79. In at least one exemplary embodiment, the repressing or downregulating step comprises: introducing and expressing a first polynucleotide construct encoding rhizobial-derived RNA that is cleaved in vivo to produce one or more artificial small RNA fragments in the plant root; and expressing a CRISPR-Cas9 vector in the host plant root or cell, the CRRISPR-Cas9 vector constructed to silence one or more of the following host genes: GmRHD3a (which encodes SEQ ID NO: 80), GmRHD3b (which encodes SEQ ID NO: 81), GmRHD3a GmRHD3b, GmHAM4a (which encodes SEQ ID NO: 82), GmHAM4b (which encodes SEQ ID NO: 83), GmHAM4a GmHAM4b, GmLRX5 (which encodes SEQ ID NO: 84).

Additional embodiments of the method provide for repressing or downregulating the expression of the one or more host genes by introducing and expressing a second polynucleotide construct into the host plant root or cell, where the second polynucleotide construct selectively represses expression of the one or more target genes. Certain methods of the present disclosure may additionally or alternatively include the at least one *rhizobium* comprising one or more species or strains of a rhizobial microorganism that expresses a third polynucleotide construct that enhances production of one or more transfer ribonucleic acid-derived fragments (tRFs) as compared to production of tRFs in a corresponding wild-type rhizobial microorganism.

Novel constructs are also provided in the present disclosure, with embodiments of such constructs encoding a ribonucleic acid transcript that folds into a hairpin structure and is cleaved in vivo into an artificial small ribonucleic acid molecule that, when expressed in a leguminous plant root, increases root nodule formation. In at least one non-limiting embodiment, the artificial small ribonucleic acid molecule has a nucleotide sequence selected from a group consisting of SEQ ID NOs. 1-3, 34-49, and 50-70. Such novel constructs may be utilized in any of the transgenic plants, plant roots, plant cells, and methods of the present disclosure.

Still further, certain embodiments provide for a rhizobial microorganism exhibiting selectively amplified production of one or more transfer ribonucleic acid-derived fragments (tRFs) as compared to production of tRFs in a corresponding wild-type rhizobial microorganism. For example, such a rhizobial microorganism may express a polynucleotide construct that enhances production of one or more tRFs and, in at least one embodiment, such tRFs may be capable of repressing or downregulating expression of at least one target gene of a host organism (such as the target genes previously described). In at least one embodiment, the at least one target genes of the host organism is selected from a group consisting of: RHD3, HAM4, LRX5 or an ortholog thereof. In yet another embodiment, the host organism is *Glycine max* and each of the at least one target genes is selected from a group consisting of: GmRHD3a (which encodes SEQ ID NO: 80), GmRHD3b (which encodes SEQ ID NO: 81), GmHAM4a (which encodes SEQ ID NO: 82), GmHAM4b (which encodes SEQ ID NO: 83), and GmLRX5 (which encodes SEQ ID NO: 84). Certain other embodiments provide for a compound comprising one or more species or strains of the rhizobial microorganism described herein, wherein the tRFs repress or downregulate expression of at least one target gene of a host plant root and the compound is formulated in an inoculant composition.

BRIEF DESCRIPTION OF THE SEQUENCE LISTINGS

SEQ ID NO: 1 is a nucleic acid sequence of a *Bradyrhizobium japonicum*-derived tRF: CGAUCCCUU-GUGCGCCCACCA;

SEQ ID NO: 2 is a nucleic acid sequence of a *B. japonicum*-derived tRF: CGAUUCCCUUCACCCG-CUCCA;

SEQ ID NO: 3 is a nucleic acid sequence of a *B. japonicum*-derived tRF: UGGGGAAUGGU-GUAACGGUAG;

SEQ ID NO: 4 is an artificial nucleic acid sequence of oligonucleotides targeting RHD3 (RHD3_pSC_F): ATTGAGGTGAAGTTGGCTGAATG;

SEQ ID NO: 5 is an artificial nucleic acid sequence of oligonucleotides targeting RHD3 (RHD3_pSC_B): AACCATTCAGCCAACTTCACCTC;

SEQ ID NO: 6 is an artificial nucleic acid sequence of oligonucleotides targeting HAM4 (HAM4_pSC_F): ATTGCCTGTGGGGATGAGGGAAC;

SEQ ID NO: 7 is an artificial nucleic acid sequence of oligonucleotides targeting HAM4 (HAM4_pSC_B): AACGTTCCCTCATCCCCACAGGC;

SEQ ID NO: 8 is an artificial nucleic acid sequence of oligonucleotides targeting LRX5 (LRX5_pSC_F): ATTGTTGAAACTGCTCTACGAAC;

SEQ ID NO: 9 is an artificial nucleic acid sequence of oligonucleotides targeting LRX5 (LRX5_pSC_B): AACGTTCGTAGAGCAGTTTCAAC;

SEQ ID NO: 10 is a nucleic acid sequence of a wild-type *B. japonicum*-derived tRF: CAAATCCTATCCCCGCAACCA;

SEQ ID NO: 11 is a nucleic acid sequence of a wild-type *B. japonicum*-derived tRF: CAAATCCTCTCGCTCCGACCA;

SEQ ID NO: 12 is a nucleic acid sequence of a wild-type *B. japonicum*-derived tRF: CAATCCTGTCTGGCAGCACCA;

SEQ ID NO: 13 is a nucleic acid sequence of a wild-type *B. japonicum*-derived tRF: CGAATCCAGCTGCCCCGACCA;

SEQ ID NO: 14 is a nucleic acid sequence of a wild-type *B. japonicum*-derived tRF: CGAATCCAGGTTCCCCAGCCA;

SEQ ID NO: 15 is a nucleic acid sequence of a wild-type *B. japonicum*-derived tRF: CGAATCCCACTCTCTCCGCCA;

SEQ ID NO: 16 is a nucleic acid sequence of a wild-type *B. japonicum*-derived tRF: CGAATCCCTCCCTCTCCGCCA;

SEQ ID NO: 17 is a nucleic acid sequence of a wild-type *B. japonicum*-derived tRF: CGAATCCTGCCACTCCGACCA;

SEQ ID NO: 18 is a nucleic acid sequence of a wild-type *B. japonicum*-derived tRF: CGAATCGTGTCGGGTGCGCCA;

SEQ ID NO: 19 is a nucleic acid sequence of a wild-type *B. japonicum*-derived tRF: CGAGCCCACCCAACTGTACCA;

SEQ ID NO: 20 is a nucleic acid sequence of a wild-type *B. japonicum*-derived tRF: CGAGCCCTGCCACTCCTGCCA;

SEQ ID NO: 21 is a nucleic acid sequence of a wild-type *B. japonicum*-derived tRF: CGAGTCATCCCGGGATCGCCA;

SEQ ID NO: 22 is a nucleic acid sequence of a wild-type *B. japonicum*-derived tRF: CGAGTCCCTCCGAGCGCACCA;

SEQ ID NO: 23 is a nucleic acid sequence of a wild-type *B. japonicum*-derived tRF: CGATCCCGTCTGGCTCCACCA;

SEQ ID NO: 24 is a nucleic acid sequence of a wild-type *B. japonicum*-derived tRF: CGATCCCTGTCGTGCCCACCA;

SEQ ID NO: 25 is a nucleic acid sequence of a wild-type *B. japonicum*-derived tRF: CGATCCCTTGTGCGCCCACCA;

SEQ ID NO: 26 is a nucleic acid sequence of a wild-type *B. japonicum*-derived tRF: CGATTCCCTTCACCCGCTCCA;

SEQ ID NO: 27 is a nucleic acid sequence of a wild-type *B. japonicum*-derived tRF: CGATTCCCTTCGCCCGCTCCA;

SEQ ID NO: 28 is a nucleic acid sequence of a wild-type *B. japonicum*-derived tRF: CGATTCCGCCCCTGGGCACCA;

SEQ ID NO: 29 is a nucleic acid sequence of a wild-type *B. japonicum*-derived tRF: GCGCTCGTGGCGGAACTGGTA;

SEQ ID NO: 30 is a nucleic acid sequence of a wild-type *B. japonicum*-derived tRF: GCGGGTGTAGCTCAGTGGTAG;

SEQ ID NO: 31 is a nucleic acid sequence of a wild-type *B. japonicum*-derived tRF: TCCTCGGTAGCTCAGCGGTAG;

SEQ ID NO: 32 is a nucleic acid sequence of a wild-type *B. japonicum*-derived tRF: TGGGGAATGGTGTAACGGTAG;

SEQ ID NO: 33 is a nucleic acid sequence of a wild-type *B. japonicum*-derived tRF: TTGGTAGACGCAAGGGACTTA;

SEQ ID NO: 34 is a nucleic acid sequence of a wild-type *Rhizobium etli*-derived tRF: CAAATCCCTCCTCCGCTACCA;

SEQ ID NO: 35 is a nucleic acid sequence of a wild-type *Rhizobium etli*-derived tRF: CAAGTCTTCCCGGGCCCACCA;

SEQ ID NO: 36 is a nucleic acid sequence of a wild-type *Rhizobium etli*-derived tRF: CGAGTCCAGGTTCCCCAGCCA;

SEQ ID NO: 37 is a nucleic acid sequence of a wild-type *Rhizobium etli*-derived tRF: AGTAGGTCAGAGCAGAGGAAT;

SEQ ID NO: 38 is a nucleic acid sequence of a wild-type *Rhizobium etli*-derived tRF: AGTAGGTCAGAGCAGAGGAAT;

SEQ ID NO: 39 is a nucleic acid sequence of a wild-type *Rhizobium etli*-derived tRF: AGTAGGTCAGAGCAGAGGAAT;

SEQ ID NO: 40 is a nucleic acid sequence of a wild-type *Rhizobium etli*-derived tRF: CAAGTCTTCCCGGGCCCACCA;

SEQ ID NO: 41 is a nucleic acid sequence of a wild-type *Rhizobium etli*-derived tRF: CGAATCACTCCACTCCGACCA;

SEQ ID NO: 42 is a nucleic acid sequence of a wild-type *Rhizobium etli*-derived tRF: CGAATCCGGCCCGGGGAGCCA;

SEQ ID NO: 43 is a nucleic acid sequence of a wild-type *Rhizobium etli*-derived tRF: CGAGCCCTGCTGCCCCTGCCA;

SEQ ID NO: 44 is a nucleic acid sequence of a wild-type *Rhizobium etli*-derived tRF: CGAGTCTCTCATCGCCCACCA;

SEQ ID NO: 45 is a nucleic acid sequence of a wild-type *Rhizobium etli*-derived tRF: GATTTTCATTCTGTAAAGAGG;

SEQ ID NO: 46 is a nucleic acid sequence of a wild-type *Rhizobium etli*-derived tRF: GATTTTCATTCTGTAAAGAGG;

SEQ ID NO: 47 is a nucleic acid sequence of a wild-type *Rhizobium etli*-derived tRF: GTAGGTCAGAGCAGAGGAATC;

SEQ ID NO: 48 is a nucleic acid sequence of a wild-type *Rhizobium etli*-derived tRF: GTAGGTCAGAGCAGAGGAATC;

SEQ ID NO: 49 is a nucleic acid sequence of a wild-type *Rhizobium etli*-derived tRF: GTAGGTCAGAGCAGAGGAATC;

SEQ ID NO: 50 is a nucleic acid sequence of a *B. japonicum*-derived tRF: CAAAUCCUAUCCCCGCAACCA;

SEQ ID NO: 51 is a nucleic acid sequence of a *B. japonicum*-derived tRF: CAAAUCCUCUCG-CUCCGACCA;

SEQ ID NO: 52 is a nucleic acid sequence of a *B. japonicum*-derived tRF: CAAUCCUGU-CUGGCAGCACCA;

SEQ ID NO: 53 is a nucleic acid sequence of a *B. japonicum*-derived tRF: CGAAUCCAGCUGCCCCGACCA;

SEQ ID NO: 54 is a nucleic acid sequence of a *B. japonicum*-derived tRF: CGAAUCCAG-GUUCCCCAGCCA;

SEQ ID NO: 55 is a nucleic acid sequence of a *B. japonicum*-derived tRF: CGAAUCCCACUCU-CUCCGCCA;

SEQ ID NO: 56 is a nucleic acid sequence of a *B. japonicum*-derived tRF: CGAAUCCCUCCCU-CUCCGCCA SEQ ID NO: 57 is a nucleic acid sequence of a *B. japonicum*-derived tRF: CGAAUC-CUGCCACUCCGACCA;

SEQ ID NO: 58 is a nucleic acid sequence of a *B. japonicum*-derived tRF: CGAAUCGUGUCGG-GUGCGCCA;

SEQ ID NO: 59 is a nucleic acid sequence of a *B. japonicum*-derived tRF: CGAGCCCACCCAACU-GUACCA;

SEQ ID NO: 60 is a nucleic acid sequence of a *B. japonicum*-derived tRF: CGAGCCCUGCCACUC-CUGCCA;

SEQ ID NO: 61 is a nucleic acid sequence of a *B. japonicum*-derived tRF: CGAGUCAUCCCGG-GAUCGCCA;

SEQ ID NO: 62 is a nucleic acid sequence of a *B. japonicum*-derived tRF: CGAGUCC-CUCCGAGCGCACCA;

SEQ ID NO: 63 is a nucleic acid sequence of a *B. japonicum*-derived tRF: CGAUCCCGUCUGGCUC-CACCA;

SEQ ID NO: 64 is a nucleic acid sequence of a *B. japonicum*-derived tRF: CGAUCCCUGUCGUGCC-CACCA;

SEQ ID NO: 65 is a nucleic acid sequence of a *B. japonicum*-derived tRF: CGAUUCCCUUCGCCCG-CUCCA;

SEQ ID NO: 66 is a nucleic acid sequence of a *B. japonicum*-derived tRF: CGAUUCCGCCC-CUGGGCACCA;

SEQ ID NO: 67 is a nucleic acid sequence of a *B. japonicum*-derived tRF: GCGCUCGUGGCG-GAACUGGUA;

SEQ ID NO: 68 is a nucleic acid sequence of a *B. japonicum*-derived tRF: GCGGGUGUAG-CUCAGUGGUAG;

SEQ ID NO: 69 is a nucleic acid sequence of a *B. japonicum*-derived tRF: UCCUCGGUAG-CUCAGCGGUAG;

SEQ ID NO: 70 is a nucleic acid sequence of a *B. japonicum*-derived tRF: UUGGUA-GACGCAAGGGACUUA;

SEQ ID NO: 71 is a wild-type *B. japonicum* tRNA: GGGCGCAUAGCUCAGCGGGAGAGCGUUCCC-UUCACACGGGAGAGGUCCAAGGUUCG AUCC-CUUGUGCGCCCACCA;

SEQ ID NO: 72 is a wild-type *B. japonicum* tRNA: GCGGGUGUAGCUCAAUGGUAGAGCAGCAGC-CUUCCAAGCUGAAUACGAGGGUUCGA UUCC-CUUCACCCGCUCCA;

SEQ ID NO: 73 is a wild-type *B. japonicum* tRNA: UGGGGAAUGGUGUAACGGUAGCACAACAGA-CUCUGACUCUGUUUGUCUUGGUUCGA AUCCAGGUUCCCCAGCCA;

SEQ ID NO: 74 is an artificial nucleic acid sequence of a primer for an overexpression constructRHD3b (RHD3b_CDS_F): GCGCGTCGA-CATGGCAAATAGTGAGACTTGTTG;

SEQ ID NO: 75 is an artificial nucleic acid sequence of a primer for an overexpression constructRHD3b (RHD3b_CDS_B): gcgcTCTAGACTACTCATCTTT-TAATGGACTTGC;

SEQ ID NO: 76 is an artificial nucleic acid sequence of a primer for an overexpression constructHAM4a (HAM4a_CDS_F): TTGCctcgagAT-GAGAGTTCCCGTTCCCTCATCC;

SEQ ID NO: 77 is an artificial nucleic acid sequence of a primer for an overexpression constructHAM4a (HAM4a_CDS_B): GCTTggtaccCTAACAGCGC-CATGCTGACGTGGCA;

SEQ ID NO: 78 is an artificial nucleic acid sequence of a primer for an overexpression construct LRX5 (LRX5_CDS_F): gcgcGTCGACATGATGATGAT-GATGAAGAAGAAGG;

SEQ ID NO: 79 is an artificial nucleic acid sequence of a primer for an overexpression constructLRX5 (LRX5_CDS_B): gcaaTCTA-GACTAATAAAAGGGTGGTGGTGGAGGC.

SEQ ID NO: 80 is an amino acid sequence encoded by *Glycine max* gene GmRHD3a (Glyma.07G010200).

SEQ ID NO: 81 is an amino acid sequence encoded by *Glycine max* gene GmRHD3b (Glyma.08G0193200).

SEQ ID NO: 82 is an amino acid sequence encoded by *Glycine max* gene GmHAM4a (Glyma.01G177200).

SEQ ID NO: 83 is an amino acid sequence encoded by *Glycine max* gene GmHAM4b (Glyma.11G065200).

SEQ ID NO: 84 is an amino acid sequence encoded by *Glycine max* gene GmLRX5 (Glyma.08G039400).

In addition to the foregoing, the above-described sequences have been submitted electronically in computer readable form, ASCII format (file entitled "68447-03SequenceListingST25_fl8apr.2025.txt"; file size=148,863,110 bytes; date created Apr. 22, 2025), which is hereby incorporated by reference in its entirety. The information recorded in computer readable form is identical to the written Sequence Listings provided above, pursuant to 37 C.F.R. § 1.821(f).

BRIEF DESCRIPTION OF THE DRAWINGS

The disclosed embodiments and other features, advantages, and aspects contained herein, and the matter of attaining them, will become apparent in light of the following detailed description of various exemplary embodiments of the present disclosure. Such detailed description will be better understood when taken in conjunction with the accompanying drawings, wherein:

FIG. 6E shows the cleavage sites within mRNAs of identified rhizobial tRF target genes pursuant to the present disclosure, with distribution (x-axes) of cleavage sites within the mRNAs of the five soybean genes and times (y-axes) of cleavage in 20-dpi nodules and uninoculated roots detected by sequencing the RLM-RACE products; dots pointing to the sites between the boxed nucleotides represent cleavage sites, some of the 5' and 3'UTRs (labeled U), introns (labeled I), and exons (labeled E) of the soybean genes, their mRNAs, and the identified tRF target sites indicated by their respective labels, alignments and arrows;

FIG. 7A shows the sequences of hairy root mutations created by site-specific CRISPR-Cas9 editing of GmRHD3a 3b, GmHAM4a 4b, and GmLRX5, with the wild-type of exonic sequence of each gene for editing and the corresponding amino acid sequence shown on the top of each panel, the protospacer-adjacent motifs (PAMs) used for design guided RNAs underlined, and nucleotide deletions, insertions and substitutions created by CRISPR-Cas9 each positioned within a box (E); asterisks denote the consensus nucleotides;

FIG. 8B shows a graph of nodule numbers from the mutants and controls as exemplified in FIG. 8A, with all data points represented by dots and shown as box and whisker plots displaying 95 to 5% interval from three biological replicates (12 plants per replicate) collected 28 days after inoculation (asterisks indicate the significance level of $P<0.01$ (Student's t test); shown as means standard deviations from three independent experiments (n=12 per experiment);

FIG. 9A shows photographs of transgenic roots engineered to overexpress three of the tRF targets of the present disclosure (GmRHD3b, GmHAM4a, and GmLRX5), with all mutants producing reduced nodule numbers relative to the control; FIG. 9B shows a graph of the nodule numbers from the mutants and control as exemplified in FIG. 9A (all data points represented by dots and shown as box and whisker plots displaying 95 to 5% interval from three biological replicates (12 plants per replicate) collected 28 days after inoculation (asterisks indicate the significance level of $P<0.01$ (Student's t-test); shown as means±standard deviations from three independent experiments (n=12 per experiment)); and FIG. 9C shows graphical data related to the overexpression of rhizobial tRF targets in hairy roots as compared with that in empty vector transgenic controls, with ** indicating significant difference (t-test, $P<0.01$), levels of gene expression relative to that of GmELF1b as detected by qRT-PCR, shown as means±errors from three biological replicates, and, in each panel, the expression level of one sample was set as 1 and those of the other adjusted accordingly;

FIG. 15, subpart A is a schematic of GFP-tRF target sites constructs, with W1-W3 representing three wild-type transgenic roots and M1-M3 representing three mutation type transgenic roots prepared according to the present disclosure, with the nucleotides within each box (□) representing cleavage sites and underlines and asterisks denoting mutations; subpart B showing graphical data resulting from the quantitation of GFP signals shown in subpart D of FIG. 15, where the GFP signals were measured using the ImageJ software and error bars indicating s.d. of GFP signals from 12 images; subpart C shows graphical data related to the reduction of expression levels of GFP fusion genes relative to that of GmEFLb in wild-type fusion gene transgenic roots 24 hrs post inoculation (hpi) with USDA110, where GFP transcript abundance was measured by qRT-PCR and the value of one sample was set at 1 and those of the others adjusted accordingly (values shown as means±s.e. from three biological replicates, and the value of one sample set as 1 and those of the other adjusted accordingly, Bj+ indicating inoculated roots 24 hpi, Bj− indicated uninoculated roots and asterisks above columns indicative of the significance level at P<0.01 (t-test)); and subpart D shows photographs of GFP activity in transgenic roots of "GFP-tRF target site" fusion genes (W1 to W3) and "GFP-mutated tRF target site" (M1 to M3) 24 hours after inoculation with USDA110, with Bj− and Bj+ indicating uninoculated and inoculated roots, respectively;

FIGS. 17 and 18 show graphical data related to the nucleotide diversity (7I) along each of the five rhizobial targets in soybean populations, with the x-axes representing the nucleotide positions of each of the five soybean genes in the soybean reference genome (cv., Williams 82, version 2), the y-axes representing the levels of diversity of individual nucleotide positions among the 699 soybean accessions, and the arrows pointing to the tRF target sites within the five genes;

FIGS. 19A-19C illustrate the sequence conservation and divergence of three rhizobial tRNAs among four *rhizobium* groups, with FIG. 19A showing Val-1-tRNA (CAC), FIG. 19B showing Gly-1-tRNA (UCC), and FIG. 19C showing Gln-1-tRNA (CUG)

Figure 1:
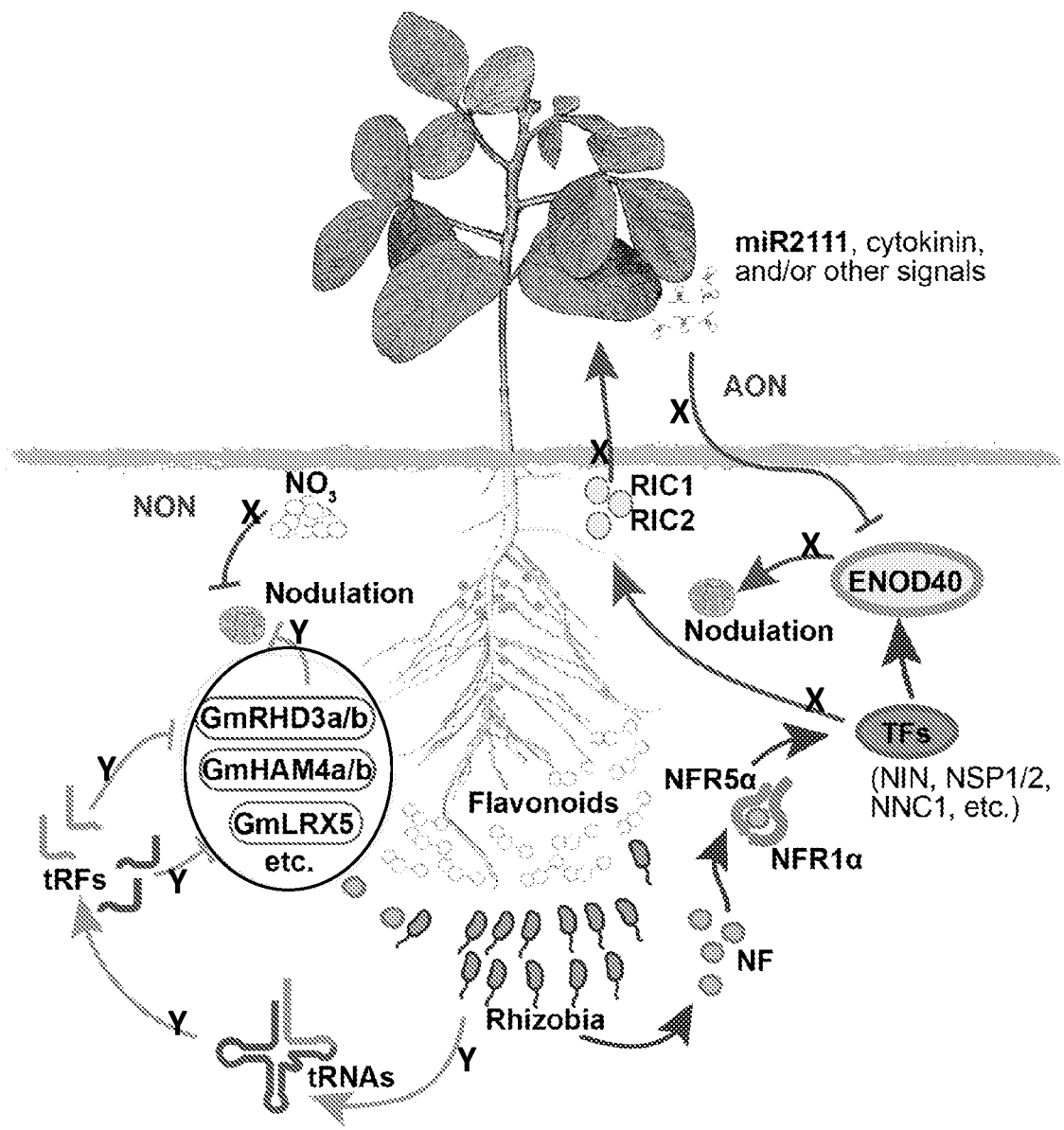
FIG. 1 is a schematic depiction of the mechanisms that regulate soybean nodulation and, thus, nodule numbers, with the lines labeled X indicating plant-based negative regulation of nodulation and lines labeled Y indicating *Rhizobium*-based positive regulation of nodulation as described herein (AON=autoregulation of nodulation; NON=nitrogen regulation of nodulation; and RIC1 and RIC2=nitrogen-suppression CLAVATA3/EMBRYO SURROUNDING REGION-RELATED (CLE) peptides 1 and 2)

While the present disclosure is susceptible to various modifications and alternative forms, exemplary embodiments thereof are shown by way of example in the drawings and are herein described in detail.

DETAILED DESCRIPTION

For the purposes of promoting an understanding of the principles of the present disclosure, reference will now be made to the embodiments illustrated in the drawings and specific language will be used to describe the same. It will nevertheless be understood that no limitation of scope is intended by the description of these embodiments. On the contrary, this disclosure is intended to cover alternatives, modifications, and equivalents as may be included within the spirit and scope of this application as defined by the appended claims. As previously noted, while this technology may be illustrated and described in one or more preferred embodiments, the compositions, systems and methods hereof may comprise many different configurations, forms, materials, and accessories.

In the following description, numerous specific details are set forth in order to provide a thorough understanding of the present disclosure. Particular examples may be implemented without some or all of these specific details and it is to be understood that this disclosure is not limited to particular biological systems, which can, of course, vary.

Unless defined otherwise, all technical and scientific terms used herein have the same meaning as commonly understood by one of skill in the relevant arts. Although any methods and materials similar to or equivalent to those described herein can be used in the practice or testing of the subject of the present application, the preferred methods and materials are described herein. To facilitate understanding of the invention, a number of terms are defined below. All publications, patents and patent applications cited herein, whether supra or infra, are hereby incorporated by reference in their entirety to the extent that the reference is not inconsistent with the teachings provided herein. Additionally, as used in this specification and the appended claims, the singular forms "a", "an" and "the" include plural referents unless the content clearly dictates otherwise. Thus, for example, reference to "a tRNA" includes a combination of two or more tRNAs; reference to "bacteria" includes mixtures of bacteria, and the like.

Furthermore, unless specifically stated otherwise, the term "about" can allow for a degree of variability in a value or range, for example, within plus or minus 10%, within 5%, or within 1% of a stated value or limit of a range for percentages and plus or minus 1.0 unit for unit values, for example, about 1.0 refers to a range of values from 0.9 to 1.1. The term "substantially" can allow for a degree of variability in a value or range, for example, within 90%, within 95%, or within 99% of a stated value or of a stated limit of a range.

The term "plant" includes whole plants, plant organs (e.g., leaves, stems, flowers, roots, reproductive organs, embryos and parts thereof, etc.), seedlings, seeds and plant cells and progeny thereof. While the class of plants of predominant focus in the present disclosure relates to legumes, it will be understood that the inventive techniques and concepts hereof is not limited to any particular class of higher plants and the methods hereof are generally as broad as the class of higher plants amenable to transformation techniques and/or that exhibit nodulation or a similar symbiotic, cross-kingdom mechanism.

A "leguminous plant" as referred to herein is any member of the Fabaceae (or Leguminosae) family that can form nodules when infected with a rhizobial microorganism.

As used herein, the term "transgenic plants" or "transgenic plant roots" or "transgenic plant cells" refers to plants, *Agrobacterium*-induced plant roots, and plant cells that have DNA sequences not normally transcribed into RNA or translated into a protein ("expressed"), including, but not limited to genes that are perhaps not normally present, or any other genes or DNA sequences that one desires to introduce into the non-transformed plant, but which one desires to either genetically engineer or to have altered expression. It is contemplated that in some instances the genome of transgenic plants of the present invention will have been augmented through the stable introduction of the transgene; however, in other instances, the introduced gene will replace an endogenous sequence. A transgenic plant/root/cell includes a plant/root/cell regenerated from an originally-transformed plant or cell of the present disclosure and progeny transgenic plants from later generations or crosses of a transformed plant described herein.

A "rhizobial microorganism" as referred to herein may include any microorganism that is capable of fixing nitrogen after becoming established in a root nodule of a leguminous plant.

As used herein, "inoculating" means any method or process where a leguminous plant (including a leguminous plant seed or root) is brought into contact with a rhizobial microorganism. In some embodiments, inoculating may comprise the rhizobial microorganism being applied to the soil in which the plant is growing. In other instances, inoculating may comprise the rhizobial microorganism being applied to a portion of the plant root.

Further, as used herein, the terms "overexpression" (when used in connection with a gene), and "upregulation" have the meaning ascribed thereto by one of ordinary skill in the relevant arts, which includes (without limitation) the overexpression or misexpression of a wild-type gene product that may cause mutant phenotypes and/or lead to abundant target protein or small RNA fragment expression. "Down-regulation" or "down-regulated" may be used interchangeably and refer to a decrease in the level of a marker, such as a gene, nucleic acid, metabolite, transcript, protein, or polypeptide, as compared to an established level (e.g., that of a corresponding wild-type gene).

The terms "knockout," "elimination," and "deletion" in the present disclosure are used interchangeably and mean any addition or loss of a target gene sequence of a cell genome so that the protein expression mediated by the target gene is completely removed.

As used herein, "CRISPR-Cas9" means the system composed of sgRNA (guide RNA) complementarily binding to the target genome and Cas9 protein that can cut the genome gene by binding to the sgRNA and the target genome simultaneously. As a result, when the sgRNA vector and Cas9 vector are expressed temporarily in cells together concurrently, sgRNA and Cas9 protein are produced to change targeted gene sequence, leading to modification of the targeted gene at the Cas9 binding site and possible disruption of the function of the gene.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, that are synthetic, naturally occurring, and non-naturally occurring, have similar binding properties as the reference nucleic acid, and metabolized in a manner similar to the reference nucleotides.

The terms "polypeptide," "peptide," and "protein" are used interchangeably herein to refer to a polymer of amino acid residues, a polypeptide, or a fragment of a polypeptide, peptide, or fusion polypeptide. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the corresponding naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e. a carbon that is bound to a hydrogen, a carboxyl group, an amino group, and an R group (e.g., homoserine, norleucine, methionine sulfoxide, methionine methyl sulfonium). Such analogs have modified R groups (e.g., norleucine) or modified peptide backbones, but retain the same basic chemical structure as a naturally occurring amino acid.

Amino acid mimetics refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, the term "regulatory element" means and includes, in its broadest context, a polynucleotide molecule having gene regulatory activity, i.e. one that has the ability to affect the transcription or translation of an operably linked transcribable polynucleotide molecule. Indeed, regulatory elements comprise a series of nucleotides that determine if, when, and at what level a particular gene is expressed. Regulatory elements such as promoters, leaders, introns and transcription termination regions are polynucleotide molecules having gene regulatory activity that play an integral part in the overall expression of genes in living cells. Promoters may be derived from a classical eukaryotic genomic gene, including (without limitation) the TATA box often used to achieve accurate transcription initiation, with or without a CCAAT box sequence and additional regulatory or control elements (i.e. upstream activating sequences, enhancers, and silencers) or may be the transcriptional regulatory sequences of a classical prokaryotic gene. The term "promote" may also be used herein to describe a synthetic or fusion molecule, or derivative that confers, activates, or enhances expression of a nucleic acid molecule in a cell, tissue, or organ. Promoters may contain additional copies of one or more specific regulatory elements to further enhance expression and/or to alter the spatial expression and/or temporal expression of a nucleic acid molecule, or to confer expression of a nucleic acid molecule to specific cells or tissues such as meristems, leaves, roots, embryo, flowers, seeds or fruits (i.e. a tissue-specific promoter). In the context of the present invention, a promoter preferably is a plant-expressible promoter sequence, meaning that the promoter sequence (including any additional regulatory elements added thereto or contained therein) is at least capable of inducing, conferring, activating, or enhancing expression in a plant cell, tissue or organ. Promoters that also function or solely function in non-plant cells such as bacteria, yeast cells, insect cells, and animal cells, however, are not excluded from the invention hereof.

As used herein, the term "operably linked" refers to a juxtaposition wherein the components so described are in a relationship permitting them to function in their intended manner. For example, a first polynucleotide molecule, such as a promoter, is "operably linked" with a second transcribable polynucleotide molecule, such as a gene of interest, where the polynucleotide molecules are so arranged that the first polynucleotide molecule affects the function of the second polynucleotide molecule. The two polynucleotide molecules may or may not be part of a single contiguous polynucleotide molecule and may or may not be adjacent. For example, a promoter is operably linked to a gene of interest if the promoter modulates transcription of the gene of interest in a cell.

The term "isolated" means that the material is removed from its original environment, e.g., the natural environment if it is naturally occurring. For example, a naturally-occurring polypeptide present within a living organism is not isolated, but the same polypeptide separated from some or all of the coexisting materials in the natural system is isolated. The term "purified" does not require absolute purity; instead, it is intended as a relative definition. In other words, "purified" indicates that the molecule is present in the substantial absence of other molecules of the same type. The term "purified" as used herein preferably means at least 75% by weight, more preferably at least 85% by weight, more preferably still at least 95% by weight, and most preferably at least 98% by weight, of molecules of the same type are present.

The terms "abundance" and "amount" are used interchangeably herein. "Amplification" refers to any means by which a polynucleotide sequence is copied and thus expanded into a larger number of polynucleotide molecules, e.g., by reverse transcription, polymerase chain reaction, and ligase chain reaction.

As used herein, an "analog" of a chemical compound is a compound that, by way of example, resembles another in structure but is not necessarily an isomer (e.g., 5-fluorouracil is an analog of thymine).

The term "polynucleotide" as used herein refers to a polymeric form of nucleotides of any length, either ribonucleotides or deoxyribonucleotides. This term refers only to the primary structure of the molecule and thus includes double- and single-stranded DNA and RNA. It also includes known types of modifications, for example, labels which are known in the art, methylation, "caps", substitution of one or more of the naturally occurring nucleotides with an analog, internucleotide modifications, such as those with uncharged linkages and with charged linkages, those containing pendant moieties, such as proteins, those with intercalators, those containing chelators, those containing alkylators, those with modified linkages, as well as unmodified forms of the polynucleotide.

As used herein, the term "expression cassette" refers to a molecule comprising at least one coding sequence operably linked to a control sequence which includes all nucleotide sequences required for the transcription of cloned copies of the coding sequence and the translation of the mRNAs in an appropriate host cell. Expression cassettes can include, but are not limited to, cloning vectors, specifically designed plasmids, viruses or virus particles. The cassettes may further include an origin of replication for autonomous replication in host cells, selectable markers, various restriction sites, a potential for high copy number and strong promoters.

A "vector" is a composition of matter which comprises an isolated nucleic acid, which can be used to transfer gene sequences between cells. Thus, the term includes cloning and expression vehicles, as well as viral vectors. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. As used herein, the terms "complementary" or "complementarity" are used in reference to polynucleotides (i.e., a sequence of nucleotides) related by the base pairing rules. For example, for the sequence "A G T," is complementary to the sequence "T C A." Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The terms "identical" or percent "identity," in the context of two or more nucleic acids or polypeptide sequences, refer to two or more sequences or subsequences that are the same or have a specified percentage of amino acid residues or nucleotides that are the same (i.e., at least about 50%, 65%, 75%, 85%, 95%, 99% or more) identity over a specified region, when compared and aligned for maximum correspondence over a comparison window, or designated region as measured using a sequence comparison algorithms, or by manual alignment and visual inspection. This definition also refers to the complement of a test sequence, which has substantial sequence or subsequence complementarity when the test sequence has substantial identity to a reference sequence. This definition also refers to the complement of a test sequence, which has substantial sequence or subsequence complementarity when the test sequence has substantial identity to a reference sequence.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Substantial identity of nucleic acid sequences can be determined by comparing the sequence identity of two sequences, for example by physical/chemical methods (i.e., hybridization) or by sequence alignment via computer algorithm.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

A "compound," as used herein, refers to a protein, polypeptide, an isolated nucleic acid, or other agent used in the method of the present disclosure.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

A "fragment" is a portion of an amino acid sequence, comprising at least one amino acid, or a portion of a nucleic acid sequence comprising at least one nucleotide.

As used herein, a "functional" biological molecule is a biological molecule in a form in which it exhibits a property or activity by which it is characterized. A functional enzyme, for example, is one which exhibits the characteristic catalytic activity by which the enzyme is characterized.

The phrase "level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured or discussed in terms of the actual amount of an mRNA or protein present. Such assays are coupled with processes or systems to store and process information and to help quantify levels, signals, etc. and to digitize the information for use in comparing levels.

The novel transgenic plants/roots/cells of the present disclosure are broadly directed towards transgenic roots, namely of legumes, and systems that exhibit increased nodule formation as compared to wild-type. Additionally, artificial small RNAs, identical to rhizobial-derived transfer RNA (tRNA)-derived fragments (tRFs), are provided that, when applied to and/or overexpressed in a plant, upregulate root nodule formation through repression of the plant's innate mechanisms. Methods for controlling the number of nodules on plant roots are also provided, which, in at least one embodiment, leverage the inventive transgenic roots described herein to advantageously affect crop yields.

To increase a plant's yield potential, it is important to increase the efficiencies of nodulation and nitrogen fixation. Many leguminous species can utilize atmospheric dinitrogen ($N_2$) gas to meet their needs for nitrogen through a symbiotic relationship with nitrogen-fixing rhizobial bacteria. Specifically, $N_2$ from the atmosphere is converted into ammonia ($NH_3$), which is then assimilated into amino acids, nucleotides, and other cellular constituents such as vitamins, flavones, and hormones. Their ability to fix gaseous nitrogen makes legumes an ideal agricultural organism as their requirement for nitrogen fertilizer is reduced.

The establishment of *rhizobia*-legume symbiosis is dependent on recognition of signal molecules between the partners. Upon perception of plant flavonoids, *rhizobia* synthesize and secrete lipochitin oligosaccharides, so called Nod factors (NF), which are perceived by root Nod factor receptors (NFR) to initiate rhizobial infection and formation of nodules where symbiotic nitrogen fixation (SNF) takes place. More specifically, the NFs initiate root hair curling, which begins with the very tip of the root hair curling around the bacteria, followed by the development of infection treads that provide a pathway for the bacteria to penetrate into the cortical cells of the roots to form nodules. Nodules are relatively distinct organs among plant species, essentially representing a controlled microbial invasion of the root. Similar to the human gut, the plant provides an environment in which specific microbes can thrive. The genetic control of nodulation development is complex, with the data presented herein showing a dependency on small RNAs (sRNAs) trafficked from shoot to root.

Because SNF is resource intensive, legumes have evolved a number of mechanisms, such as autoregulation of nodulation (AON) and nitrogen regulation of nodulation, to control the number of nodules formed. While fungal small RNA-mediated interaction with a plant has been previously reported, beyond this, previously little was known regarding if and/or how any bacterial sRNAs mediate biological processes in eukaryotes. Indeed, conventional thought has been that solely the host plant was in the driver's seat. The present disclosure leverages novel mechanisms identified by the present investigators through which this process is controlled by both symbiotic partners; bacteria indeed playing a role in nodule number modulation through use of bacteria-derived transfer RNA (tRNA)-derived fragments (tRFs).

tRNAs are one of the most conserved and abundant RNA species in cells; they function to decode messenger RNA (mRNA) into proteins in ribosomes. tRNAs have distinctive cloverlike structure, containing three hairpin loops, with a specific amino acid attached to the end that is used to translate codons in the mRNA to an amino acid transferred to the end of a growing protein. During the tRNA biogenesis process, or under specific conditions, cleavage yields tRFs. Indeed, tRFs are found in both prokaryotes and eukaryotes and were historically thought to be random degradation products, as they often accumulate in stressed or virally infected cells. This class of short, noncoding RNA fragments are less than about 30 nucleotide (nt) bases long (more particularly about 17 to about 22-nt), have few known functions, and a significant number of which are derived from precise processing at the 5' or 3' end of mature or precursor tRNAs.

Of particular interest is that some tRFs, akin to microRNAs (miRNAs), are bound by Argonaute (AGO) proteins, indicating that they use a miRNA-like mechanism to regulate gene expression. Different from the previously thought negative regulation of nodulation by the host, the research presented in the present disclosure establishes that tRFs are positive regulators of nodulation that repress retrotransposons through an RNA interference (RNAi)-mediated silencing pathway. As shown in FIG. 1, the symbiotic balance between SNF and the growth of the host plant via tightly controlling nodule numbers is implemented through the interconnection of both the negative and positive regulatory pathways underlying nodulation.

It is contemplated that upon identifying tRFs knocked down target genes and their functions in relation to the nodule formation in plant root, regulation of these target genes' activity by CRISPR-CAS gene editing or otherwise may generate stably transgenic plants having increased nitrogen fixation efficiency. Exemplified embodiments herein are for soybean roots, but other plants suitable for such gene regulation/CRISPR-CAS editing is contemplated provided the target gene is identified.

A recent study reported that endogenous tRFs in the stem cells of mouse were able to block reverse transcription of LTR-retrotransposons further demonstrating the role of tRFs as regulatory small RNAs through RNA interference; however, it was unclear whether tRFs can target genes prior to the presently described study. Instead, conventional studies tend to focus on miRNAs and siRNAs by filtering out tRNAs and rRNAs, whereas the present study exemplifies the importance of tRFs in cross-kingdom interaction.

Perhaps more specifically, and as described in detail below, from sRNA sequencing data, multiple tRFs were identified from the *rhizobium Bradyrhizobium japonicum*. These tRFs were then enriched in planta and used to identify 57 target genes in the soybean (*Glycine max*) genome. Three of these genes—GmRHD3, GmHAM4, and GmLRX5, which are orthologs of *Arabidopsis thaliana* genes ROOT HAIR DEFECTIVE 3 (RHD3), HAIRY MERISTEM 4 (HAM4), and LEUCINE-RICH REPEAT EXTENSIN-LIKE 5 (LRX5), respectively—are directly involved in nodule development, including that of root hairs and were studied further as representative samples. It was then determined that the tRFs produced by the bacteria are loaded into the soybean AGO1 protein, subsequently interacting with target genes in a sequence homology-dependent manner.

As shown herein, the down-regulation of the identified target host genes by rhizobial tRFs was detected from initial rhizobial infection to nodule organogenesis. Despite their relatively low abundance, some of the rhizobial tRFs were detectable in the free-living *Rhizobium* culture; thus, it is most likely that the tRFs are rapidly accumulated in the rhizobial cells upon *Rhizobia*-host interaction and migrate into host cells where they regulate host gene expression. Besides the three rhizobial tRFs investigated in detail, additional tRFs were predicted to target candidate auxin receptors and efflux carriers, RING/U-box proteins and protein kinases, which also have ties to nodulation (Table 2). Thus, the functional roles of tRFs in regulating host nodulation are much more significant and extensive than originally thought. The identification of this novel bacterial mechanism through which bacteria regulate nodule numbers in a host plant is a significant advance in the field of symbiosis biology and bacteria-eukaryote interactions.

These new discoveries allow for the transgenic modification of one or both symbiotic partners to leverage the newly discovered cross-kingdom signaling mechanisms and confer a transgenic genotype and/or phenotype to promote and increase nodule formation (as compared to wild-type). While the present disclosure focuses on leguminous plants-*Rhizobium* symbiotic partners as an experimental system, it will be appreciated that the inventive concepts hereof are not so limited and any species or strain of bacteria may be employed where such bacteria is involved in a cross-kingdom symbiotic relationship with a host organism as, based on the data provided herein, it is apparent cross-kingdom communication and/or modulation via tRFs is evolutionarily conserved.

For example, and without limitation, the compounds, principles, and methods of the present disclosure may be applicable to other host-bacterial symbiotic associations such as mammalian gut microbiota and its host (whether human, animal, or otherwise). The mammalian gut represents a complex ecosystem consisting of an extraordinary number of resident commensal bacteria existing in homeostasis with the host's immune system. Akin to the symbiotic relationship between legumes and nitrogen-fixing bacteria, the host not only tolerates such bacteria, but has evolved to require such colonization for various aspects of digestion and immune development and function. While it is conventionally known that microbiota (e.g., and without limitation, *Bacteroides thetaiotaomicron*) provides critical signals that promote maturation of immune cells and tissues leading to protection from infections by pathogens and/or contribute to non-infectious immune disorders, heretofore the exact mechanisms of such signaling have remained unknown. Based on the data provided herein, it is contemplated that the principles of tRF signaling to host genes as disclosed herein likely apply and, thus, may be leveraged similarly to described in connection with legumes and nitrogen-fixing bacteria herein.

In at least one embodiment of the present disclosure, transgenic plants, plant roots, and/or plant cells are provided that are engineered to repress or downregulate expression of one or more nodulation-associated host genes. This may be achieved through (1) genetically engineering the host plant to directly downregulate or wholly repress one or more target genes, and/or (2) repression of such genes by engineering the host plant cells/roots to produce artificial small RNAs identical rhizobial-derived tRFs (i.e. expressing one or more polynucleotide sequences encoding RNA precursor(s) for artificial small RNA fragments that are identical to tRFs derived in wild-type *Rhizobium*). Indeed, the transgenic plants/plant roots/plant cells of the present disclosure may comprise one or multiple mutations directed to encoding rhizobial-derived tRFs and/or to directly repress/downregulate target genes of the plant. As such transgenic plants, plant cells or roots have a reduction in expression of the identified target genes (i.e. through rhizobial tRF mediated miRNA-like post-transcriptional regulation and/or via direct repression or downregulation of the target gene(s) themselves), any resulting transgenic root related thereto will exhibit an increased formation of nodules as compared to wild-type.

In at least one exemplary embodiment, a leguminous plant, plant root, or plant cell is modified to express a polynucleotide construct that encodes a rhizobial-derived RNA such that artificial small RNA fragments are cleaved therefrom and produced in the plant root and/or cell. The polynucleotide construct may be configured to encode a single artificial small RNA (targeting a single host gene) or a combination of small RNAs (targeting combinations of host genes, for example, GmRHD3a/GmRHD3b or GmHAM4a/GmHAM4b). In this way, the plant itself produces artificial tRFs (which are identical to those produced by wild-type *rhizobium* upon inoculation) that downregulate the targeted host (its own) genes that are negative regulators of nodulation herein. In this manner, the transgenic leguminous plant, plant roots, or plant cells hereof are capable of producing increased numbers of nodules as compared to nodule numbers produced from corresponding wild type legume plants, plant roots, or plant cells. Importantly, the Examples below support that the resulting small RNA fragments are identical to the tRFs produced by wild-type *rhizobium* and such "artificial tRFs" operate in the host root/cells in the same fashion as do rhizobial-derived tRFs.

Additionally or alternatively, the plant, plant root, or plant cell may be modified to directly downregulate or even silence one or more genes of the plant host that is a negative regulator of nodulation (i.e. the "target genes" or "host genes"). For example, this may be achieved by selective repression of the one or more host genes (using genetic modification techniques known in the art).

Furthermore, CRISPR-Cas9 or similar methodologies may be employed to knockout or delete the targeted genes of the plant/root/cell. For example, in at least one embodiment, a CRISPR-Cas9 vector may be constructed (for example and without limitation, utilizing one or more pairs of primers selected from SEQ ID NOs: 4-9 (see Table 1)) and expressed in the host plant, plant root, or plant cell such that one or more of the targeted genes of the plant/root/cell are silenced.

The target gene(s) may comprise any of the genes listed in Tables 2 and 4 (including RHD3, HAM4, and/or LRX5). Alternatively, the target gene(s) may comprise an ortholog of the foregoing including, without limitation, the following soybean (*Glycine max*) genes used as representative target genes for the studies disclosed herein: GmRHD3a (which encodes SEQ ID NO: 80), GmRHD3b (which encodes SEQ ID NO: 81), GmHAM4a (which encodes SEQ ID NO: 82), GmHAM4b (which encodes SEQ ID NO: 83), and GmLRX5 (which encodes SEQ ID NO: 84). As shown herein, these genes are targeted by certain tRFs and, while conventionally their function was unknown, the present disclosure establishes that they are, in fact, negative regulators of legume nodulation. In at least one exemplary embodiment, the targeted gene(s) comprises one or more of the following genes or gene combinations: GmRHD3a (which encodes SEQ ID NO: 80), GmRHD3b (which encodes SEQ ID NO: 81), GmRHD3a GmRHD3b, GmHAM4a (which encodes SEQ ID NO: 82), GmHAM4b (which encodes SEQ ID NO: 83), GmHAM4a GmHAM4b, GmLRX5 (which encodes SEQ ID NO: 84).

In at least one embodiment, a transgenic plant/plant root/cell may comprise a first mutation at both GmRHD3a and GmRHD3b (i.e. downregulating both genes) and a second mutation at GmLRX5. As noted above, this may be in addition to, or in lieu of, a further mutation that causes the plant/root/cell to express one or more polynucleotide sequences encoding the RNA precursor(s) for rhizobial-derived tRFs. Indeed, it will be understood by one of skill in the art that any combination of the host gene negative regulators of nodulation may be targeted for repression/downregulation, with or without any combination of expression of rhizobial-derived tRFs.

Methods of transforming cells with polynucleotide sequences, vectors, or expression cassettes that encode such compounds are well known to those skilled in the art, as are methods for selectively amplifying or repressing a host gene. Plants, plant roots, and plant cells may be transformed by, for example, electroporation, *Agrobacterium* transformation, engineered plant virus replicons, electrophoresis, microinjection, micro-projectile bombardment, micro-LASER beam-induced perforation of cell wall, or simply by incubation with or without polyethylene glycol (PEG).

Figure 2:
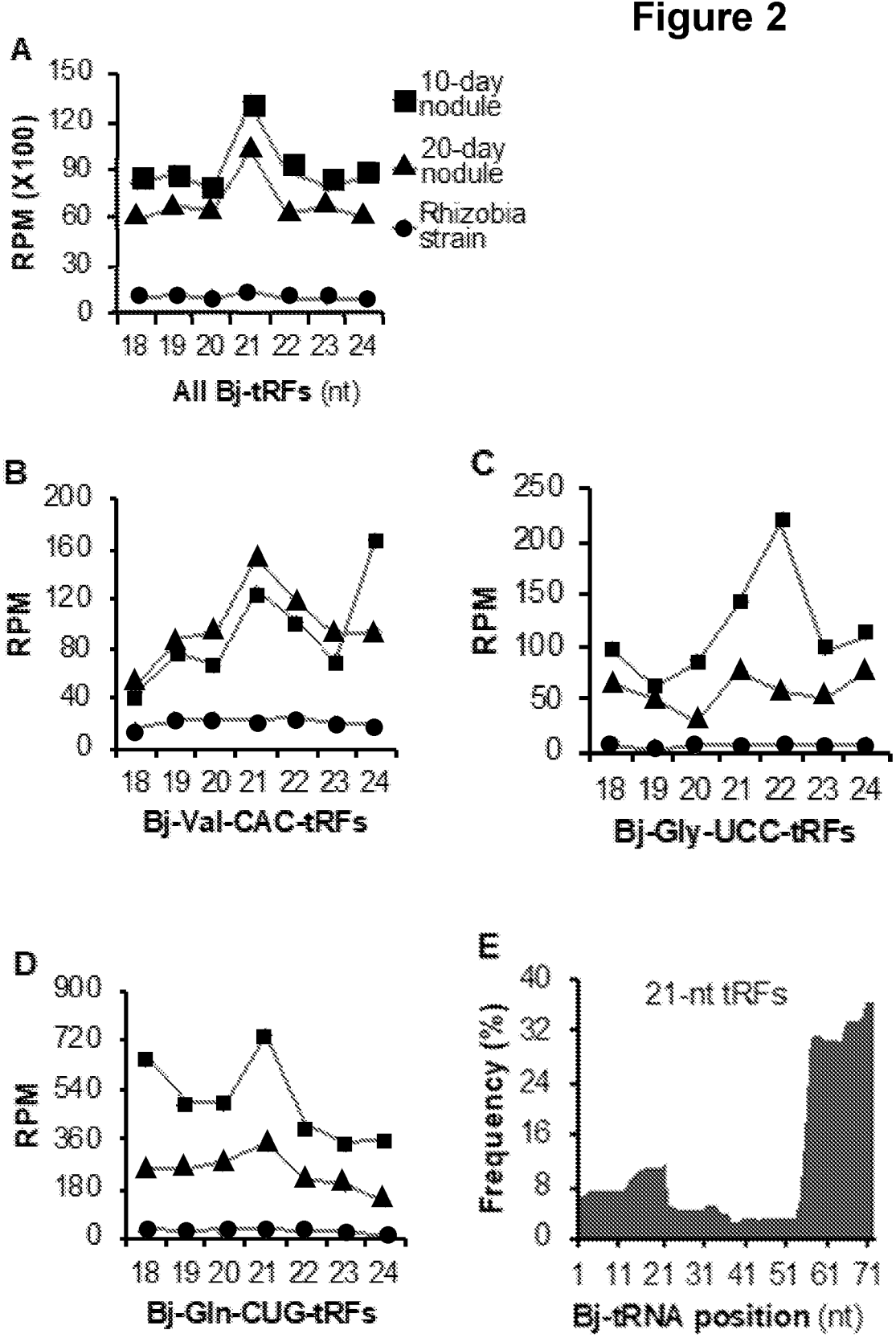
FIG. 2 illustrates graphical data relating to the sizes, positions, and abundance of rhizobial tRFs in Rhizobia and root nodules, with subparts A-D representing data on size distribution and relative abundance of rhizobial tRFs in free-living Rhizobia (strain USDA 110) (●), and soybean root nodules induced by USDA 110 (■ and ▲), subparts E-H representing data on the positions and abundance of 21-nt tRFs along rhizobial tRNAs in soybean root nodules induced by USDA 110, with the frequencies reflecting the relative coverage of each site along individual tRNAs by 21-nt tRFs, and subparts I-K illustrating the structures of three wild-type rhizobial tRNAs arranged in a hairpin structure and the physical positions of three tRFs as indicated between the black lines (Bj-tRF001/SEQ ID NO: 1, Bj-tRF002/SEQ ID NO: 2, and Bj-tRF003/SEQ ID NO: 3, respectively) produced by corresponding tRNAs, with subpart I having SEQ ID NO: 71, subpart J having SEQ ID NO: 72, and subpart K having SEQ ID NO: 73.
Figure 2:
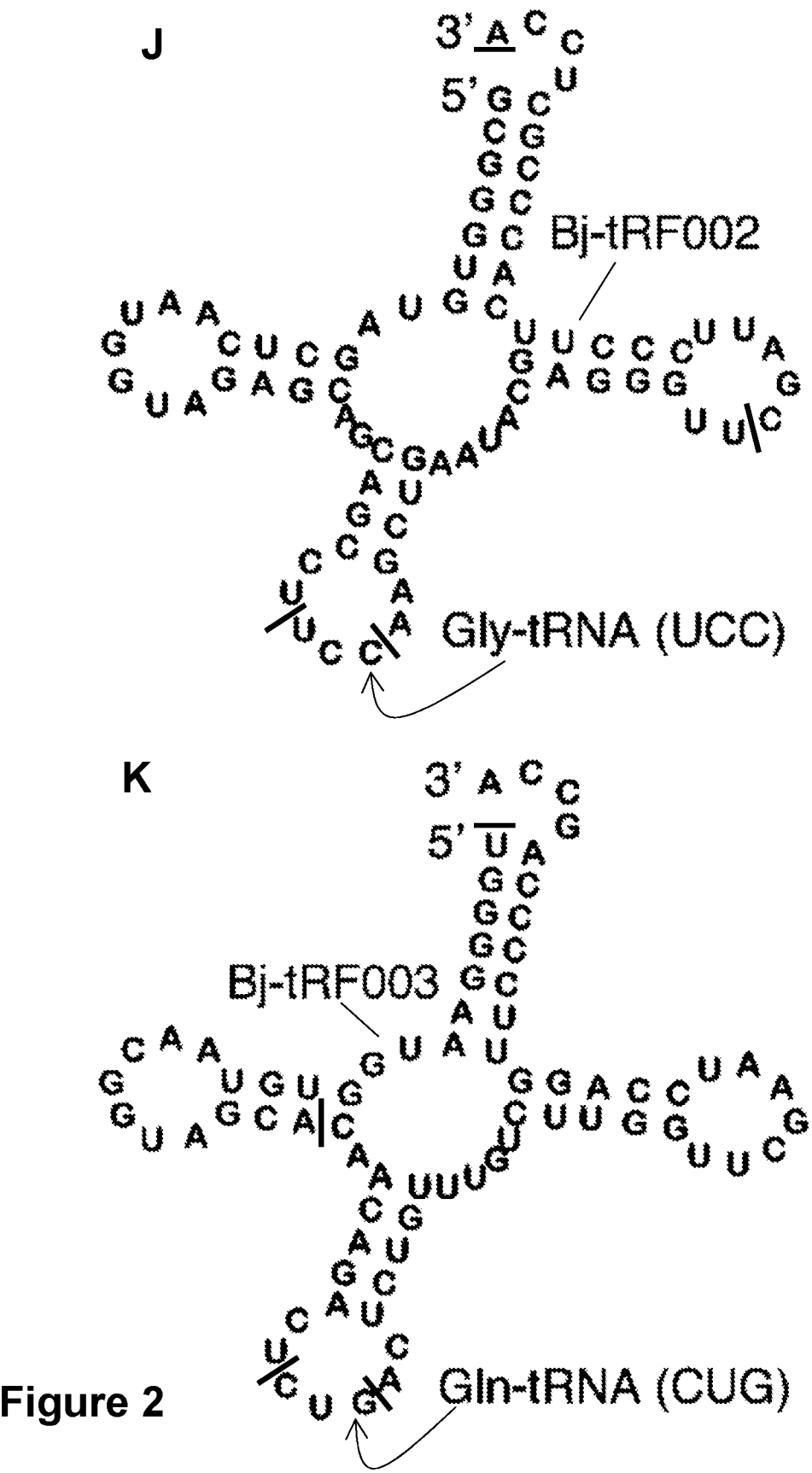

The tRFs of the present disclosure may be any tRFs that target and silence or downregulate targeted host genes through an RNAi-mediated silencing pathway in a host root nodule that inhibits nodule formation (i.e. a host negative regulator of nodulation). As such, amplification of the tRF abundance in the root nodule inhibits the plant's nodulation repression mechanism and, thus, drives increased nodule formation. In at least one embodiment, the tRFs hereof comprise any tRF listed in Tables 2 and 4 (below) or others that are otherwise capable of downregulating expression of plant host genes that are negative regulators of nodulation. Accordingly, the polynucleotide constructs described herein may comprise any of the sequences related to such tRFs. In exemplary embodiments, however, the tRFs comprise one or more of the predominant tRF products derived from three tRNAs: Val-1-tRNA(CAC), Gly-1-tRNA(UCC), and Gln-1-tRNA(CUG) (termed Bj-tRF001 (SEQ ID NO: 1), Bj-tRF002 (SEQ ID NO: 2), and Bj-tRF003 (SEQ ID NO: 3), respectively and as identified in FIG. 2, subparts I-K). Accordingly, the polynucleotide construct may comprise SEQ ID NO: 1-3, or a substantially homologous nucleic acid sequence of SEQ ID NO: 1-3.

Figure 14A:
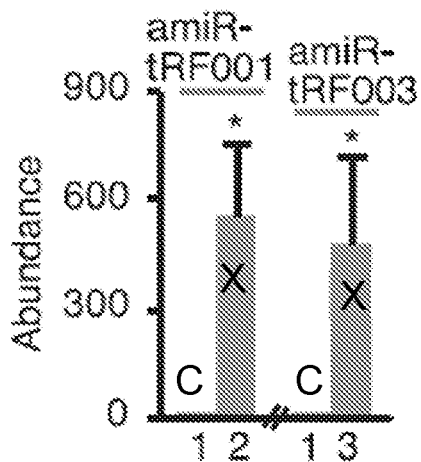
FIGS. 14A-14C show graphical data related to rhizobial tRF-guided gene regulation by hijacking the host RNAi machinery, with FIG. 14A illustrating data related to the abundance of artificial miRNAs measured with stem-loop qRT-PCR in aMIR-tRF001 (2) and aMIR-tRF003 (3) transgenic roots and respective empty-vector transgenic roots (1) at 28 dpi, FIG. 14B showing expression of the identified tRF/artificial miRNA targets measured with qRT-PCR in the same samples as shown in FIG. 14A (values in both FIGS. 14A and 14B, with one set as "1" and the others adjusted accordingly, shown as means±SE from three biological replicates and asterisks denoting the significance level at $P<0.01$ (Student's t test), and FIG. 14C showing box and whisker plots indicative of nodule numbers in the same samples as described in FIG. 14A, with all data points represented by dots, displaying 95 to 5% interval from three biological replicates (12 plants per replicate)

For example and without limitation, such polynucleotide constructs may encode the identified sequences, as well as the complementary sequences thereto, to produce the precursor RNA having a hairpin structure from which artificial small RNAs that are identical to rhizobial-derived tRFs are ultimately cleaved. FIG. 14D illustrates at least one exemplary embodiment of such a precursor RNA prepared pursuant to the present disclosure using a construct encoding SEQ ID NO. 1 and its complementary sequence* (left) and SEQ ID NO. 3 and its complementary sequence* (right). The RNA resulting therefrom is subsequently cleaved in planta to produce the desired artificial small RNAs which are identical to wild-type rhizobial-derived tRFs.

While specific polynucleotide sequences are provided, it will be apparent to one of ordinary skill in the art, that the disclosed artificial tRFs and/or their RNA precursors may be encoded by multiple polynucleotide sequences because of the redundancy of the genetic code. It is well within the skill of a person trained in the art to create these alternative RNA and DNA sequences that have amino acid substitutions, deletions, additions or insertions that do not materially affect biological activity of the artificial tRFs of the invention (namely, those capable of cross-kingdom communication and that initiate nodulation in plant roots). Fragments of the artificial tRFs that retain the ability to induce nodulation are also included in this definition. The polynucleotides of the present disclosure may include vectors and expression cassettes. The vectors and expression cassettes may contain transcriptional control sequences that are operably linked to polynucleotide sequences encoding the precursor RNAs and related artificial tRFs hereof.

Other embodiments of the present disclosure include genetically engineered bacterial microorganisms having upregulated production of one or more tRFs as compared to a corresponding wild-type bacterial microorganism. In at least one embodiment of the present disclosure, a species or strain of bacteria is provided that is engineered to exhibit upregulated expression of one or more tRFs as compared to such production in a wild-type of the corresponding species or strain. The one or more amplified tRFs may be any tRFs capable of cross-kingdom communication and/or signaling with at least one target gene of host organism.

For example, and without limitation, the rhizobial microorganism may express a polynucleotide construct that enhances the microorganism's production of one or more tRFs such as those identified in Tables 2 and 4 of the present disclosure. The polynucleotide construct may be configured to upregulate expression of a single tRF (targeting a single host gene) or a combination of tRFs (targeting combinations of host genes, for example, GmRHD3a/GmRHD3b or GmHAM4a/GmHAM4b).

In at least one exemplary embodiment, the host organism is a leguminous plant, plant root, or plant cell, such as a soybean (e.g., *Glycine max*) and may comprise the transgenic leguminous plants, plant roots, or plant cells previously described or a wild-type leguminous plant. In any event, the bacterial-derived tRFs are capable of repressing or downregulating expression of at least one gene target in the host organism's nodules. There, the one or more tRFs may be, for example, tRFs that target and silence or repress a target host through an RNAi-mediated silencing pathway in the root nodule designed to inhibit nodule formation.

Where the host organism is a leguminous plant, the bacterial microorganism may be of any strain or species of nitrogen-fixing bacteria such as, for example and without limitation, a rhizobial microorganism such as a species or strain of *B. japonicum* USDA 110. Other non-limiting examples of such rhizobial microorganisms include other *B. japonicum* strains (e.g., such as USDA 123 and 138), *Rhizobium etli, Sinorhizobium meliloti, Rhizobium leguminosarum, Parasponia rhizobium, Mesorhizobium loti,* and other compatible *rhizobium* species.

Compounds comprising one or more species or strains of the bacterial microorganisms hereof are also disclosed. In at least one embodiment, the compound is formulated in an inoculant composition comprising the engineered bacterial microorganism as heretofore described. The compound may comprise a single species/strain of the engineered bacterial microorganisms of the present disclosure or a combination of different species and/or strains of bacterial microorganisms in the compound. Engineered bacteria may additionally be combined with wild-type bacteria strains or species, or all bacteria within the compound may be genetically modified (with the same or different mutations) to amplify expression of one or more tRFs as described herein.

The inoculant composition may comprise a carrier or additive. The carrier or additive used will depend on the nature of the inoculant composition. For example, the inoculant composition may be in the form of a liquid composition, a solid composition (such as a powder, pellet or granular composition), a seed coating, or in any other form suitable for the desired application. In at least one embodiment, the inoculant composition comprises a liquid composition and includes a solvent suitable for dissolving or suspending the compound.

The inoculant compositions of the present disclosure may be adapted for application to a leguminous plant, plant root or cell in any suitable way. For example, the inoculant composition could be adapted to be applied as a seed coating, applied as a solid or liquid composition to the foliage or roots of a plant, or applied as a solid or liquid composition to the soil before, during or after sowing of a leguminous plant. A range of useful carriers or additives would be readily apparent to those of skill in the art and may include, for example: one or more gums (including xanthan gum), clay or peat based carriers, one or more nutrients including carbon or nitrogen sources, one or more antifungal or antibacterial agents, one or more seed coating agents, one or more wetting agents and the like.

Methods of increasing nodulation activity in leguminous plant roots may be practiced in transgenic plants/plant roots/plant cells that are engineered to repress or downregulate the identified target genes and in non-transgenic plants to which the engineered bacterial microorganisms and/or inoculants are applied. Further, methods are also provided that utilize both approaches concurrently—i.e. application of the engineered bacterial microorganisms having amplified tRF production and/or inoculants to the transgenic plants/plant roots/plant cells of the present disclosure.

In at least one embodiment, such a method comprises repressing or downregulating expression of one or more target genes of a host plant root or cell, and inoculating, or having inoculated, the modified plant host root or cell with at least one *rhizobium* to initiate nodulation. The inoculating step may be performed pursuant to known methodologies and using conventional microorganism species and strains. In one embodiment, the roots may be wounded to enable the bacterial cells to penetrate the roots more quickly and easily; however, wounding of the roots is not required.

The target gene(s) may comprise any of the target genes described herein and, in at least one exemplary embodiment, comprise RHD3, HAM4, LRX5, an ortholog of RHD3, an ortholog of HAM4, and/or an ortholog of LRX5. Perhaps more specifically, and in yet another exemplary embodiment where the leguminous plant root is *Glycine max*, each host gene may comprise GmRHD3a (which encodes SEQ ID NO: 80), GmRHD3b (which encodes SEQ ID NO: 81), GmHAM4a (which encodes SEQ ID NO: 82), GmHAM4b (which encodes SEQ ID NO: 83), or GmLRX5 (which encodes SEQ ID NO: 84).

The species or strains of the at least one *rhizobium* can likewise comprise any microorganism that initiates nodulation in a host plant root or cell including, for example, *Bradyrhizobium japonicum, Rhizobium etli, Sinorhizobium meliloti, Rhizobium leguminosarum, Parasponia rhizobium, Mesorhizobium loti* and the like.

The step of downregulating or repressing expression of the one or more target genes of the host plant root or cell may comprise introducing and expressing a first polynucleotide construct that encodes a rhizobial-derived RNA that is the precursor for producing one or more artificial tRFs in the plant root as previously described. In at least one exemplary embodiment, the RNA may have a hairpin structure as shown in FIG. 14D. The first polynucleotide construct may encode one or more of SEQ ID NOs. 1-3, 34-70, or any substantially homologous nucleic acid sequence to any of the foregoing. Further, the first construct may also encode a complementary sequence to the aforementioned (similar to as seen in FIG. 14D as associated with the resulting hairpin structure).

Additionally or alternatively, downregulating or repressing expression of the one or more target genes of the host plant root or cell may comprise constructing a CRISPR-Cas9 vector as described herein and expressing the vector in the host plant root or cell, where such vector is designed to silence one or more of the target host genes identified herein. In at least one exemplary embodiment, the CRISPR vector may be designed to silence one or more of the following: GmRHD3a, GmRHD3b, GmRHD3a GmRHD3b, GmHAM4a, GmHAM4b, GmHAM4a GmHAM4b, and GmLRX5.

Still further, rather than silencing a host gene via the CRISPR-Cas9 methodology, the step of downregulating or repressing expression of the one or more target genes of the host plant root or cell may comprise repressing expression of one or more of the targeted host genes. Such repressed expression can be achieved through any suitable methodology now or hereinafter known in the art and, in at least one embodiment may comprise expressing a polynucleotide construct in the host root or cell that encodes a transcription factor for downregulating or repressing expression of the one or more host genes. Furthermore, such a method may involve application of the compounds and/or compositions having the engineered bacterial microorganisms directly to the transgenic roots or the roots of the transgenic plants, plant roots, or plant cells described herein. In one embodiment, the roots may be wounded to enable the bacterial cells to penetrate the roots more quickly and easily; however, wounding of the roots is not required.

Due to the confirmed ability of the inventive compounds, plants/roots/cells, and methods of the present disclosure to increase nodule formation in leguminous plants, application of the concepts set forth herein can significantly reduce the use of nitrogen-based fertilizers, cutting down the economic and environmental cost of agriculture, without diminishing yield. The present disclosure is further described with reference to the following non-limiting examples.

Materials and Methods

For the examples described herein, the following materials and methods were used.

Plant and *Rhizobium* Materials

Soybean (*Glycine max*) cultivar Williams 8 were grown in a greenhouse under 16 h light/8 h dark period for RNA isolation and hairy root transformation, and root and nodule tissue collection. Williams 82 was also used for preparation of protoplasts from soybean roots. *Bradyrhizobium japonicum* strain USDA110 was cultured in a modified arabinose gluconate (MAG) medium composed of 1.3 g HEPES, 1.1 g MES, 1 g yeast extract, 1 g L-arabinose, 1 g D-gluconic acid sodium salt, 0.22 g $KH_2PO_4$, and 0.25 g $Na_2SO_4$ per liter, pH 6.6, and used for soybean root inoculation.

Soybean seeds were germinated in sterilized vermiculite sand mixture (3:1) for 7 days before inoculation with the *Rhizobium* culture or treatment with the MAG medium without the *Rhizobia* (control sets). The largest nodules on inoculated roots 10 days and 20 days post inoculation (DPI or dpi) and uninoculated roots at the same stages were collected for RNA isolation. Root hair cells were isolated from the roots following a protocol set forth in Lin et al., Molecular response to the pathogen *Phytophthora sojae* among ten soybean near isogenic lines revealed by comparative transcriptomics, BMC Genomics, 15: 18 (2014).

DNA and RNA Isolation, PCR, and Sequencing

Genomic DNA isolation, polymerase chain reaction (PCR), reverse transcription-PCR (RT-PCR), quantitative RT-PCR (qRT-PCR), and sequencing of DNA fragments was performed as previously described in Ping et al., Dt2 is a gain-of-function MADS-domain factor gene that specifies semideterminacy in soybean, Plant Cell, 26: 2831-2842 (2014). In qRT-PCR, the soybean gene GmELF1b (Glyma.02G276600) or GmCons4 (Glyma.12g020500) was used as an internal reference to quantify the relative expression levels of the rhizobial tRF targets identified using three biological replicates.

Stem-loop RT-PCR was performed to evaluate relative abundance of rhizobial tRFs. The specificity of stem-loop RT-PCR for individual tRFs was confirmed by sequencing of the amplified fragments. The b11631 gene in *B. japonicum* USDA 110 was used as an internal reference to quantify the relative abundance of tRFs determined by stem-loop RT-PCR using three biological replicates. The primers used for the varieties of PCR and sequencing of amplified fragments were developed using strategies and techniques known in the art and are listed in the Supplemental Materials of the article Ren et al., Rhizobial tRNA-derived small RNAs are signal molecules regulating plant modulation, Science 365, 919-922 (2019) (including all Supplemental Materials related thereto, the "Ren et al. Article")), the entirety of which is incorporated herein by reference, with the specific primers used for CRISPR-Cas9 and amplification studies listed in Table 1.

TABLE 1

Primers used with CRISPR-Cas9 and amplification studies.

| Primers | Sequence (5'-3') | Purpose |
| --- | --- | --- |
| RHD3_pSC_F | SEQ ID NO: 4 | CRISPR-Cas9 construction |
| RHD3_pSC_B | SEQ ID NO: 5 | CRISPR-Cas9 construction |
| HAM4_pSC_F | SEQ ID NO: 6 | CRISPR-Cas9 construction |
| HAM4_pSC_B | SEQ ID NO: 7 | CRISPR-Cas9 construction |
| LRX5_pSC-F | SEQ ID NO: 8 | CRISPR-Cas9 construction |
| LRX5_pSC-B | SEQ ID NO: 9 | CRISPR-Cas9 construction |
| RHD3b_CDS_F | SEQ ID NO: 74 | overexpression construction |
| RHD3b_CDS_B | SEQ ID NO: 75 | overexpression construction |
| HAM4a_CDS_F | SEQ ID NO: 76 | overexpression construction |
| HAM4a_CDS_B | SEQ ID NO: 77 | overexpression construction |
| LRX5_CDS_F | SEQ ID NO: 78 | overexpression construction |
| LRX5_CDS_B | SEQ ID NO: 79 | overexpression construction | sRNA-Seq and mRNA-Seq & Data Analyses

Total NRAs from plant roots, root nodules, and *Rhizobia* were isolated using TRIzol Reagent (Invitrogen/Life Technologies, CA). The small RNA-seq (sRNA-seq) and mRNA libraries were constructed using the TruSeq small-RNA kit and TruSeq Stranded mRNA kit (Illumina, CA), respectively, according to the manufacturer's protocol, and sequenced using HiSeq2500 (Illumina, CA) at the Purdue Genomics Core Facility (West Lafayette, IN).

Raw sRNA-seq data were processed with the FASTQ/A short-reads pre-processing tools, FASTX-Toolkit, for removal of adapter sequences and low-quality reads. The processed reads longer than 16 nt were compared with the soybean reference genome sequence (Version 2, Phytozome) and the soybean chloroplast and mitochondria sequences using Bowtie (version 1.0.0) with a parameter of "-v 0." The reads unmapped to these soybean sequences were subsequently compared with the *B. japonicum* USDA110 reference genome sequence using Bowtie. The reads perfectly mapped to the USDA110 genome sequence without any mismatches were further annotated and those perfectly matching transfer RNA (tRNA) sequences of USDA 110 were considered as rhizobial tRNA derived fragments (tRFs). Relative abundance of unique rhizobial tRFs in each library were normalized to counts per million reads (CPM). Unique rhizobial tRFs (Bj-tRFs) with a relative abundance higher than 100 CPM in at least one of the nodule sRNA-seq libraries were used to identify soybean gene targets of rhizobial tRFs.

Raw mRNA-seq data were also processed with the FASTX-Toolkit for removal of adapter sequences and low-quality reads. The processed reads from each library were mapped to the soybean reference genome (Version 2, Phytozome) using TopHat2 mapping tool (version 2.1.1), with a parameter that allowed for one mismatch per read. Relative expression level of an individual soybean gene was determined based on the number of reads uniquely mapped to corresponding genes using the BEDTools software (version 2.27.1). Differentially expressed genes (DEGs) between compared samples were defined using "edgeR" (version 3.22.5), with an adjusted false discovery rate (FDR)-controlled q-value<0.05. A subset of DEGs was further validated by qRT-PCR.

Sequence Alignment and Phylogenetic Analysis

Sequence alignment and construction of a Neighbor-Joining phylogenetic tree were performed using a procedure described in Niu et al., Expression of artificial microRNAs in transgenic *Arabidopsis thaliana* confers virus resistance, Nat. Biotechnol., 24: 1420-1428 (2006). The tree was visualized using Evolview, an online visualization tool for phylogenetic trees (version 2).

tRF Target Gene Prediction and Target Site Validation psRNA Target, a plant small RNA target analysis server, was used to predict the target genes of rhizobial tRFs. A predicted tRF target was considered as a strong candidate when the expectation value determined by the server was no more than 3 and when the candidate gene exhibited differential expression between the root and nodule samples. 5' RNA ligase mediated rapid amplification of cDNA ends (RLM-RACE) was performed to identify cleavage sites of mRNAs from the rhizobial tRF targets using the Gene Racer RLM-RACE Kit (Invitrogen, MA) according to the manufacturer's protocol. The cDNA samples were amplified by nested PCR. The PCR products were cloned into the pGEM-T easy vector (Promega, WI) and 40 clones for each target site were sequenced at Purdue Genomics Core Facility (West Lafayette, IN) to determine the cleavage site(s) in the transcripts of the tRF target(s).

Plasmid Construction and Soybean Hairy Root Transformation

Figure 7A:
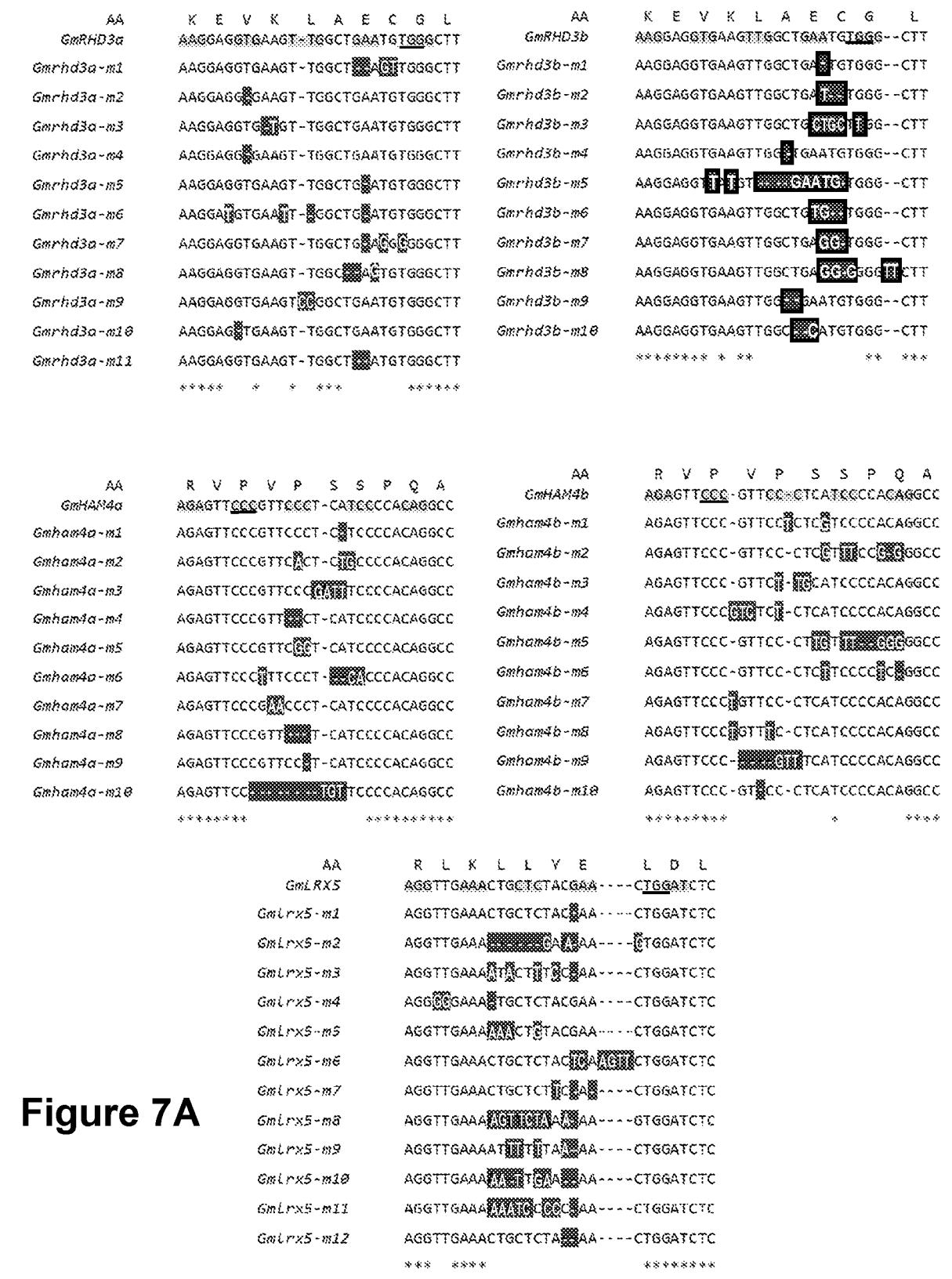
Figure 7B:
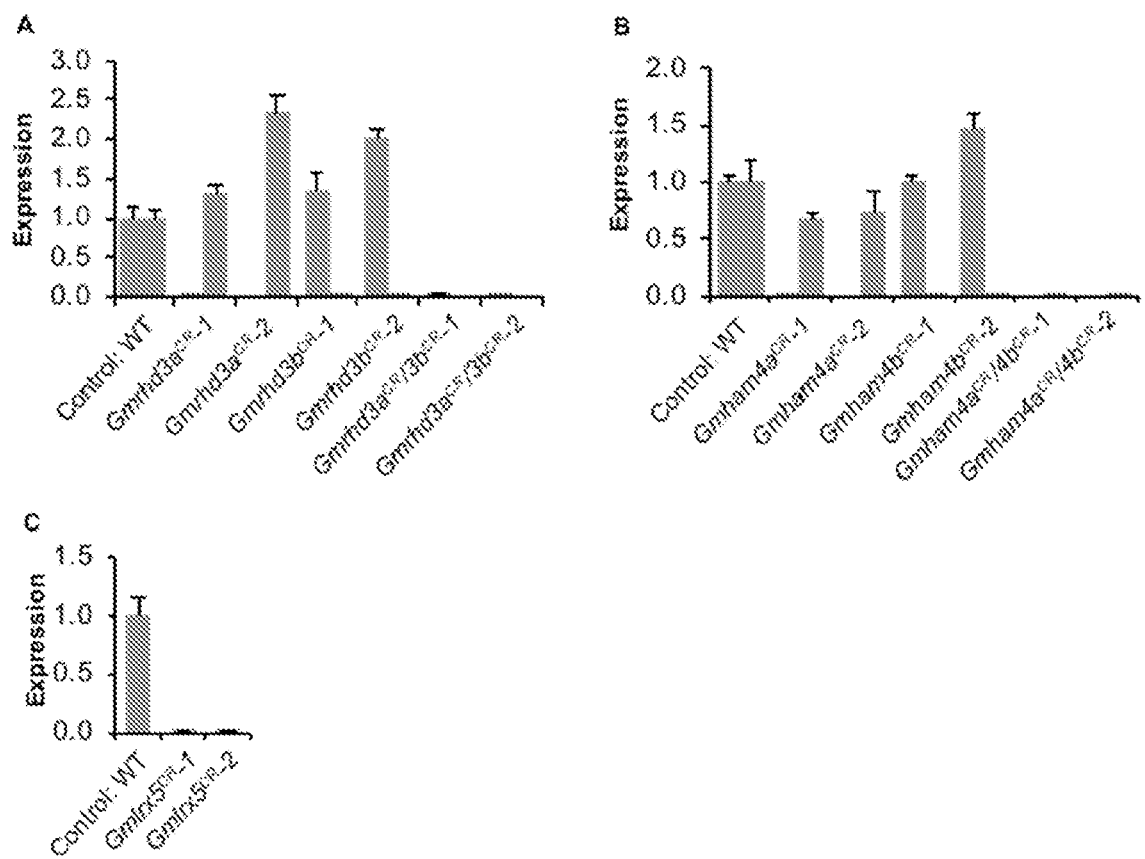
FIG. 7B, subparts A-C show graphical depictions of the rhizobial tRF targets and the CRISPR-Cas9-edited forms of the targets from FIG. 7A in the transgenic roots, with the expression levels of the wild-type (WT) tRF targets and CRISPR-Cas9-edited forms of the targets shown relative to that of GmELF1b detected by qRT-PCR and shown as means±s.e. from three technical replicates, the transgenic root samples being the same as described in FIG. 8A, which were collected 28 dpi, controls being transgenic roots of empty vectors used for developing the CRISPR-Cas9 knockouts, and, in each panel, the expression level of one sample set as 1, and those of the others adjusted accordingly ("−1" and "−2" indicate two hairy roots with the same gene or a pair of duplicated genes edited by CRISR-Cas9 using a same guide RNA, each with three technical replicates.

The pSC1 vector was used to develop gRNA-Cas9 expression vectors following a protocol described in Rueden et al., ImageJ2: ImageJ for the next generation of scientific image data," BMC Bioinformatics, 18: 529 (2017). sgRNAs for editing the five soybean genes GmRHD3a 3b, GmHAM4a 4b, and GmLRX5 were designed using CRISPR-P, a web-based guided RNA design tool. The primer pairs used for this study were annealed (95° C. for 5 min and then cool down to room temperature) to form dimers, and then integrated into the Lgu I-digested pSC1 vector, separately. The sgRNAs targets exons of the genes as shown in FIG. 7.

The pBIN438 vector was used to develop the overexpression constructs under the control of a cauliflower mosaic virus 35S promoter for soybean genes GmRHD3b, GmHAM4a, and GmLRX5. The GmRHD3b and GmLRX5 coding sequences (CDS) were amplified by the primers listed on Table 1, respectively, and then integrated into pBIN438 using the Sal I/Xba I enzymes, and the GmHAM4a CDS was inserted into pBIN438 using the Xho I Kpn I enzymes.

The pEGAD vector was used to develop three STTM constructs, each silencing a rhizobial tRF in soybean hairy roots. Individual STTM modules were designed based on the three 21-nt rhizobial tRFs. The primer pairs containing the STTM nodules were annealed to dimers, and then integrated separately into pEGAD using the Age I Bam HI enzymes. All primers used for plasmid construction are listed in the Ren et al. Article.

Soybean hairy root transformation was performed as previously described with minor modification. Hypocotyls of one-week-old soybean seedlings were injected with Agrobacterium rhizogenes K599 and kept at high humidity (>90%) with plastic lids until hairy roots at the injection sites were developed to 5-10 cm long. The original seedling main roots were then cut and the hairy roots were immersed in water for about five days before the plants with hairy roots were transferred into the pots with sterilized vermiculite and sand mixture (3:1). Two days after the plant transfer into pots, the plant roots were inoculated with the B. japonicum strain USDA110 (20 mL suspension (OD=0.05) per pot). Transgenic roots were identified by PCR of unique sequences from respective plasmid constructs and further validated by sequencing of PCR fragments. CRISPR-Cas9 induced knockout hairy roots were identified by sequencing of amplified gene fragments harboring the target sites of the designed guided RNAs that were cloned into the pGEM-T easy vector (Promega, WI). Only hairy roots with both alleles mutated at the target sites were considered as knockout hairy roots for phenotyping studies.

Phenotyping of Root Nodule Numbers

Nodules on transgenic hairy roots and the controls were counted 28 dpi. Approximately one-cm root segments in root hair zone of the six dpi-hairy roots were cut and washed with distilled deionized water and then fixed with ethanol: acetic acid (3:1) for two hours. The fixed roots were examined for root hair morphology including deformation and welling tips or wavy growth and curling (formation of infection foci), and root hair numbers and length, and were photographed with a Nikon Eclipse Ti2 microscope (Nikon, NY).

Example 1

Verification of Cross-Kingdom Communication

To address if tRFs are involved in cross-kingdom communications, soybean-Rhizobium symbiotic partners were used as an experimental system. In particular, the soybean (Glycine max) and the rhizobium (Bradyrhizobium japonicum) were studied as symbiotic partners. Given the lack of AGO-modified RNAi machinery in bacteria, the intent was to identify tRFs derived from rhizobial tRNAs that regulate soybean genes. Small RNAs and mRNAs from B. japonicum strain USDA110, 10-day and 20-day old soybean (cv., Williams 82) nodules induced by USDA110, and uninoculated Williams 82 roots were isolated and sequenced using the protocols described above, and putative tRFs produced by Rhizobia either in the Rhizobium culture or in the Rhizobia-induced nodules were identified.

Figure 3A:
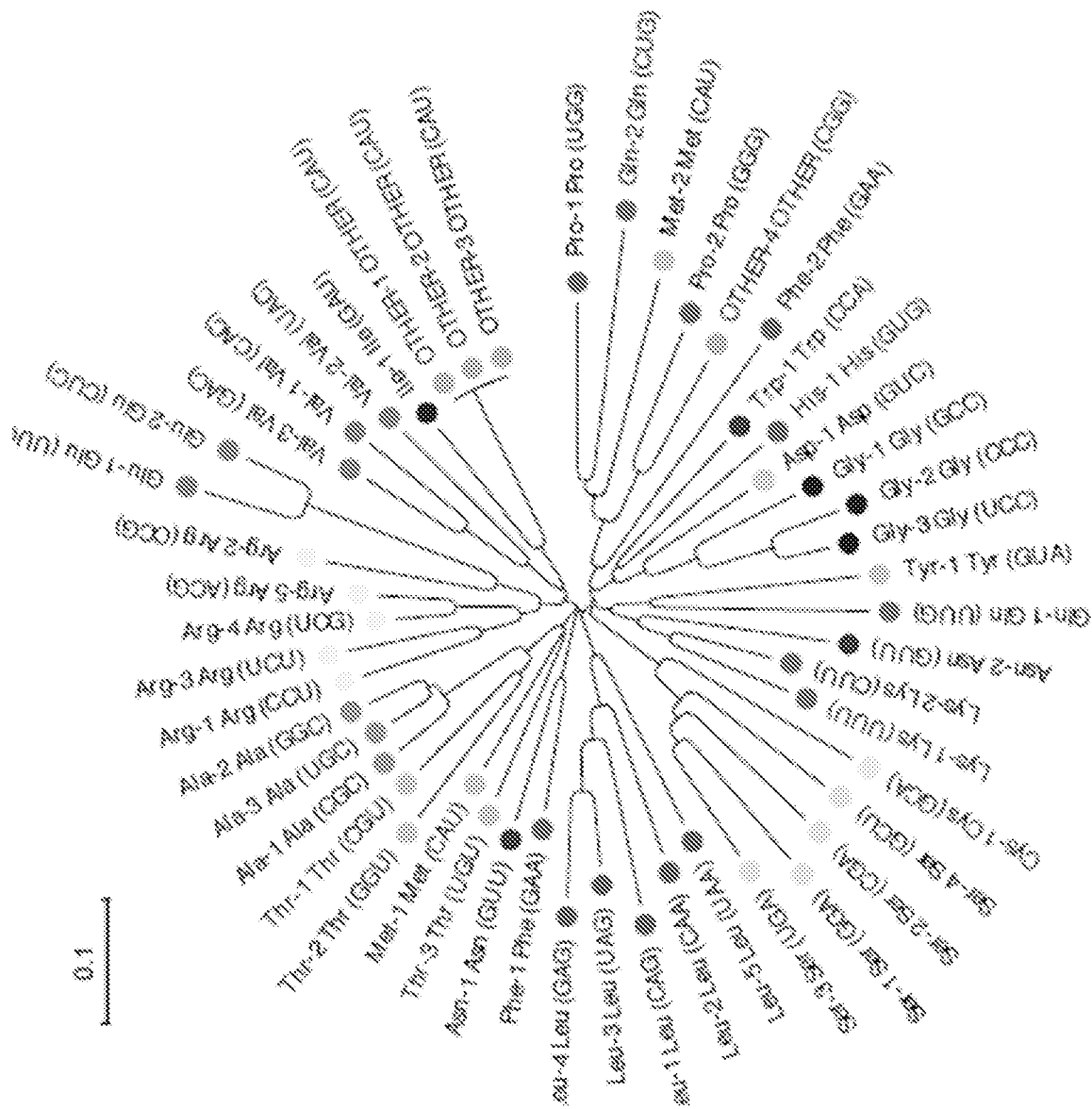
FIG. 3A is a neighbor-joining tree representation of the phylogenic relationship of tRNAs in the *Bradyrhizobium japonicum* genome strain USDA110k prepared based on the tRNA sequences (each named in a format of "Bj (Abbreviation of the *rhizobium* species)"–"amino acid transferred by a particular tRNA copy"–"order of tRNA transferring a same amino acid by recognizing multiple codons"–"(condo)"), with the numbers adjacent to nodes indicating the bootstrap values from the test of 1000 replicates.
Figure 3B:
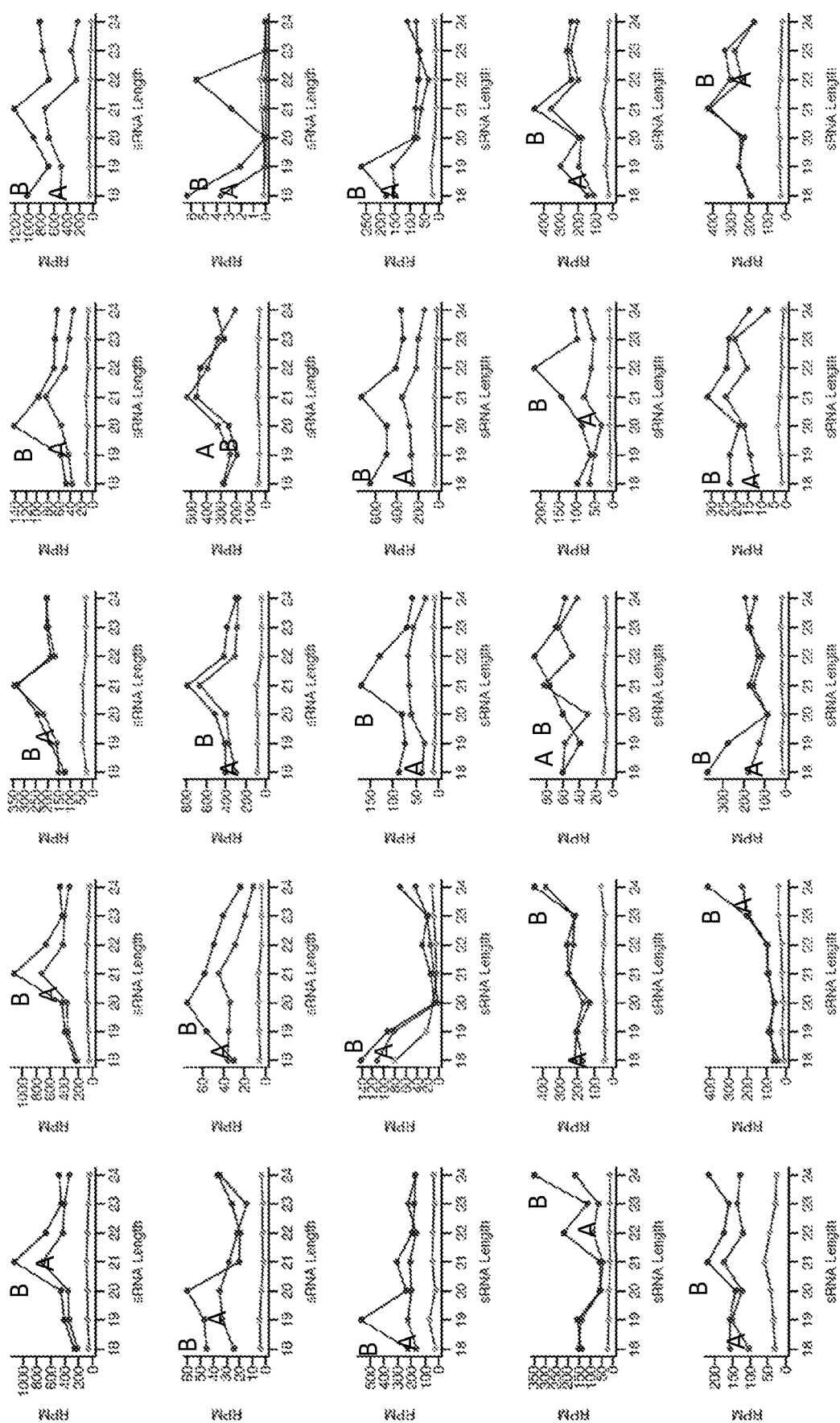
FIGS. 3B and 3C illustrate graphical data relating to the size distribution and abundance of rhizobial tRFs in Rhizobia and root nodules, with the x-axis indicating the size of major rhizobial tRFs that range from 18-24 nt and the y-axis indicating the relative abundance of the tRFs of different sizes; lower plot line in all cases represents size distribution and relative abundance of rhizobial tRFs in free-living *rhizobia* (strain USDA110), whereas the plot lines labeled A and B represent size distribution and relative abundance of rhizobial tRFs in soybean 10-dpi nodules and 20-dpi nodules, respectively.
Figure 3C:
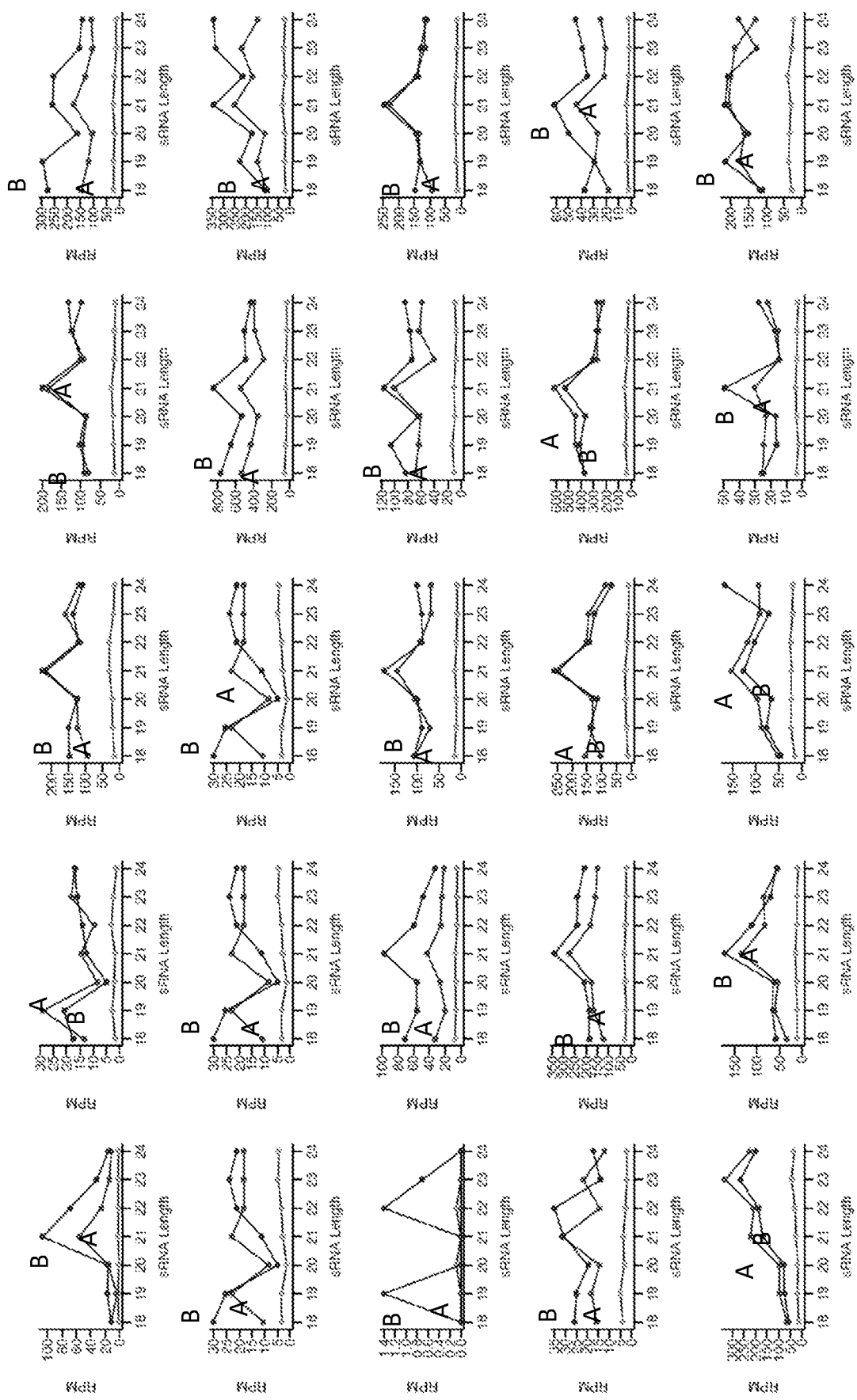
Figure 4A:
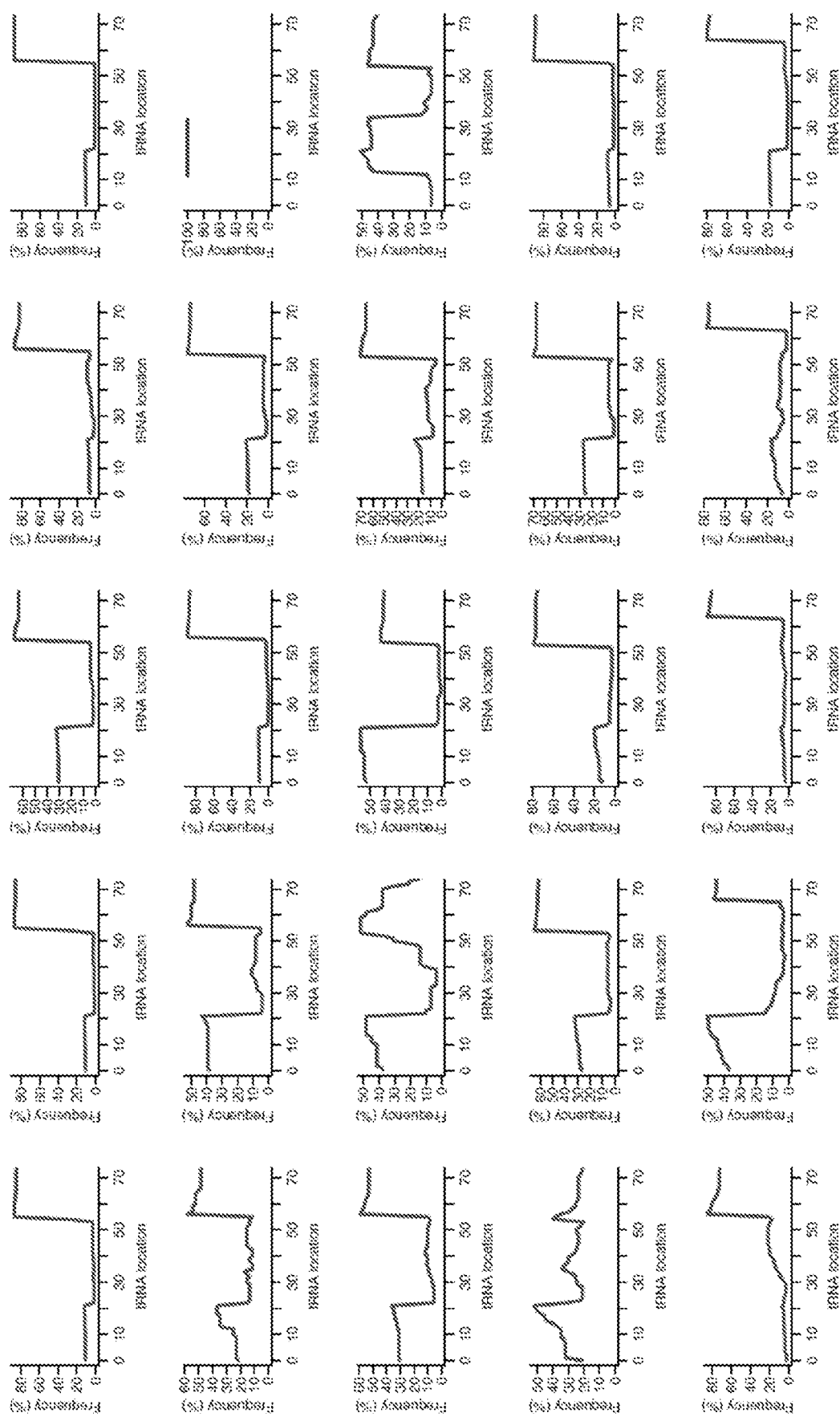
FIGS. 4A and 4B show data related to the physical positions and abundance of 21-nt tRFs along rhizobial tRNAs in soybean root nodules where the 10-dpi and 20-dpi nodules were induced by USDA 110 and the frequencies shown reflect the relative coverage of each site along individual tRNAs by the 21-nt tRFs, with each x-axis representing nucleotide locations of a tRNA in *B. japonicum* USDA110 and each y-axis indicating the frequencies of individual nucleotides along the tRNA that are covered by the 21-nt tRFs derived from the tRNA in the 10-dpi or 20-dpi nodules induced by USDA110.
Figure 4B:
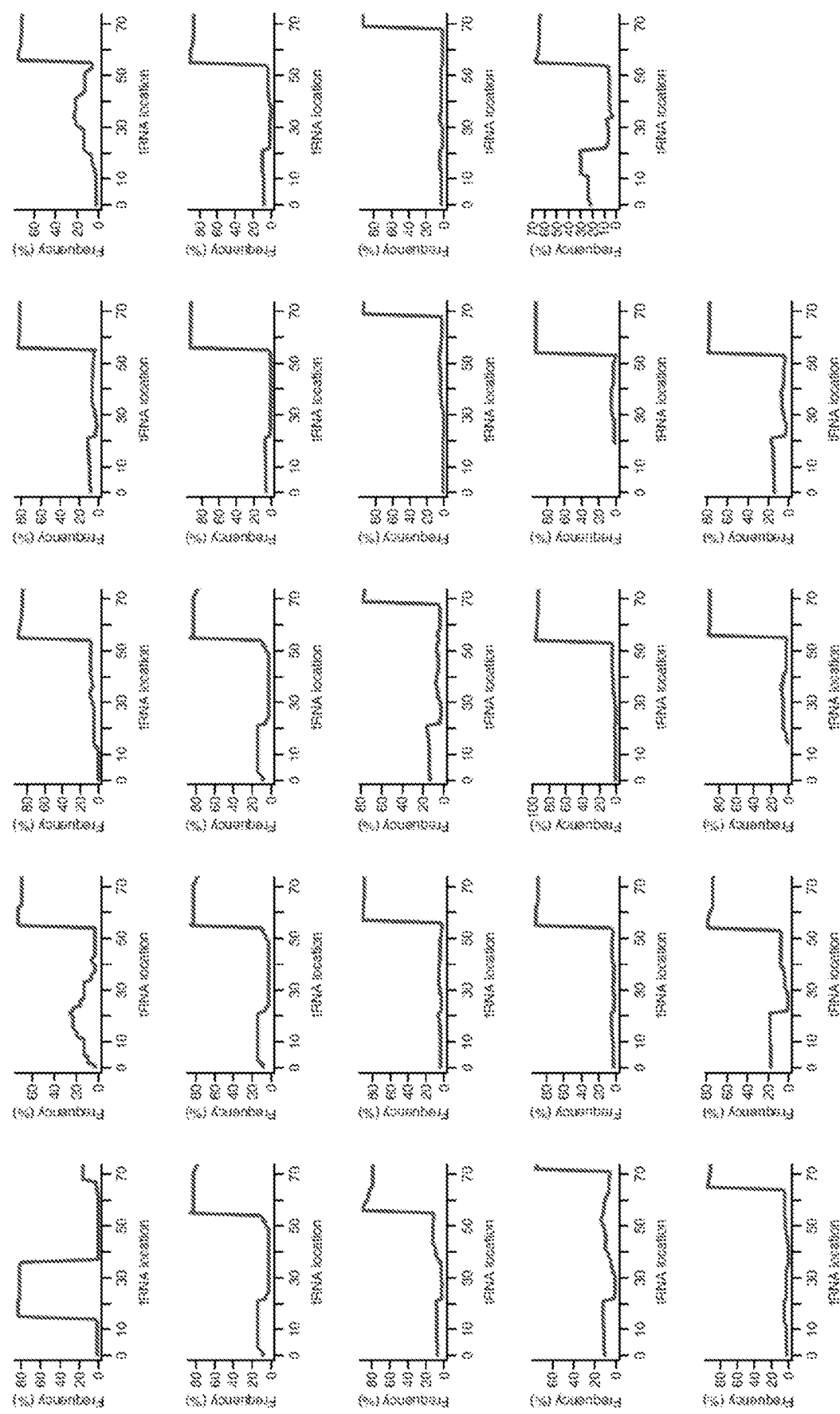

All 50 rhizobial tRNAs produced tRFs in both Rhizobium (strain USDA110) culture and the 10-day-old and 20-day-old soybean (cultivar Williams 82) nodules, with the majority ranging from 18 to 24 nt in size, and abundance varied drastically (see FIGS. 2A and 3A and Table 2). Overall, the tRFs in the nodules were significantly more abundant than those in the Rhizobium culture, with 21-nt tRFs—primarily derived from the 3' ends of the tRNAs—most abundant (see FIGS. 2A and 3A-3C).

A total of 57 soybean genes in the soybean genome were predicted to be targets of 25 distinct 21- or 22-nt rhizobial tRFs, with a relative abundance of >100 copies per million rhizobial small RNA reads (Table 2, with host target sequences being the complementary sequence to that listed as sRNA-seq).

TABLE 2

Rhizobial tRFs derived from B. japonicum and their potential targets in soybean.

| sRNA | target gene | sRNA-seq | tRNA-name | |
|---|---|---|---|---|
| Bj-tRF001 | Glyma.07G010200 | SEQ ID NO: 1 | BJ-tRNA-Val-1 | RHD3 |
| Bj-tRF001 | Glyma.08G193200 | SEQ ID NO: 1 | BJ-tRNA-Val-1 | RHD3 |
| Bj-tRF001 | Glyma.01G189600 | SEQ ID NO: 1 | BJ-tRNA-Val-1 | SKP1/ASK1-interacting protein 2 |

TABLE 2-continued

Rhizobial tRFs derived from *B. japonicum* and their potential targets in soybean.

| sRNA | target gene | sRNA-seq | tRNA-name | |
|---|---|---|---|---|
| Bj-tRF001 | Glyma.11G052600 | SEQ ID NO: 1 | BJ-tRNA-Val-1 | SKP1/ASK1-interacting protein 2 |
| Bj-tRF002 | Glyma.06G108100 | SEQ ID NO: 2 | BJ-tRNA-Gly-3 | Galactosyltransferase family protein |
| Bj-tRF002 | Glyma.04G254100 | SEQ ID NO: 2 | BJ-tRNA-Gly-3 | Galactosyltransferase family protein |
| Bj-tRF002 | Glyma.11G065200 | SEQ ID NO: 2 | BJ-tRNA-Gly-3 | GRAS family transcription factor |
| Bj-tRF002 | Glyma.01G177200 | SEQ ID NO: 2 | BJ-tRNA-Gly-3 | GRAS family transcription factor |
| Bj-tRF002 | Glyma.02G058700 | SEQ ID NO: 2 | BJ-tRNA-Gly-3 | GRAS family transcription factor |
| Bj-tRF002 | Glyma.16G141300 | SEQ ID NO: 2 | BJ-tRNA-Gly-3 | GRAS family transcription factor |
| Bj-tRF003 | Glyma.08G039400 | SEQ ID NO: 3 | BJ-tRNA-Gln-2 | LRR receptor-like serine/threonine-protein kinase |
| Bj-tRF106 | Glyma.07G007700 | SEQ ID NO: 50 | BJ-tRNA-Met-2 | ATPase E1-E2 type family protein |
| Bj-tRF107 | Glyma.19G242600 | SEQ ID NO: 51 | BJ-tRNA-Pro-2 | DNA-binding storekeeper protein-related transcriptional regulator |
| Bj-tRF107 | Glyma.04G054600 | SEQ ID NO: 51 | BJ-tRNA-Pro-2 | Mitochondrial substrate carrier family protein |
| Bj-tRF107 | Glyma.18G278400 | SEQ ID NO: 51 | BJ-tRNA-Pro-2 | Pentatricopeptide repeat (PPR) superfamily protein |
| Bj-tRF107 | Glyma.13G073900 | SEQ ID NO: 51 | BJ-tRNA-Pro-2 | protein kinase 2A |
| Bj-tRF109 | Glyma.10G021500 | SEQ ID NO: 52 | BJ-tRNA-Thr-2 | F-box/RNI-like superfamily protein |
| Bj-tRF144 | Glyma.11G053000 | SEQ ID NO: 53 | BJ-tRNA-Pro-1 | Nucleotide-diphospho-sugar transferases superfamily protein |
| Bj-tRF144 | Glyma.01G189200 | SEQ ID NO: 53 | BJ-tRNA-Pro-1 | Nucleotide-diphospho-sugar transferases superfamily protein |
| Bj-tRF145 | Glyma.17G021200 | SEQ ID NO: 54 | BJ-tRNA-Gln-2 | 2-oxoglutarate (2OG) and Fe(II)-dependent oxygenase superfamily protein |
| Bj-tRF145 | Glyma.05G015400 | SEQ ID NO: 54 | BJ-tRNA-Gln-2 | ATPase E1-E2 type family protein |
| Bj-tRF145 | Glyma.06G017300 | SEQ ID NO: 54 | BJ-tRNA-Gln-2 | DNA-binding bromodomain-containing protein |
| Bj-tRF147 | Glyma.13G050800 | SEQ ID NO: 55 | BJ-tRNA-Ser-1 | RING/U-box superfamily protein |
| Bj-tRF147 | Glyma.19G037800 | SEQ ID NO: 55 | BJ-tRNA-Ser-1 | RING/U-box superfamily protein |
| Bj-tRF148 | Glyma.05G005600 | SEQ ID NO: 56 | BJ-tRNA-Ser-2 | domains rearranged methyltransferase 2 |
| Bj-tRF148 | Glyma.13G050800 | SEQ ID NO: 56 | BJ-tRNA-Ser-2 | RING/U-box superfamily protein |
| Bj-tRF148 | Glyma.19G037800 | SEQ ID NO: 56 | BJ-tRNA-Ser-2 | RING/U-box superfamily protein |
| Bj-tRF151 | Glyma.15G007900 | SEQ ID NO: 57 | BJ-tRNA-OTHER-4 | Tetratricopeptide repeat (TPR)-like superfamily protein |
| Bj-tRF154 | Glyma.06G185400 | SEQ ID NO: 58 | BJ-tRNA-Arg-2 | plant U-box 38 |
| Bj-tRF157 | Glyma.11G089100 | SEQ ID NO: 59 | BJ-tRNA-His-1 | Concanavalin A-like lectin protein kinase family protein |
| Bj-tRF160 | Glyma.09G191700 | SEQ ID NO: 60 | BJ-tRNA-Trp-1 | Enoyl-CoA hydratase/isomerase family |
| Bj-tRF160 | Glyma.11G105900 | SEQ ID NO: 60 | BJ-tRNA-Trp-1 | glycine-rich protein 2B |
| Bj-tRF160 | Glyma.03G238400 | SEQ ID NO: 60 | BJ-tRNA-Trp-1 | Integral membrane Yip1 family protein |
| Bj-tRF160 | Glyma.19G235900 | SEQ ID NO: 60 | BJ-tRNA-Trp-1 | Integral membrane Yip1 family protein |
| Bj-tRF163 | Glyma.20G114800 | SEQ ID NO: 61 | BJ-tRNA-Arg-1 | Hypothetical protein |
| Bj-tRF164 | Glyma.04G092100 | SEQ ID NO: 62 | BJ-tRNA-Leu-4 | dicarboxylate carrier 2 |
| Bj-tRF171 | Glyma.19G189300 | SEQ ID NO: 63 | BJ-tRNA-Ala-3 | Exostosin family protein |
| Bj-tRF173 | Glyma.02G034300 | SEQ ID NO: 64 | BJ-tRNA-Val-3 | splicing factor PWI domain-containing protein |
| Bj-tRF173 | Glyma.04G236700 | SEQ ID NO: 64 | BJ-tRNA-Val-3 | Hypothetical protein |
| Bj-tRF176 | Glyma.06G108100 | SEQ ID NO: 65 | BJ-tRNA-Gly-2 | Galactosyltransferase family protein |
| Bj-tRF176 | Glyma.04G254100 | SEQ ID NO: 65 | BJ-tRNA-Gly-2 | Galactosyltransferase family protein |

TABLE 2-continued

Rhizobial tRFs derived from *B. japonicum* and their potential targets in soybean.

| sRNA | target gene | sRNA-seq | tRNA-name | |
|---|---|---|---|---|
| Bj-tRF176 | Glyma.11G065200 | SEQ ID NO: 65 | BJ-tRNA-Gly-2 | GRAS family transcription factor |
| Bj-tRF176 | Glyma.01G177200 | SEQ ID NO: 65 | BJ-tRNA-Gly-2 | GRAS family transcription factor |
| Bj-tRF177 | Glyma.18G085100 | SEQ ID NO: 66 | BJ-tRNA-Phe-1 | beta-1,2-xylosyltransferase |
| Bj-tRF320 | Glyma.11G087300 | SEQ ID NO: 67 | BJ-tRNA-Leu-4 | Auxin efflux carrier family protein |
| Bj-tRF320 | Glyma.04G255100 | SEQ ID NO: 67 | BJ-tRNA-Leu-4 | Coatomer, alpha subunit |
| Bj-tRF344 | Glyma.10G253300 | SEQ ID NO: 68 | BJ-tRNA-Gly-1 | cysteine-rich RLK (RECEPTOR-like protein kinase) 29 |
| Bj-tRF344 | Glyma.07G044400 | SEQ ID NO: 68 | BJ-tRNA-Gly-1 | Subtilase family protein |
| Bj-tRF344 | Glyma.16G012700 | SEQ ID NO: 68 | BJ-tRNA-Gly-1 | Subtilase family protein |
| Bj-tRF550 | Glyma.10G092500 | SEQ ID NO: 69 | BJ-tRNA-Asn-1 | cytochrome P450, family 93, subfamily D, polypeptide 1 |
| Bj-tRF550 | Glyma.20G209700 | SEQ ID NO: 69 | BJ-tRNA-Asn-1 | myb domain protein 15 |
| Bj-tRF550 | Glyma.14G082600 | SEQ ID NO: 69 | BJ-tRNA-Asn-1 | Plant protein of unknown function (DUF827) |
| Bj-tRF550 | Glyma.06G023300 | SEQ ID NO: 69 | BJ-tRNA-Asn-1 | RAC-like 3 |
| Bj-tRF597 | Glyma.19G127000 | SEQ ID No: 3 | BJ-tRNA-Gln-2 | Homeodomain-like superfamily protein |
| Bj-tRF597 | Glyma.05G190300 | SEQ ID No: 3 | BJ-tRNA-Gln-2 | Plant invertase/pectin methylesterase inhibitor superfamily |
| Bj-tRF597 | Glyma.18G176600 | SEQ ID No: 3 | BJ-tRNA-Gln-2 | XB3 ortholog 1 in *Arabidopsis thaliana* |
| Bj-tRF656 | Glyma.07G269000 | SEQ ID NO: 70 | BJ-tRNA-Leu-5 | C2 calcium/lipid-binding and GRAM domain containing protein |

A total of 68 soybean genes, which also showed at least two-fold reduction of expression in nodules (as compared with uninoculated roots) were defined as the targets of 36 unique tRFs from 25 rhizobial tRNAs (Table 2). These tRFs were neither found in small RNA libraries from non-nodule soybean tissues (NCBI accession no. GSE58779; Table 3 (representative data based on Arikit et al., An atlas of soybean small RNAs identifies phased siRNAs from hundreds of coding genes, *Plant Cell* 26: 4584-4601 (2014), the entirety of which is incorporated herein by reference) nor conventionally predicted to target rhizobial genes.

TABLE 3

Presence/absence of *B. japonicum*-derived tRFs in different tissues of soybean.

| tRF Sequences | Nod10_1 | Nod10_3 | Nod15 | Nod20 | Nod25 | Nod30 | AntW82 |
|---|---|---|---|---|---|---|---|
| SEQ ID NO: 10 | 419 | 569 | 1011 | 1925 | 1021 | 834 | 0 |
| SEQ ID NO: 11 | 265 | 372 | 340 | 731 | 284 | 265 | 0 |
| SEQ ID NO: 12 | 3530 | 6450 | 3234 | 5231 | 2102 | 1603 | 0 |
| SEQ ID NO: 13 | 60 | 95 | 63 | 145 | 69 | 126 | 0 |
| SEQ ID NO: 14 | 268 | 659 | 726 | 1557 | 662 | 478 | 0 |
| SEQ ID NO: 15 | 489 | 437 | 209 | 667 | 325 | 275 | 0 |
| SEQ ID NO: 16 | 1142 | 1382 | 577 | 1240 | 494 | 732 | 0 |
| SEQ ID NO: 17 | 974 | 1170 | 621 | 1021 | 619 | 846 | 0 |
| SEQ ID NO: 18 | 1955 | 1903 | 1868 | 2859 | 1519 | 1078 | 0 |
| SEQ ID NO: 19 | 414 | 367 | 231 | 450 | 174 | 238 | 0 |
| SEQ ID NO: 20 | 383 | 408 | 199 | 346 | 154 | 191 | 0 |
| SEQ ID NO: 21 | 139 | 253 | 165 | 357 | 124 | 158 | 0 |
| SEQ ID NO: 22 | 6079 | 7235 | 4324 | 8686 | 5301 | 7720 | 0 |
| SEQ ID NO: 23 | 1067 | 634 | 326 | 538 | 289 | 754 | 0 |
| SEQ ID NO: 24 | 150 | 227 | 175 | 315 | 113 | 120 | 0 |
| SEQ ID NO: 25 | 79 | 126 | 79 | 164 | 76 | 72 | 0 |
| SEQ ID NO: 26 | 163 | 182 | 81 | 211 | 99 | 152 | 0 |
| SEQ ID NO: 27 | 206 | 274 | 115 | 289 | 117 | 126 | 0 |
| SEQ ID NO: 28 | 2301 | 2744 | 3270 | 7007 | 3333 | 2424 | 0 |
| SEQ ID NO: 29 | 0 | 9 | 12 | 33 | 12 | 8 | 0 |
| SEQ ID NO: 30 | 58 | 100 | 48 | 93 | 49 | 61 | 0 |
| SEQ ID NO: 31 | 9 | 18 | 7 | 14 | 7 | 15 | 0 |
| SEQ ID NO: 32 | 7 | 11 | 8 | 15 | 19 | 18 | 0 |
| SEQ ID NO: 33 | 27 | 18 | 11 | 16 | 19 | 145 | 0 |

Referring back to Table 2, of the soybean genes, GmRHD3a/GmRHD3b, GmHAM4a/GmHAM4b, and GmLRX5—which are orthologs of the *Arabidopsis* Root Hair Defective 3 (RHD3), Hairy Meristem 4 (HAM4), and Leucine-Rich Repeat Extension-Like 5 (LRX5), respectively—were identified for further study, in part, because these *Arabidopsis* genes are important for root hair and plant development. Indeed, these soybean genes were predicted to be the targets of three rhizobial tRFs—dubbed Bj-tRF001, Bj-tRF002, and Bj-tRF003—which are the predominant products derived from three tRNAs: Val-1-tRNA(CAC), Gly-1-tRNA(UCC), and Gln-1-tRNA(CUG), respectively (see FIG. 2, subparts I-K).

Figure 5A:
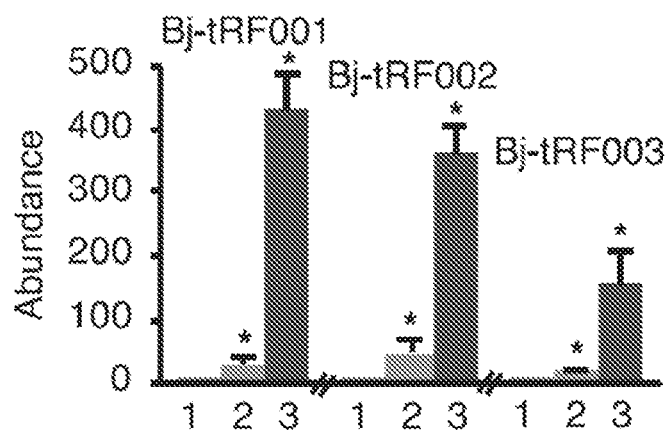
FIG. 5A shows graphical data illustrating the abundance of the three tRFs, measured by means of stem-loop quantitative RT-PCR, in free-living *B. japonicum* (*B. j.*) USDA110 (1) and 10-day and 20-day post-inoculation (dpi) nodules (2 and 3, respectively), with values shown as means±SE from three biological replicates (one set as "1" and the others adjusted accordingly), and asterisks indicating the significance level at p<0.01 (Student's t test)
Figure 5B:
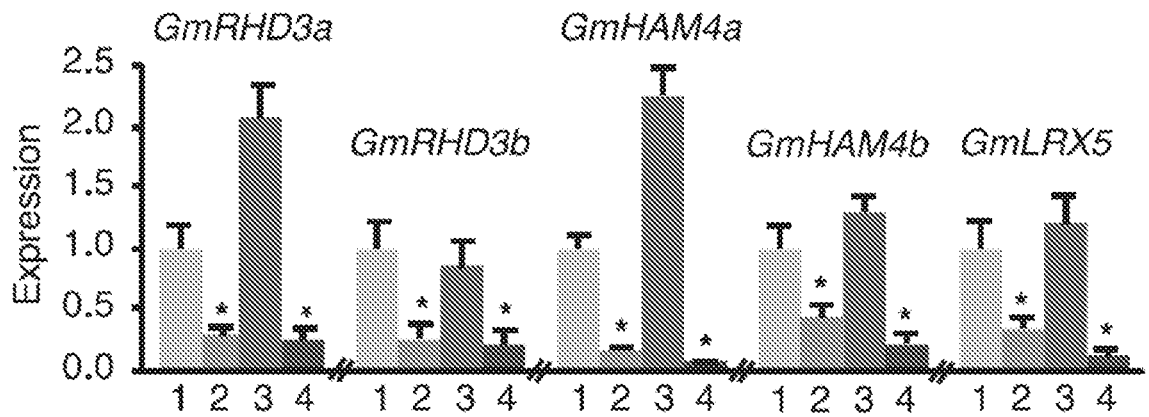
FIG. 5B shows graphical data illustrating the expression of the identified tRF target genes, measured with quantitative RT-PCR in the 10-day-old and 20-day-old nodules (2 and 4, respectively) and uninoculated soybean roots (1 and 3), with values shown as means±SE from three biological replicates (one set as "1" and the others adjusted accordingly), and asterisks indicating the significance level at p<0.01 (Student's t test)
Figure 5C:
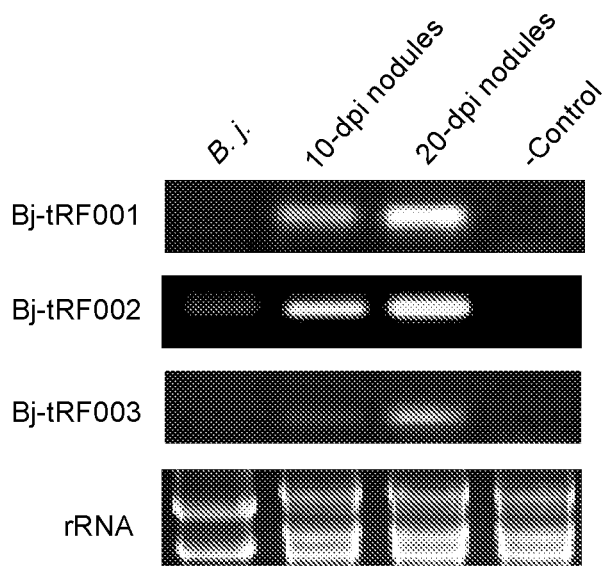
FIG. 5C shows a gel following the enrichment of three rhizobial tRFs in soybean root nodules, with abundance shown relative to that of the transcripts from a *B. japonicum* gene bll631 in free living *B. japonicum* strain USDA110, and 10-dpi and 20-dpi nodules detected by stem-loop RT-PCR using the reaction from the 20-dpi RNA sample without adding reverse transcriptase as a negative control; the specificity of stem-loop RT-PCR products from individual tRFs confirmed by sequencing of the amplified fragments and equal amounts of total RNAs from different samples loaded on the gel to visualize different sizes and relative abundances of rhizobial rRNAs and soybean rRNAs.
Figure 6F:
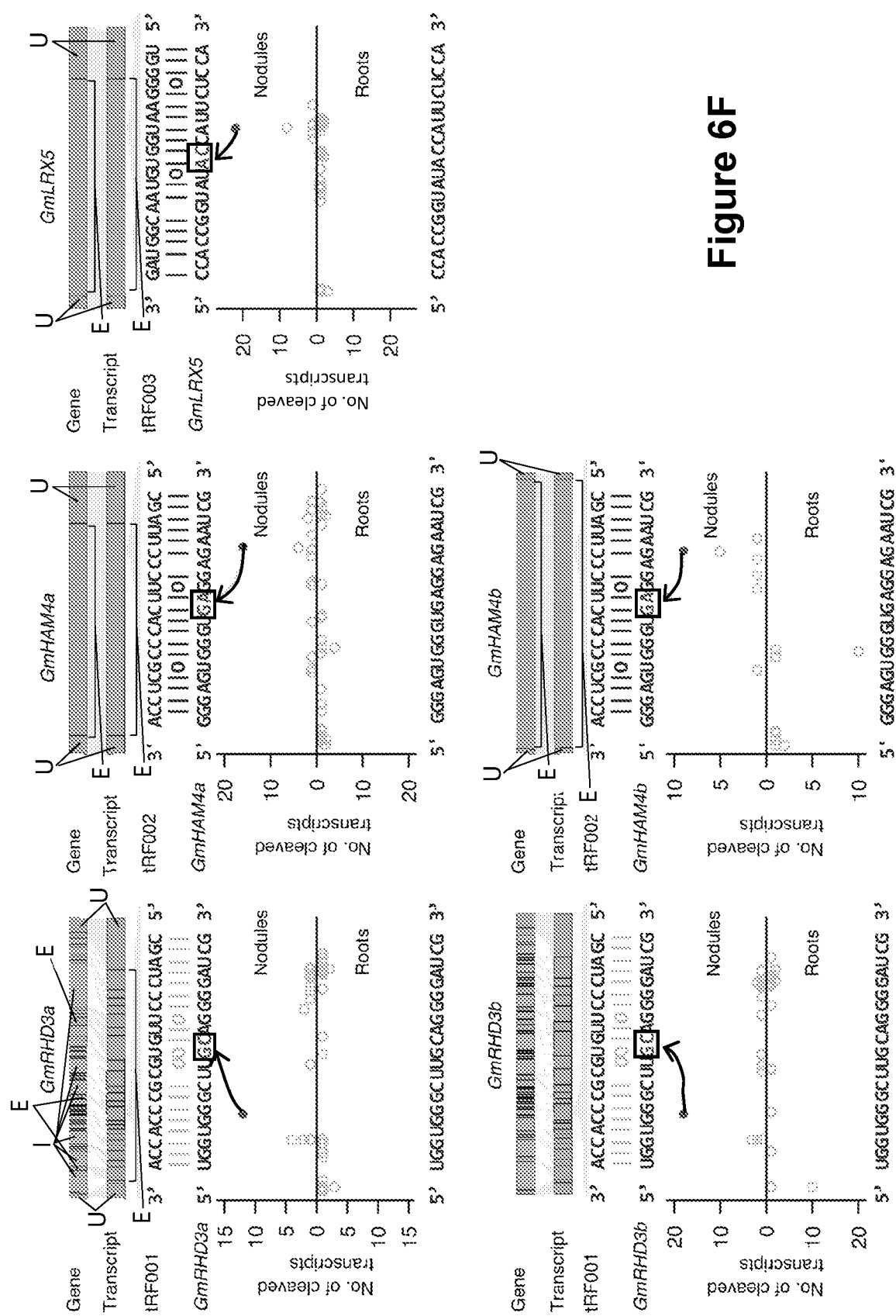
FIGS. 6A-6C show the three identified tRFs of the present disclosure, their putative target transcripts, and the cleavage sites and frequencies (indicated with arrows and ratios) that were detected in the 20-dpi nodules.
FIG. 6D shows the sequences of artificial small RNAs, asRNA001 (SEQ ID NO: 1) and asRNA001*, and a BJ-tRF001 target site as identified herein.
FIG. 6E shows graphical data illustrating that target host gene GmRHD3a 3b has reduced expression in soybean asR001-transgenic root protoplasts as compared with that in asR001*-transgenic root protoplasts 20 h post transformation, with levels of gene expression relative to that of GmCos4 as detected by qRT-PCR and shown as means±standard errors from three biological replicates (in each panel, the expression level of one sample was set at 1 and those of the others adjusted accordingly; * and ** indicate significant difference at P<0.05 and P<0.01, respectively (t-test)

Enrichment of the three identified rhizobial tRFs in the nodules compared with the uninoculated *Rhizobium* culture (i.e. the transcripts from a *B. japonicum* gene b11631 in the free-living (wild-type) *B. j.* strain USDA110) was further validated by means of stem-loop RT-qPCR assay (see FIGS. 5A and 5C). Specifically, abundance of these three rhizobial tRFs in the 10-dpi and 20-dpi nodules was detected (x-axis labeled 2 and 3 in FIG. 5A, respectively). A reaction from the 20-dpi RNA sample without adding reverse transcriptase served as a negative control (x-axis labeled 1 in FIG. 5A).

The specificity of stem-loop RT-PCR products from individual tRFs was then confirmed by sequencing the amplified fragments. Equal amounts of total RNAs from different samples were loaded onto the gel to visualize different sizes and relative abundances of rhizobial rRNAs and soybean rRNAs. As expected, the reduced expression of their candidate gene targets in the nodules as compared with the uninoculated roots was revealed (see FIG. 5B).

Example 2

Target Genes' Cleavage Site in the Transcripts and Suppression by tRFs

To confirm that the identified soybean genes were the targets of the three rhizobial tRFs, cleavage sites in the transcripts of these genes were identified by RNA ligase-mediated 5' rapid amplification of cDNA ends (RLM-RACE). If the reduced expression of these soybean genes was caused by the identified rhizobial tRFs through miRNA-like posttranscriptional regulation, cleavage of the mRNAs from these genes at the predicted tRF target sites would occur.

Examining this, the data supports that the mRNAs of these genes were in fact exactly cleaved at the predicted tRF target sites in the 20-day nodules, whereas none of these sites were cleaved in the uninoculated roots (see FIGS. 6A-6C and 6E). This clearly supports these tRFs repress the expression of the target genes by a miRNA-like post-transcriptional regulatory mechanism.

Importantly, none of these sites were complementary to or, prior to this study, predicted to be targeted by previously identified soybean small RNAs. Indeed, soybean miR171k was the only small RNA predicted to target GmHAM4/GmHAM4b, but it was primarily expressed in the uninoculated roots (9.38 counts per million reads) instead of the nodules (0.27 counts per million reads) and, thus, unlikely to be responsible for the observed repression of GmHAM4a GmHAM4b in the nodules. Accordingly, the data indicates that there is, in fact, cross-kingdom communication between the newly identified rhizobial tRFs and the soybean genes thus supporting that the rhizobial tRFs do participate in the regulation of nodulation.

To understand the significance of individual tRFs in repressing its target(s), two artificial small RNAs, asRNA001 (identical to Bj-tRF001) and asRNA001* (complementary to asRNA001) (FIG. 6D) were synthesized and transformed separately into the protoplasts prepared from soybean (cv., Williams 82) roots grown in sterile tissue culture. Significant or substantial reductions of the transcripts of both GmRHD3a and GmRHD3b were detected in the asRNA001 transformation protoplast as compared to these in the asRNA001* transformation protoplast (FIG. 6E), supporting that an individual 21-nt rhizobial tRF is sufficient for post-transcriptional repression of its target.

Example 3

Mutations of tRFs' Target Genes Resulted in Nodule Initiation

Heretofore, the potential functions of GmRHD3a GmRHD3b, GmHAM4a GmHAM4b, and GmLRX5 in soybean and their homologs in other legumes were unknown. As these genes were downregulated by rhizobial tRFs only detected locally in the root nodules of soybean as previously described, it was contemplated that these genes are associated with nodulation. To determine whether the repression of GmRHD3a GmRHD3b, GmHAM4a GmHAM4b, and GmLRX5 expression in the nodules is, in fact, associated with nodulation, root mutants were created by means of CRISPR-Cas9 (CR) (FIGS. 7A and 7B) through hairy root transformation for each of the five genes and for both copies of each of the two duplicated gene pairs, followed by inoculation with *Rhizobium* strain USDA110. The controls were transgenic roots of empty vectors used for the CR knockouts.

Figure 8A:
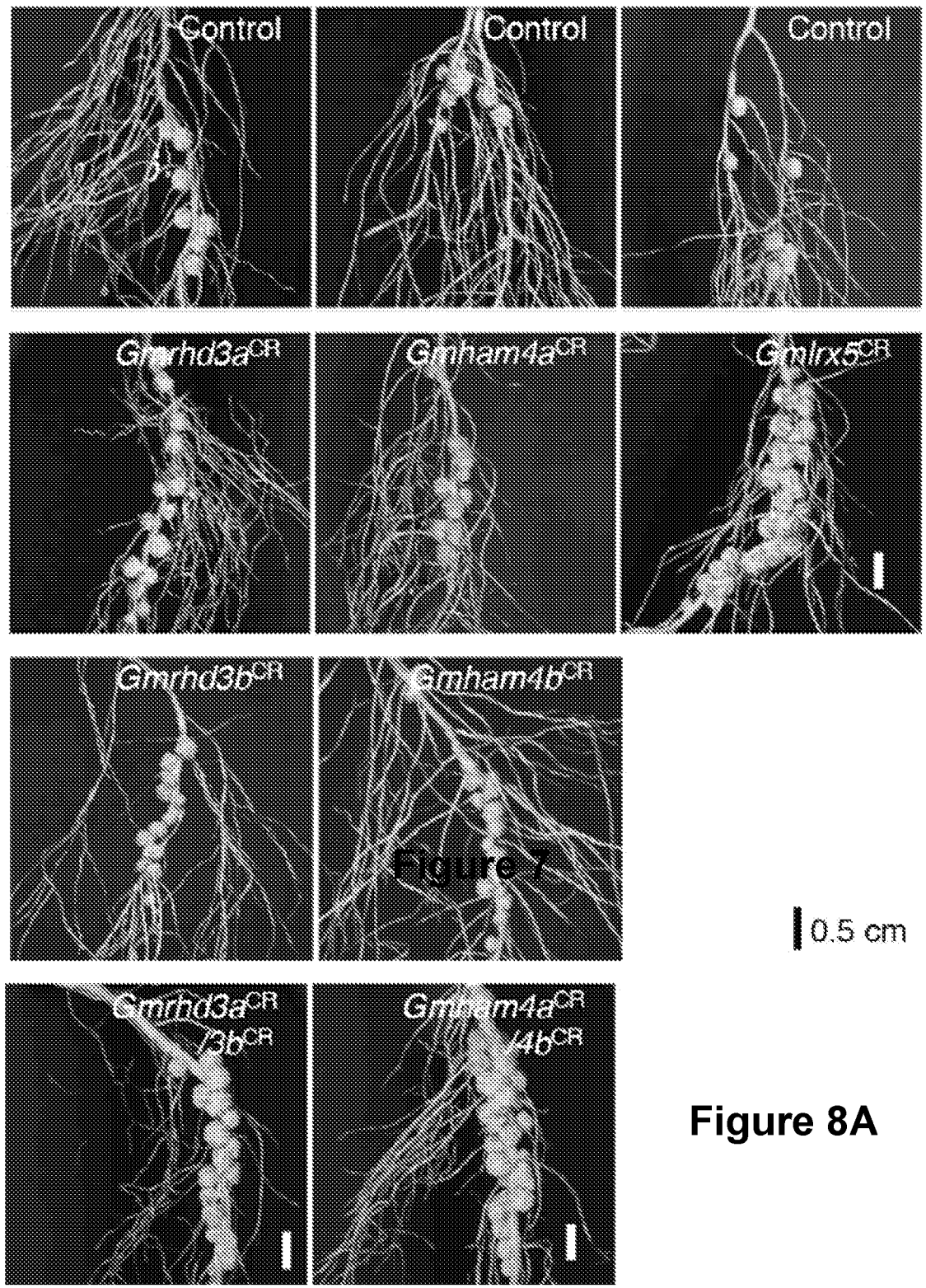
FIG. 8A shows photographs of the roots of mutants for each of the five genes (GmRHD3a, GmRHD3b, GmHAM4a, GmHAM4b, and GmLRX5) and both copies of the two duplicated gene pairs (GmRHD3a GmRHD3b and GmHAM4a GmHAM4b), with each of the knockouts having increased nodule numbers over the controls.

In all cases, expression of the edited genes produced more nodules than those of the empty-vector transgenic controls. Furthermore, the double mutants (Gmrhd3a/Gmrhd3b and Gmham4a/Gmham4b) produced the greatest number of nodules. FIG. 8A shows photographs of the roots of each mutant and the controls, with all mutants having knockouts of the identified tRF targets by means of CR resulting in significantly increased nodule numbers. FIG. 8B additionally shows a graphical representation of the resulting nodule numbers.

Example 4

Overexpression of tRFs' Target Genes Reduces Nodule Numbers

Overexpression of GmRHD3b, GmHAM4a, and GmLRX5 in the nodules was also examined with respect to its effect on nodulation. Transgenic roots were prepared that overexpressed GmRHD3b, GmHAM4a, or GmLRX5, separately, by the cauliflower mosaic virus (CaMV) 35S promoter, which increased expression of such genes (i.e. the tRF targets). As seen in FIGS. 9A-9C, overexpression of these genes resulted in a dramatic reduction in nodule numbers in the gene-overexpression roots as compared to the control non-transgenic roots. This, taken with the data of the other studies presented herein, supports that these genes are negative regulators of nodulation.

Example 5

Figure 10A:
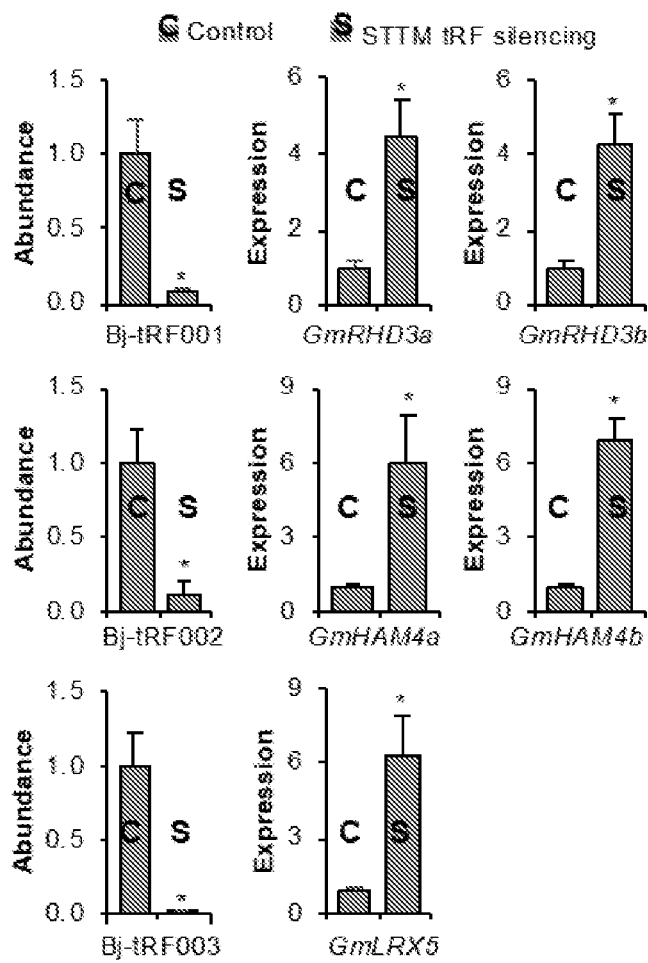
FIG. 10A shows graphical data related to the increased expression of the rhizobial tRF targets in the STTM hairy roots that inhibited the rhizobial tRF function (S) as compared with that in an empty vector transgenic control (C), with levels of gene expression relative to that of GmELF1b as detected by qRT-PCR, shown as means±s.e. from three biological replicates, and all samples collected 28 dpi.

Rhizobial tRFs Directly Act on Nodulation Through Cleavage of Transcripts of Target Genes To examine the direct effects of individual rhizobial tRFs on nodulation through the cleavage of the transcripts from their targets, transgenic short tandem target mimic (STTM) soybean roots were generated to silence each of the three rhizobial tRFs. As shown in FIG. 10A, the expression of each of the three tRFs was almost completely blocked following completion of the STTM protocol described herein; consequently, the expression levels of the identified genes were significantly increased. FIG. 10D shows the reduced abundance of rhizobial tRFs and increased expression of soybean genes in the STTM hairy roots with the nodules removed and in the nodules (controls (C) and STTM roots/nodules (S)).

Figure 10B:
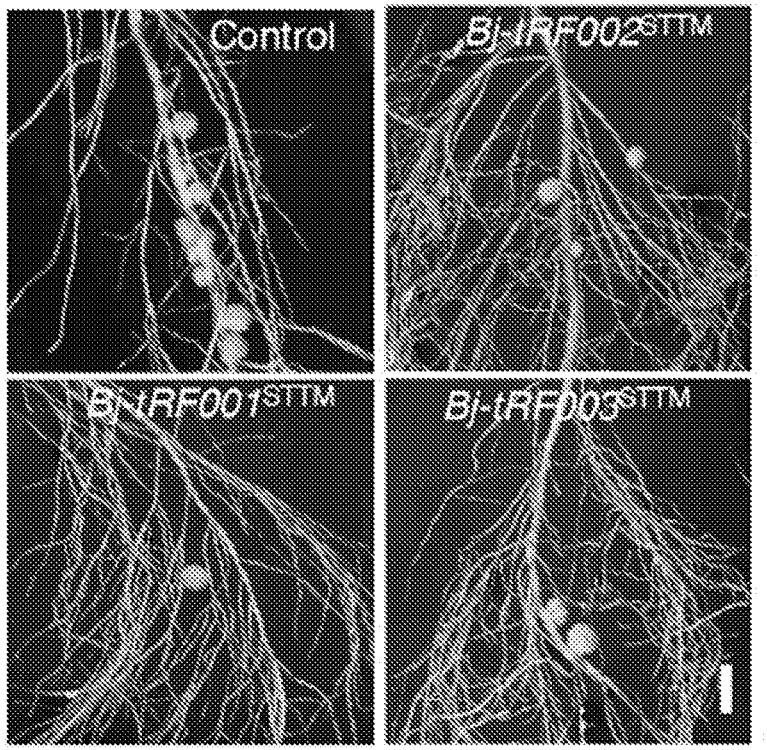
FIG. 10B shows photographs of transgenic roots engineered to silence individual tRFs by means of STTM.
Figure 10C:
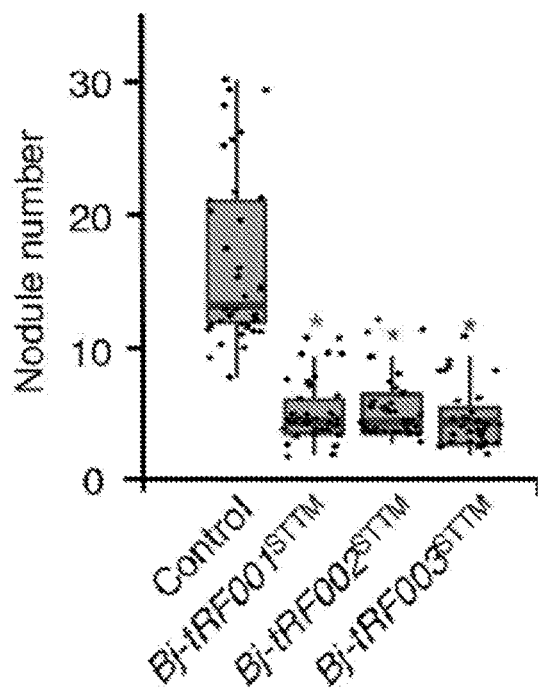
FIG. 10C shows a graph of the nodule numbers of the roots shown in FIG. 10A all data points represented by dots and shown as box and whisker plots displaying 95 to 5% interval from three biological replicates (12 plants per replicate) collected 28 days after inoculation, and shown as means±standard deviations from three independent experiments (n=12 per experiment))
Figure 10D:
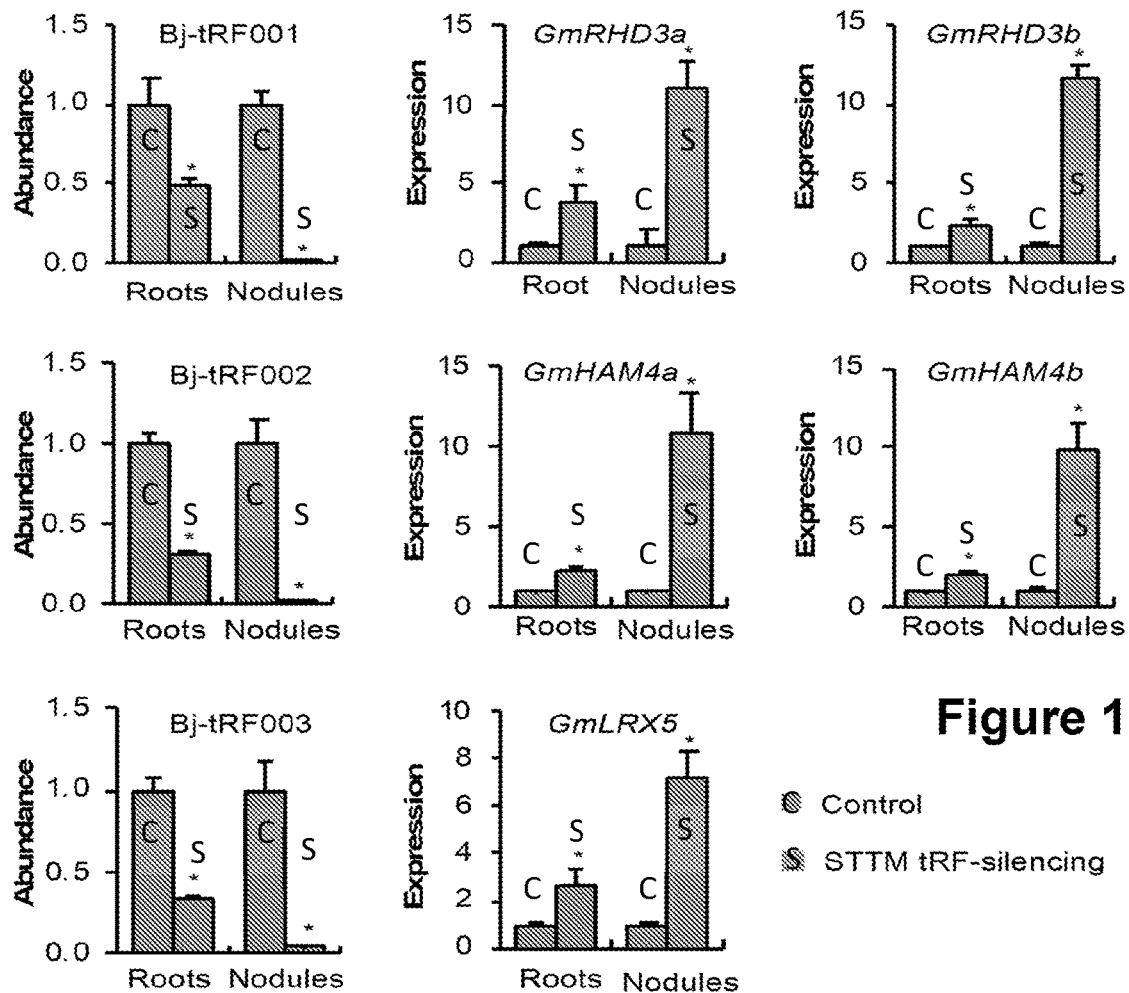
FIG. 10D shows graphical data related to rhizobia tRFs and the expression of the identified target genes in STTM transgenic roots and nodules, where the expression levels of the tRFs and soybean genes relative to that of GmELF1b were detected by qRT-PCR, shown as means±s.e. from three biological replicates, controls were transgenic roots of empty-vector used for developing the STTM tRF-silencing roots, and all samples collected 28 dpi (FIGS. 10A, 10C and 10D, asterisks in indicate the significance level of $P<0.01$ (Student's t test) and, in each panel of FIGS. 10A and 10D, the expression level of one sample was set as 1 and those of the other adjusted accordingly)

As shown in FIGS. 10B and 10C, nodule numbers in the STTM roots were significantly decreased as compared to those of the empty-vector transgenic controls. As expected, relative abundance of the three tRFs was also decreased and expression of the identified targets was increased, supporting that these tRFs are positive regulators of nodulation and function through repressing the associated target genes. Given the lack of sequence complementarity of these rhizobial tRFs to the transcripts of any other soybean genes in the entire genome, there is a significantly high likelihood that the effect of the tRFs on nodule formation directly results from the repressed expression of their targets.

Example 6

Rhizobial tRFs and the Target Genes in the Host Cells Interact During Rhizobial Infection As rhizobial infection is a critical step for initiating nodules, how tRF-mediated regulation of the five soybean target genes affects rhizobial infection was examined. The expression patterns of the five tRF targets in soybean root hairs at early stage post inoculation with USDA110 was then explored.

Figure 11A:
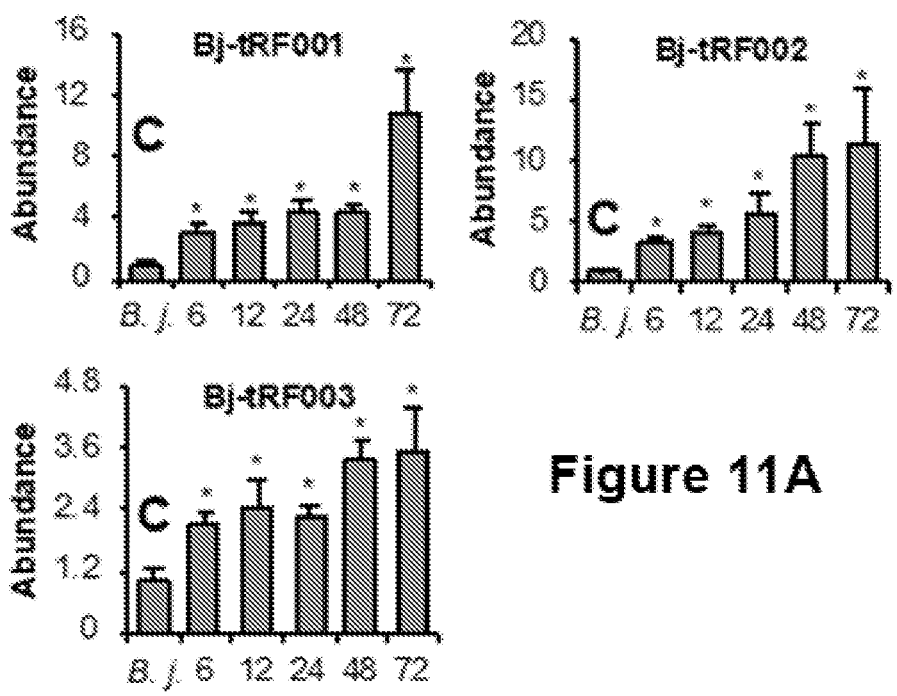
FIGS. 11A and 11B show the rhizobial tRF abundance and expression of their target genes at early-stage rhizobial infection of soybean root hairs, with FIG. 11A showing graphical data representative of the enrichment of rhizobial tRFs relative to the transcripts of *rhizobium* bll631 in root hairs (unmarked) as compared to that in free-living *rhizobia* (C) detected by stem-loop RT-qRT-PCR, and FIG. 11B showing graphical data showing reduced expression of the rhizobial tRF targets relative to GmELF1b in root hairs as compared with expression in uninoculated root hairs measured by qRT-PCR (values in FIGS. 11A and 11B shown as means±s.e. from three biological replicates, and the value of one sample was set as 1 and those of the others adjusted accordingly; asterisks indicating significant difference at $P<0.05$ (t-test)
Figure 11B:
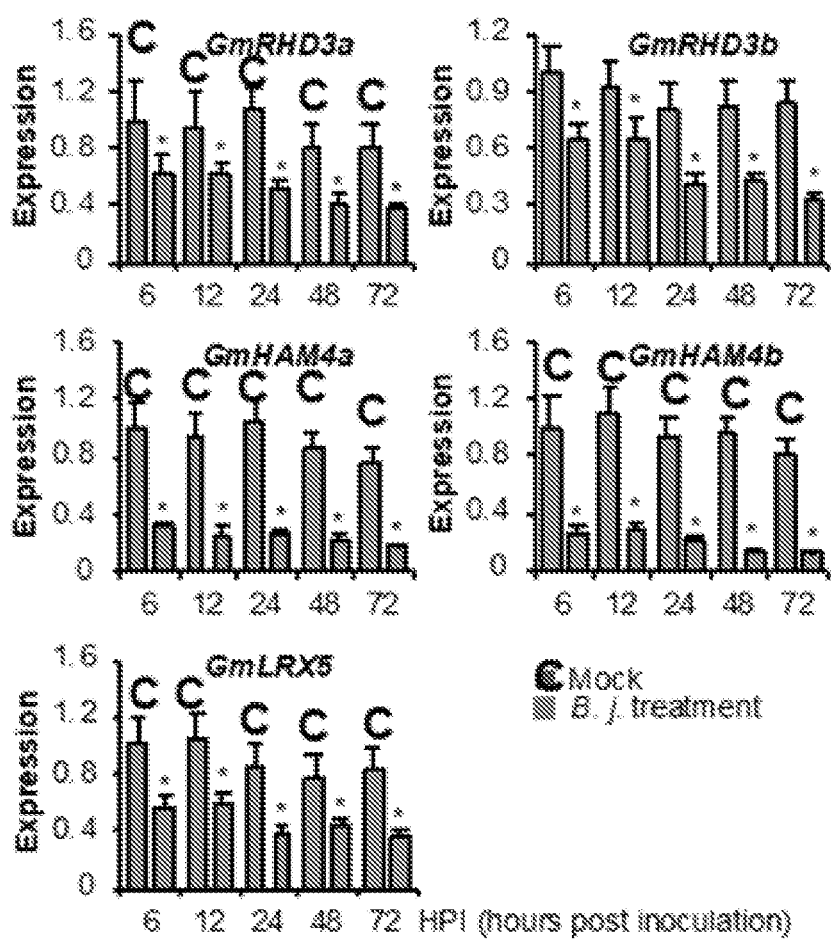

At all five time points examined, the abundance of the three tRFs targeting these genes was increased from 6 hpi to 72 hpi (FIG. 11A). By contrast, all five genes showed significantly reduced levels of expression in inoculated root hairs as compared with uninoculated root hairs (FIG. 11B). All five genes also showed decreased expression from 6 hpi to 72 hpi. This data supports that interactions do occur between rhizobial tRFs and their target genes in the host cells during rhizobial infection.

Example 7

Root Phenotypes in Relation with Target Gene Expression and Silencing by Rhizobial tRFs Following the profiling of host gene expression in inoculated root hairs at early stages of rhizobial infection, the morphology of inoculated root hairs in which GmRHD3b, GmHAM4a, and GmLRX5 were overexpressed by the 35S promoter were examined, as well as the morphology of inoculated root hairs in which each of the three rhizobial tRFs targeting GmRHD3a GmRHD3b, GmHAM4a GmHAM4b, and GmLRX5 were silenced by STTM (both studies using vector-transgenic roots as controls). For each hairy root, 1-cm segments in the mature zone were cut, fixed and examined under microscope.

Figure 12:
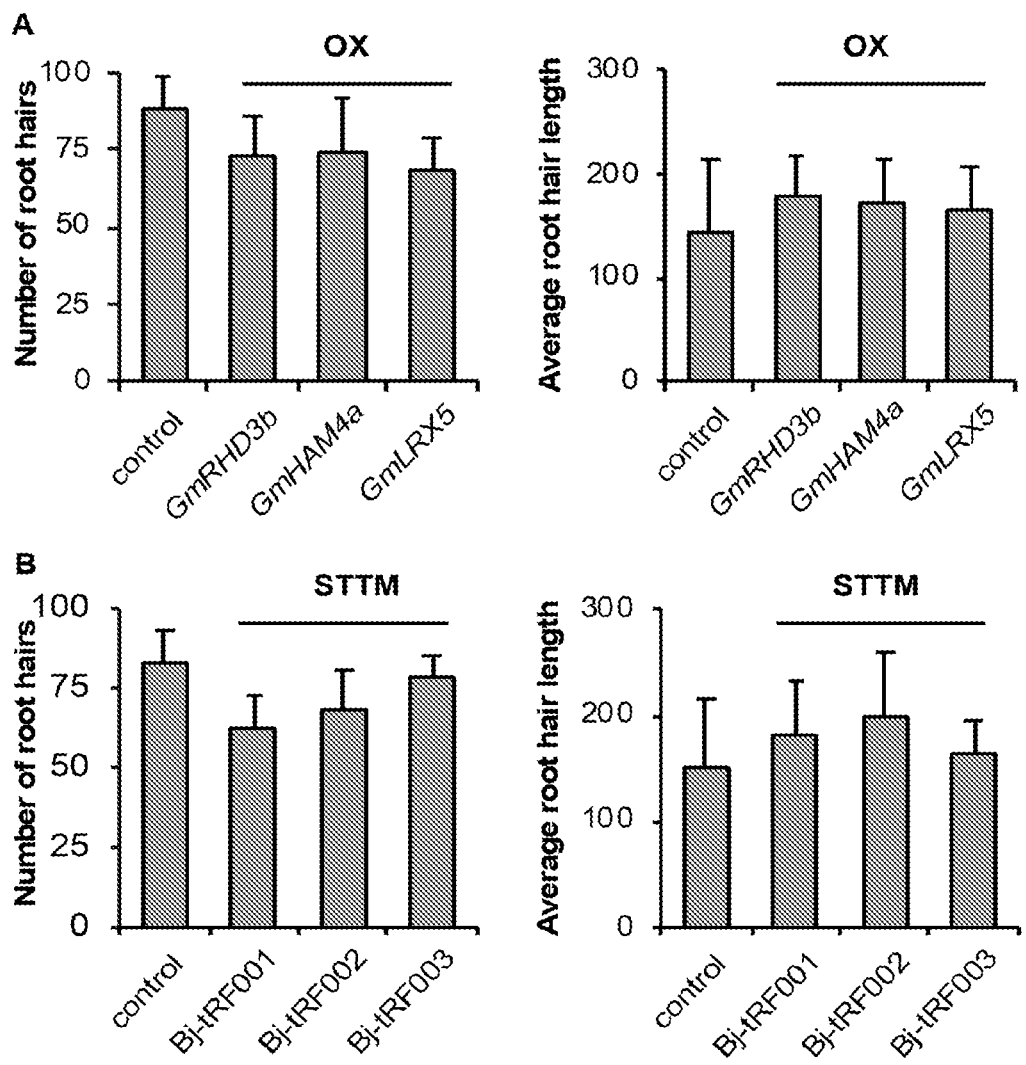
FIG. 12 shows graphical data related to root hair numbers and lengths in overexpression and STTM transgenic hairy roots, with subpart A showing a comparison between soybean hairy roots overexpressing the rhizobial tRF target genes and hairy roots transformed with the empty vector at 6 dpi, and subpart B showing a comparison between soybean STTM hairy roots inhibiting the rhizobial tRF function and hairy roots transformed with the empty vector at 6 dpi (values shown as means s.d. of the means from three independent experiments (each experiment, n=25)
Figure 13:
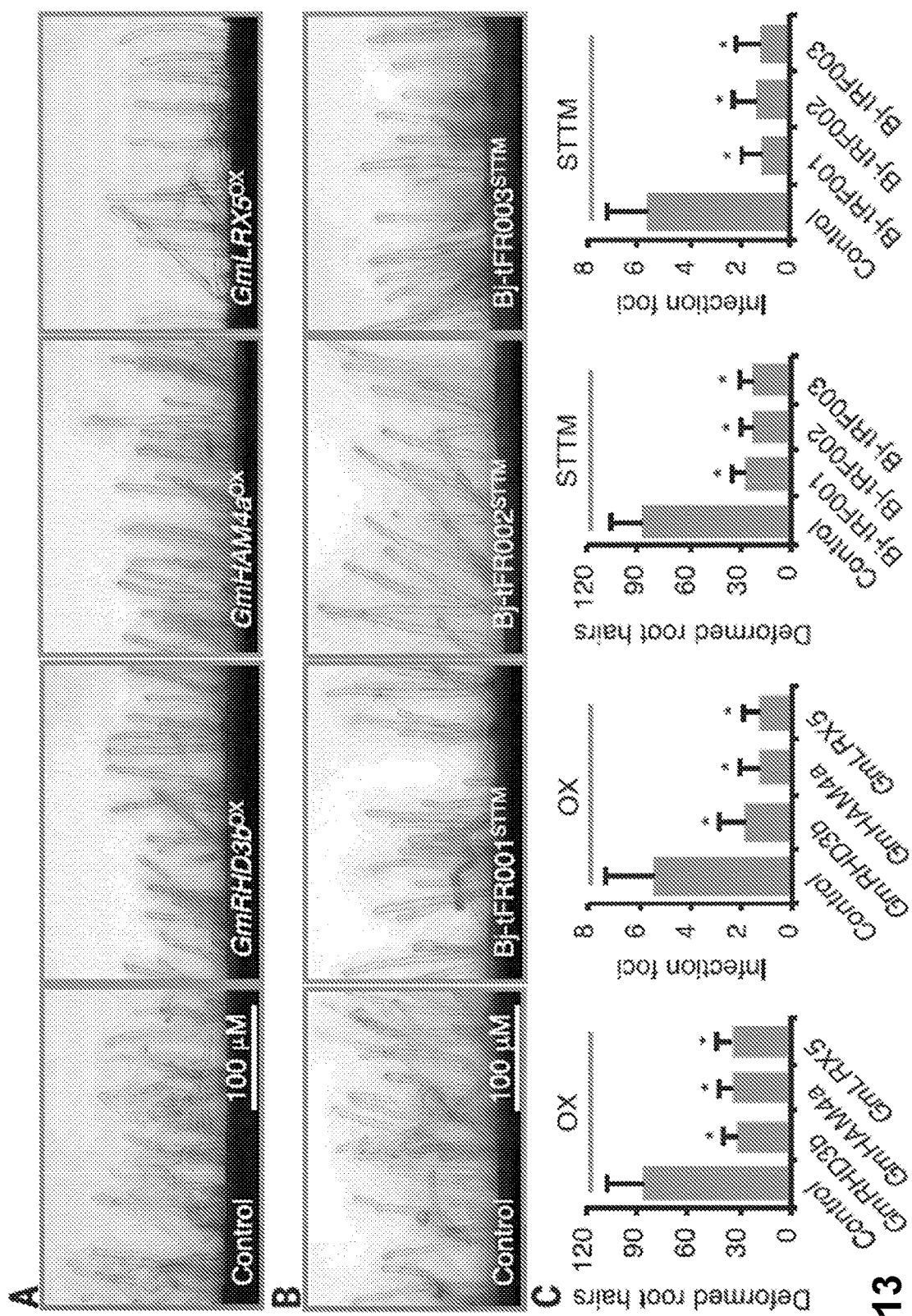
FIG. 13 shows data related to modulation of early-stage rhizobial infection by rhizobial tRFs and their targets in soybean, with subparts A and B showing the morphological differences between the root hairs overexpressing the rhizobial tRF targets and the negative control (subpart A) and between the STTM root hairs inhibiting the rhizobial tRF function and the negative control (subpart B) and subpart C showing graphical data related to the quantitation of deformed root hairs and curled root hairs with infection foci in samples as exemplified in subparts A and B (values shown as means±SD from three biological replicates (n=25 hairy roots per replicate) and asterisks indicating the significant level at $P<0.05$ (Student's t test)

No significant differences in root hair number and root hair length were observed between each of the three GmRHD3b, GmHAM4a, and GmLRX5 overexpression roots and the controls, or between the tRF-silencing STTM roots and the controls (FIG. 12); however, the proportions of deformed and curled root hairs were significantly decreased in each of the three overexpression and STTM roots as compared with respective controls (FIG. 13, subparts A-C). It is documented that rhizobial Nod factor perception in legume roots induces expression of nodulation genes and causes curling of root hairs that entrap the *Rhizobia* to form nodules. In view of this, the presently described data supports that both root hair curling and nodule number are positively regulated by rhizobial tRF and that rhizobial tRFs promote rhizobial infection.

Example 8

Verification of Rhizobial tRF Mechanism

To better understand the mechanism through which rhizobial tRFs regulate nodulation and to confirm expression of certain constructs can result in production of the desired "artificial tRFs" in a plant in vivo, two artificial miRNA precursors, aMIR-tRF001 and aMIR-tRF003, were constructed by replacing the miR172a and miR172a* sequences from the soybean miR172a precursor MIR172a with rhizobial tRF001 and its complementary tRF001* or with tRF003 and its complementary tRF003*. FIG. 14D illustrates the structure of such artificial miRNA genes. aMIR-tRF001 and aMIR-tRF003 (identical/complementary to Bj-tRF001 and Bj-tRF003) were expressed separately in Williams 82 hairy roots under the control of 35S promoter to produce artificial miRNAs amiR-tFR001 and amiR-tFR003 in the transgenic roots (see FIG. 14A, control data labeled C, transgenic root data labeled X).

Figure 14B:
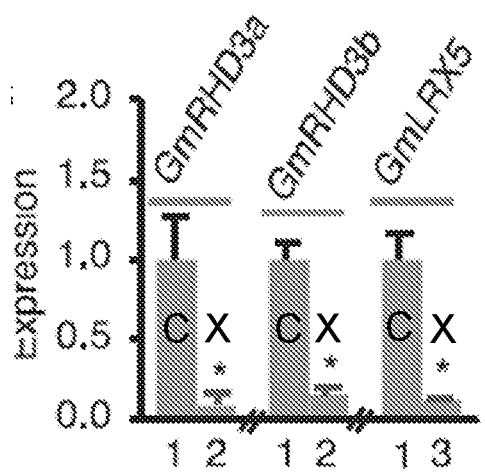
Figure 14C:
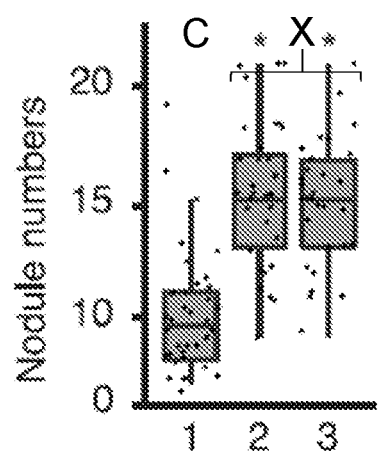
Figure 14D:
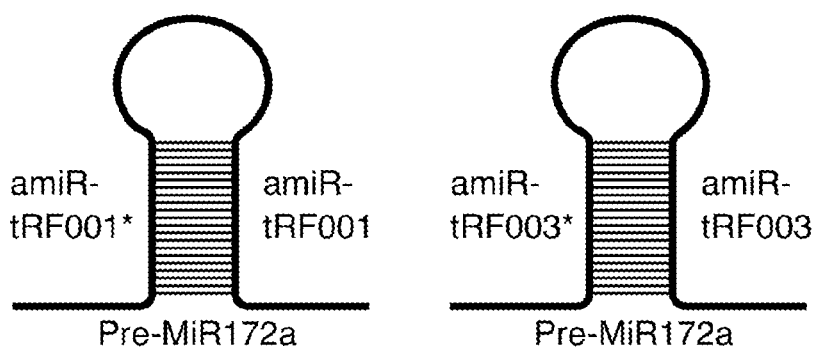
FIG. 14D shows a schematic representing the structure of the artificial miRNA genes producing artificial miRNAs pursuant to the methods of the present disclosure, where such produced miRNAs are identical to two wild-type rhizobial tRF sequences.

As shown in FIG. 14B, expressions of the amiR-tFR001 and amiR-tFR003 targets GmRHD3a 3b and GmLRX5 (data labeled X) was significantly reduced as compared with that of empty-vector transgenic controls (data labeled C). Likewise, as seen in FIG. 14C, more nodules were produced in the aMIR-tRF001 and aMIR-tRF003 transgenic roots (data labeled X) than in the respective controls (data labeled C). These results support that the artificial miRNA/tRF sequences did result in production of the desired artificial tRFs in the roots and directly repressed the identified host gene targets to promote nodulation.

To determine the extent sequence complementarity is required for artificial miRNA/tRF-mediated gene regulation, two sets of fusion genes were made by adding each of the 21-base pair (bp) of DNA fragments corresponding to each the three identified tRF target sites (wild type) and each of the 21-bp of DNA fragments with 4-bp modification at the detected cleavage site of the targeted plant gene (mutation type) to the coding sequence of the Green Fluorescence Protein (GFP) gene. The fusion genes were then separately expressed under the control of the 35S promoter in Williams 82 hairy roots (see FIG. 15, subpart A).

As shown in FIG. 15, subparts B and D, there was a notable reduction of GFP activity in the "wild-type" roots (W1-W3) about 24 hours after inoculation with USDA110, whereas no observable change of the GFP activity in the "mutation type" roots (M1-M3). The relative abundance of GFP transcripts was also consistent with GFP activity (see FIG. 15, subpart C). The mutation type plant genes were not cleaved by the tRFs, which strongly supports the tRF cleavage mechanism described herein. Accordingly, these results indicate that the "wild-type" fusion genes were negatively regulated through base-pairing of their mRNAs at the integrated "target sites" with the rhizobial tRFs.

Example 9 tRFs Action Through AGO1 Pathways

In *Arabidopsis*, AGO1 is a component of the RNA-induced silencing complexes that mediate miRNA-guided cleavage of target mRNAs. The expression of AGO1 is upregulated in response to infection by several plant viruses and has been shown to be responsible for translational inhibition or cleavage of complementary target mRNAs in the miRNA pathway.

To determine whether the rhizobial tRFs act through the functional counterpart of AGO1 in soybean, one (GmAGO1b) of the two soybean orthologs of the *Arabidopsis* AGO1, whose transcripts are relatively more abundant than those of the other (GmAGO1a) in soybean root nodules, was fused with the Myc epitope tag and expressed in the hairy roots of Williams 82. The fusion protein was then immunoprecipitated by the Myc antibody from the 20-day nodules induced by USDA110.

Figure 16:
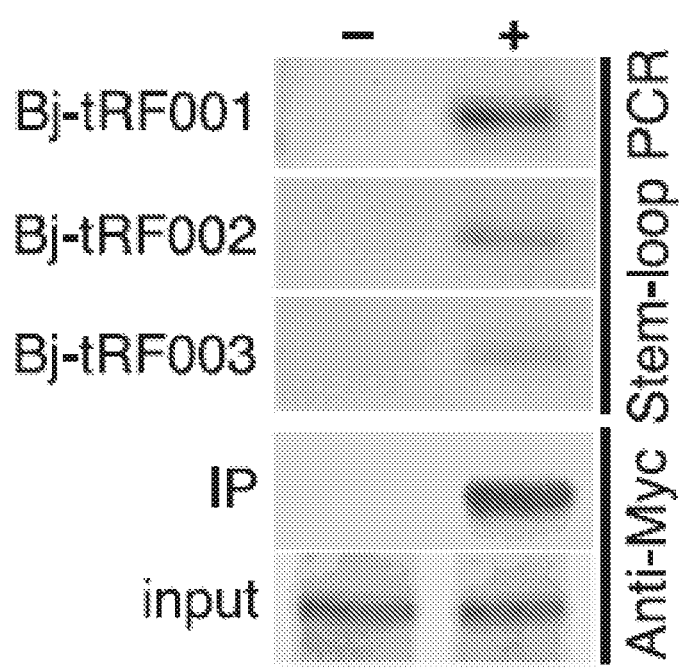
FIG. 16 shows a gel illustrating the association of the three tRFs with soybean GmAGO1b in nodules 28 days after inoculation detected from the three experimental replicates, with "+" and "−" indicative of the GmAGO1b-Myc fusion protein-associated fraction immunoprecipitated by the Myc antibody and the nodule lysate without Myc antibody incubation, respectively.

As shown in FIG. 16, all three rhizobial tRFs were detected in the GmAGO1b-Myc-associated fraction pulled down by the Myc antibody, but not detected in the nodule lysate incubated without the antibody. This data supports that these rhizobial tRFs hijacked the soybean AGO1 to instead catalyze tRF-guided cleavage of target mRNAs in the host cells.

Interestingly, referring back to Example 6, the tRF-mediated regulation of host gene expression was actually detected at early stages of rhizobial infection. At all five time points from 6 to 72 hours after inoculation with USDA110, the abundance of the three tRFs was increased in the inoculated root hairs as compared to the uninoculated root hairs (FIG. 11A), whereas the expression of their targets was decreased (FIG. 11B). This data supports tRFs do, in fact, employ an miRNA-like mechanism to regulate gene expression.

Example 10

Figure 17:
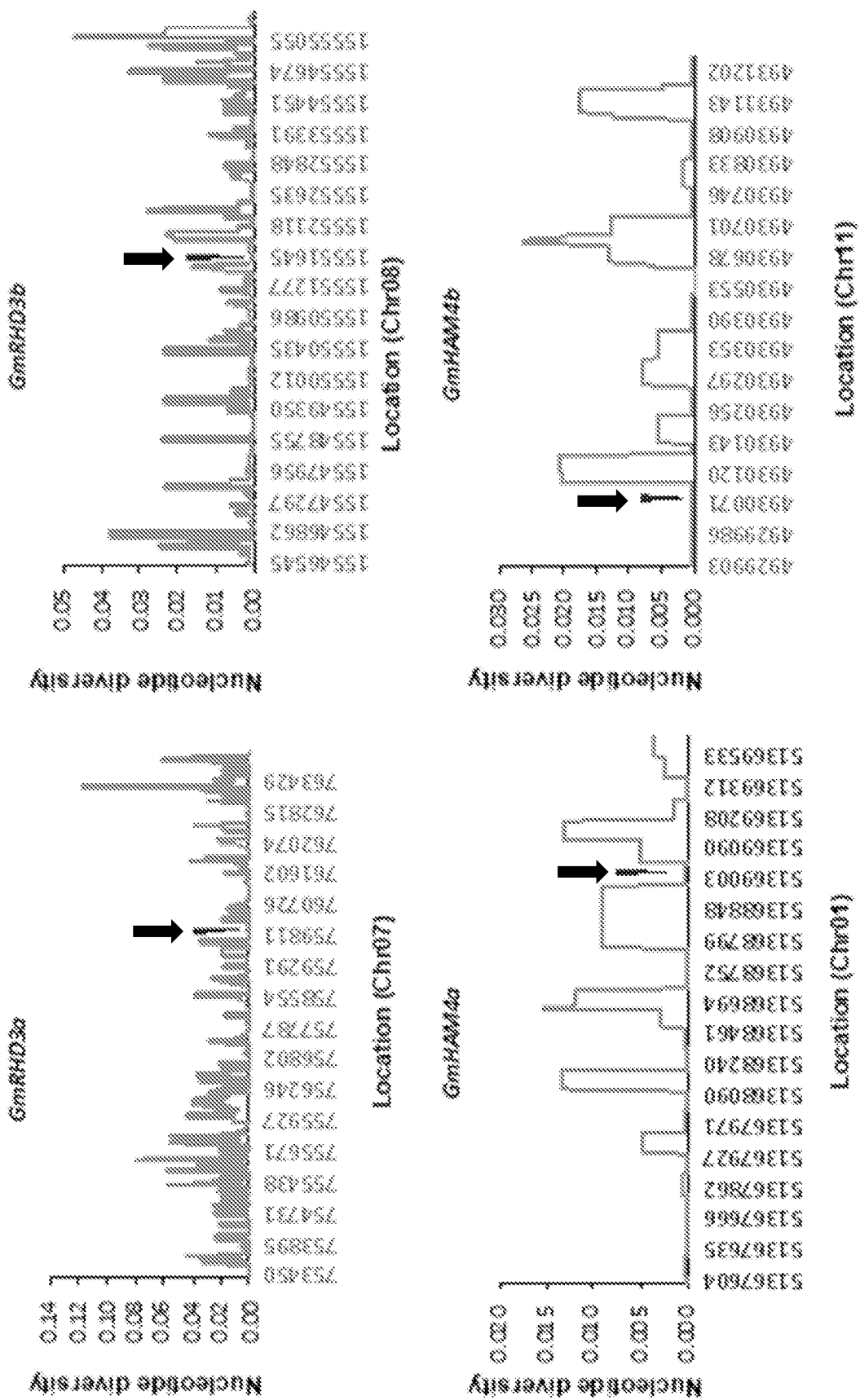

Sequence Conservation of Three Rhizobial tRFs, tRF Target Sites, and their Corresponding Sequences Among Different Legume-Rhizobial Partners To determine if rhizobial tRF-mediated host gene regulation is conserved across evolutionarily related legumes, sequence data from four legumes (soybean, common bean (*Phaseolus vulgaris*), *Medicago truncatula*, and *Lotus japonica*) and 12 *rhizobium* species was analyzed, as well as the GmRHD3a GmRHD3b, GmHAM4a GmHAM4b, and GmLRX5 sequences from soybean populations, with respect to compatible symbiotic interactions. As shown in FIGS. 17 and 18, among 699 soybean accessions, no sequence variation at the three tRF target sites across the five genes was found. Further, among the eight *B. japonicum* strains, no sequence variation at the three tRF sites within respective rhizobial tRNAs was detected. FIG. 19A-19C lists bacterial strains/species that conserve the three tRF target sites CAC, UCC, and CUG, with the thick vertical black bars indicating different *rhizobium* groups.

By contrast, sequences at the target sites diverged among the four legumes (data not shown). *Sinorhizobium meliloti* (Sm), *Mesorhizobium loti* (Ml), *Bradyrhizobium japonicum* (Bj) and *Rhizobium etli* (Re), are compatible *rhizobium* species often used to inoculate *Medicago truncatula* (Mtru), *Lotus japonicus* (Ljap), *Glycine max* (Gmax) and *Phaseolus vulgaris* (Pvul), respectively, in scientific research. Rhizobial DNA sequences (dubbed tRF orthologs) corresponding to Bj-tRF001, Bj-tRF002, and Bj-tRF003 from four *rhizobium* species and the sequences (target site orthologs) corresponding to the three tRF target sites from four legume species were assessed. The highest levels of sequence complementarities between any of the tRF orthologs and any of the target site orthologs were identified, with only the sequence complementarities of (1) Bj-tRF001 and Gmax & Pvul, (2) Bj-tRF002 and Gmax, and (3) Bj-tRF003 and Gmax predicted by psRNA Target to be sufficient for miRNA-guided cleavage. In particular, no orthologs of GmLRX5 were found in the other three legumes. The counterparts of the three rhizobial tRF sequences in respective tRNAs also showed interspecific divergence (data not shown).

Figure 20A:
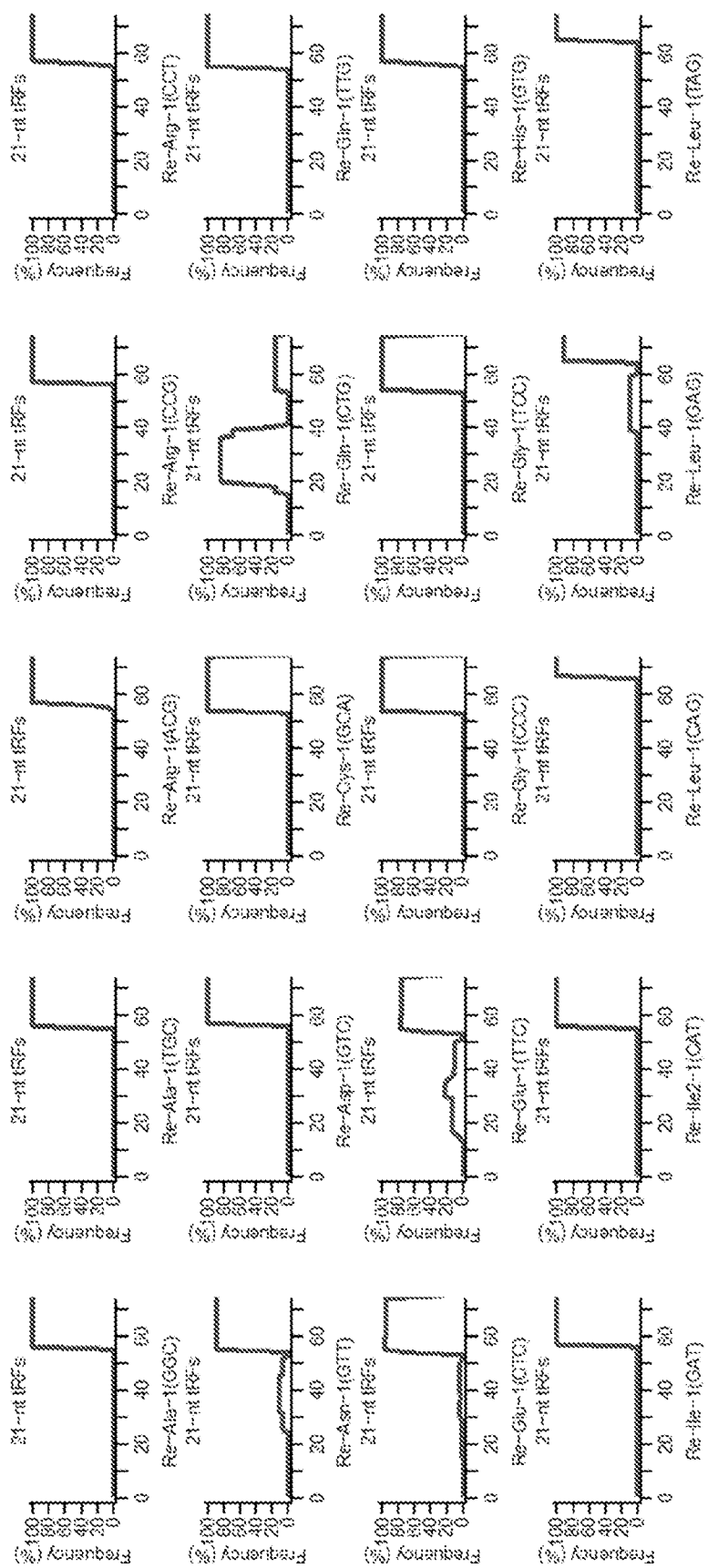
FIGS. 20A and 20B show graphical depictions of distribution and relative abundance data of 21-nt tRFs along rhizobial tRNAs in common bean nodules, with each x-axis representing nucleotide locations of a tRNA of *R. etli* strain CE3 pMP604 and each y-axis indicating the frequencies of individual nucleotides along the tRNA that are covered by the 21-nt tRFs derived from the tRNA in the common bean nodules induced by CE3 pMP604.
Figure 20B:
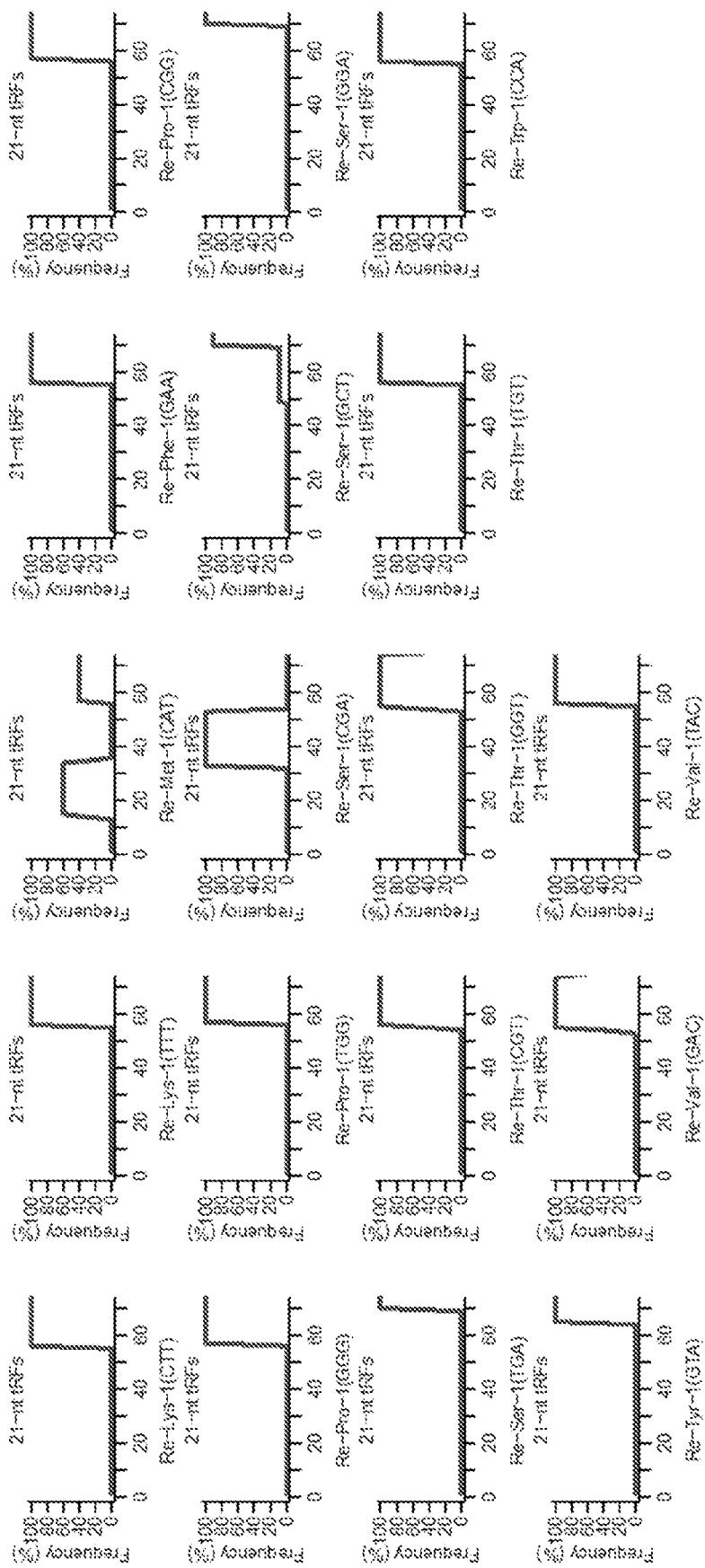

However, while PvRHD3 in common bean, the ortholog of GmRHD3a/3b, does have a tRF001 target site identical to that of GmRHD3a/3b, *Rhizobium etli*, a compatible symbiotic partner of common bean, does not have the *B. japonicum* Val-1-tRNA (CAC) from which tRF01 was derived. Using the small RNA data from the common bean nodules induced by a *R. etli* strain, 38 *R. etli* tRNAs were identified to have produced 21-nt tRFs. As shown in FIGS. 20A and 20B, these tRFs were primarily derived from the 3' ends of the tRNAs.

Ten different 21-nt tRFs, each with a relative abundance of >100 counts per million rhizobial small RNA reads in the common bean nodules, were predicted to target 14 common bean genes, including genes encoding a protein kinase, a GRAS transcription factor, and an APETALA2-like transcription factor that is thought to be involved in nodulation regulation (see Table 4).

TABLE 4

Rhizobial tRFs from *Rhizobium etli* and their potential targets in common bean.

| tRF-seq | tRNA | Gene Symbol | Annotation |
| --- | --- | --- | --- |
| SEQ ID NO: 34 | Met-CAT | AtPERK12, IGI1 | Protein kinase superfamily protein |
| SEQ ID NO: 35 | Ile-GAT | | P-loop containing nucleoside triphosphate hydrolases superfamily protein |
| SEQ ID NO: 36 | Gln-CTG | HSP70T-2 | heat-shock protein 70T-2 |
| SEQ ID NO: 37 | Met-CAT | BLH1, EDA29 | BEL1-like homeodomain 1 |
| SEQ ID NO: 38 | Met-CAT | ABCA1, AtABCA1 | ATP-binding cassette A1 |
| SEQ ID NO: 39 | Met-CAT | | Ubiquitin-like superfamily protein |
| SEQ ID NO: 40 | Ile-GAT | ATXIA, XIA | myosin XI A |
| SEQ ID NO: 41 | Pro-CGG | RGA, RGA1 | GRAS family transcription factor family protein |
| SEQ ID NO: 42 | Asn-GTT | | Pyridoxal-dependent decarboxylase family protein |
| SEQ ID NO: 43 | Trp-CCA | HEMA1 | Glutamyl-tRNA reductase family protein |
| SEQ ID NO: 44 | Val-TAC | AP2, FL1, FLO2 | Integrase-type DNA-binding superfamily protein |
| SEQ ID NO: 45 | Glu-TTC | | Zinc finger, C3HC4 type (RING finger) family protein |

TABLE 4-continued

Rhizobial tRFs from *Rhizobium etli* and their potential targets in common bean.

| tRF-seq | tRNA | Gene Symbol | Annotation |
|---|---|---|---|
| SEQ ID NO: 46 | Glu-TTC | ACL5 | S-adenosyl-L-methionine-dependent methyltransferases superfamily protein |
| SEQ ID NO: 47 | Met-CAT | KAN, KAN1 | Homeodomain-like superfamily protein |
| SEQ ID NO: 48 | Met-CAT | BLH1, EDA29 | BEL1-like homeodomain 1 |
| SEQ ID NO: 49 | Met-CAT |  | Ubiquitin-like superfamily protein |

Nevertheless, none of these 14 putative *R. etli* tRF targets in common bean are orthologs of the 25 targeted *B. japonicum* tRF targets in soybean (see Table 2).

The results support that, while the use of bacterial tRFs to target host genes appears to be conserved, the tRFs and their target genes may vary across species. Indeed, based on the data presented herein, the rhizobial-derived sequences and paired *R. etli* tRF gene targets of Table 3 above can be leveraged in the same fashion as described in connection with the *B. japonicum* tRFs/gene targets described herein. These findings, combined with the other studies presented herein, highlight the complexity of the regulatory network that occurs during the establishment of nodulation.

Accordingly, the data presented herein demonstrates that rhizobial tRFs are positive regulators of rhizobial infection and nodule formation in soybean and play an important role in balancing plant growth and symbiosis. In addition to the rhizobial tRFs identified herein, the other rhizobial tRFs identified in Table 2 are predicted to target soybean genes annotated to encode auxin receptors and efflux carriers, RING/U-box proteins, and protein kinases, which likely affects nodulation. Furthermore, the data supports that such cross-kingdom communications are likely common among symbiotic partners, but the nodes of rhizobial tRFs-host gene interactions appear to be diverse. These findings have exemplified the effectiveness of genome editing for enhancement of the nodulation capability of leguminous plants.

While various embodiments of compounds, transgenic plants/plant roots/plant cells, and methods hereof have been described in considerable detail, the embodiments are merely offered by way of non-limiting examples. Many variations and modifications of the embodiments described herein will be apparent to one of ordinary skill in the art in light of the disclosure. It will therefore be understood by those skilled in the art that various changes and modifications may be made, and equivalents may be substituted for elements thereof, without departing from the scope of the disclosure. Indeed, this disclosure is not intended to be exhaustive or too limiting. The scope of the disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that this description and the appended claims will encompass, all modifications and changes apparent to those of ordinary skill in the art based on this disclosure.

The invention claimed is:

1. A *Glycine max* plant, plant root, or plant cell comprising a recombinant polynucleotide construct encoding at least one or more small RNA fragments, wherein each small RNA fragment downregulates a target gene(s) of the *Glycine max* plant, plant root, or plant cell that are negative regulators of nodulation such that the *Glycine max* plant produces increased nodules when inoculated with a *Bradyrhizobium* or *Sinorhizobium* species or strain as compared to a corresponding *Glycine max* plant, root, or cell that does not comprise the recombinant polynucleotide construct, wherein:

(a) the target gene is GmRHD3a which encodes the amino acid sequence of SEQ ID NO: 80, GmRHD3b which encodes the amino acid sequence of SEQ ID NO: 81, GmHAM4a which encodes the amino acid sequence of SEQ ID NO: 82, GmHAM4b which encodes the amino acid sequence of SEQ ID NO: 83, or GmLRX5 which encodes the amino acid sequence of SEQ ID NO: 84, or (b) the target genes are GmRHD3a which encodes the amino acid sequence of SEQ ID NO: 80 and GmRHD3b which encodes the amino acid sequence of SEQ ID NO: 81, or GmHAM4a which encodes the amino acid sequence of SEQ ID NO: 83 and GmHAM4b which encodes the amino acid sequence of SEQ ID NO: 83.

2. The *Glycine max* plant, plant root, or plant cell of claim 1, wherein each small RNA fragment has a nucleotide sequence selected from the group consisting of SEQ ID NOs: 1-3 and SEQ ID NOs: 50-70.

3. The *Glycine max* plant, plant root, or plant cell of claim 2, wherein the nucleotide sequence of the one or more small RNA fragments is SEQ ID NO: 1, SEQ ID NO: 2, or SEQ ID NO: 3.

4. A method for increasing nodulation activity in a *Glycine max* plant, plant root, or plant cell the method comprising:

repressing or downregulating expression of target gene(s) of a *Glycine max* plant, plant root, or plant cell using small RNA fragments and/or a CRISPR-Cas9 vector, each target gene(s) being a negative regulator of nodulation in the *Glycine max* plant, plant root, or plant cell; and then inoculating, or having inoculated, the modified *Glycine max* plant, plant root, or plant cell with at least one *Bradyrhizobium* or *Sinorhizobium* species or strain;

wherein (a) the target gene is GmRHD3a which encodes the amino acid sequence of SEQ ID NO: 80, GmRHD3b which encodes the amino acid sequence of SEQ ID NO: 81, GmHAM4a which encodes the amino acid sequence of SEQ ID NO: 82, GmHAM4b which encodes the amino acid sequence of SEQ ID NO: 83, or GmLRX5 which encodes the amino acid sequence of SEQ ID NO: 84, or (b) the target genes are GmRHD3a which encodes the amino acid sequence of SEQ ID NO: 80 and GmRHD3b which encodes the amino acid sequence of SEQ ID NO: 81, or GmHAM4a which encodes the amino acid sequence of SEQ ID NO: 83 and GmHAM4b which encodes the amino acid sequence of SEQ ID NO: 83.

5. The method of claim 4, wherein the repressing or downregulating expression of the target gene(s) comprises introducing and expressing a polynucleotide construct encoding one or more small RNA fragments in the *Glycine max* plant, plant root, or plant cell that each downregulate the target gene(s).

6. The method of claim 4, wherein the repressing or downregulating expression of the target gene(s) comprises constructing a CRISPR-Cas9 vector to silence the target gene(s) and expressing the vector in the *Glycine max* plant, plant root, or plant cell.

7. The method of claim 6, wherein the target gene(s) is/are:

GmRHD3a, GmRHD3b, or both, and the CRISPR-Cas9 vector comprises the nucleotide sequence of SEQ ID Nos: 4 and 5;

GmHAM4a, GmHAM4b, or both, and the CRISPR-Cas9 vector comprises the nucleotide sequence of SEQ ID NOs: 6 and 7; or GmLRX5 and the CRISPR-Cas9 vector comprises the nucleotide sequence of SEQ ID NOs: 8 and 9.

8. The method of claim 5, wherein each of the small RNA fragments has a nucleotide sequence selected from the group consisting of: SEQ ID NOs: 1-3 and SEQ ID NOs: 34-70.

9. The method of claim 4, wherein the at least one *Bradyrhizobium* or *Sinorhizobium* species or strain is engineered to exhibit upregulated expression of one or more transfer ribonucleic acid (tRNA) sequences as compared to production of the one or more tRNA sequences in a corresponding wild-type *Bradyrhizobium* or *Sinorhizobium* species or strain, wherein the tRNA sequences can be cleaved in planta to result in one or more tRNA-derived fragments (tRFs).

10. The method of claim 4, wherein the repressing or downregulating expression of the one or more target genes comprises:

introducing and expressing in the *Glycine max* plant, plant root, or plant cell a polynucleotide construct encoding one or more small RNA fragments that each downregulate the target gene(s); and/or expressing a CRISPR-Cas9 vector in the *Glycine max* plant, plant root, or plant cell that is constructed to silence the target gene(s).

* * * * *

SEQUENCE LISTING

```
<160> NUMBER OF SEQ ID NOS: 84

<210> SEQ ID NO 1
<211> LENGTH: 21
<212> TYPE: RNA
<213> ORGANISM: Bradyrhizobium japonicum

<400> SEQUENCE: 1
cgaucccuug ugcgcccacc a                                          21

<210> SEQ ID NO 2
<211> LENGTH: 21
<212> TYPE: RNA
<213> ORGANISM: Bradyrhizobium japonicum

<400> SEQUENCE: 2
cgauucccuu cacccgcucc a                                          21

<210> SEQ ID NO 3
<211> LENGTH: 21
<212> TYPE: RNA
```

-continued

<213> ORGANISM: Bradyrhizobium japonicum

<400> SEQUENCE: 3 ugggaaugg uguaacggua g                                               21

<210> SEQ ID NO 4
<211> LENGTH: 23
<212> TYPE: DNA
<213> ORGANISM: Artificial Sequence
<220> FEATURE:
<223> OTHER INFORMATION: oligonucleotides for targeting a RHD3 gene
      (RHD3_pSC_F)

<400> SEQUENCE: 4
attgaggtga agttggctga atg                                            23

<210> SEQ ID NO 5
<211> LENGTH: 23
<212> TYPE: DNA
<213> ORGANISM: Artificial Sequence
<220> FEATURE:
<223> OTHER INFORMATION: oligonucleotides for targeting a RHD3 gene
      (RHD3_pSC_B)

<400> SEQUENCE: 5
aaccattcag ccaacttcac ctc                                            23

<210> SEQ ID NO 6
<211> LENGTH: 23
<212> TYPE: DNA
<213> ORGANISM: Artificial Sequence
<220> FEATURE:
<223> OTHER INFORMATION: oligonucleotides for targeting a HAM4 gene
      (HAM4_pSC_F)

<400> SEQUENCE: 6
attgcctgtg gggatgaggg aac                                            23

<210> SEQ ID NO 7
<211> LENGTH: 23
<212> TYPE: DNA
<213> ORGANISM: Artificial Sequence
<220> FEATURE:
<223> OTHER INFORMATION: oligonucleotides for targeting a HAM4 gene
      (HAM4_pSC_B)

<400> SEQUENCE: 7
aacgttccct catccccaca ggc                                            23

<210> SEQ ID NO 8
<211> LENGTH: 23
<212> TYPE: DNA
<213> ORGANISM: Artificial Sequence
<220> FEATURE:
<223> OTHER INFORMATION: oligonucleotides for targeting a LRX5 gene
      (LRX5_pSC-F)

<400> SEQUENCE: 8
attgttgaaa ctgctctacg aac                                            23

<210> SEQ ID NO 9
<211> LENGTH: 23
<212> TYPE: DNA
<213> ORGANISM: Artificial Sequence
<220> FEATURE:
<223> OTHER INFORMATION: oligonucleotides for targeting a LRX5 gene
      (LRX5_pSC-B)

```
<400> SEQUENCE: 9
aacgttcgta gagcagtttc aac                                          23

<210> SEQ ID NO 10
<211> LENGTH: 21
<212> TYPE: DNA
<213> ORGANISM: Bradyrhizobium japonicum

<400> SEQUENCE: 10
caaatcctat ccccgcaacc a                                            21

<210> SEQ ID NO 11
<211> LENGTH: 21
<212> TYPE: DNA
<213> ORGANISM: Bradyrhizobium japonicum

<400> SEQUENCE: 11
caaatcctct cgctccgacc a                                            21

<210> SEQ ID NO 12
<211> LENGTH: 21
<212> TYPE: DNA
<213> ORGANISM: Bradyrhizobium japonicum

<400> SEQUENCE: 12
caatcctgtc tggcagcacc a                                            21

<210> SEQ ID NO 13
<211> LENGTH: 21
<212> TYPE: DNA
<213> ORGANISM: Bradyrhizobium japonicum

<400> SEQUENCE: 13
cgaatccagc tgccccgacc a                                            21

<210> SEQ ID NO 14
<211> LENGTH: 21
<212> TYPE: DNA
<213> ORGANISM: Bradyrhizobium japonicum

<400> SEQUENCE: 14
cgaatccagg ttccccagcc a                                            21

<210> SEQ ID NO 15
<211> LENGTH: 21
<212> TYPE: DNA
<213> ORGANISM: Bradyrhizobium japonicum

<400> SEQUENCE: 15
cgaatcccac tctctccgcc a                                            21

<210> SEQ ID NO 16
<211> LENGTH: 21
<212> TYPE: DNA
<213> ORGANISM: Bradyrhizobium japonicum

<400> SEQUENCE: 16
cgaatccctc cctctccgcc a                                            21

<210> SEQ ID NO 17
<211> LENGTH: 21
<212> TYPE: DNA
```

<213> ORGANISM: Bradyrhizobium japonicum

<400> SEQUENCE: 17
cgaatcctgc cactccgacc a                           21

<210> SEQ ID NO 18
<211> LENGTH: 21
<212> TYPE: DNA
<213> ORGANISM: Bradyrhizobium japonicum

<400> SEQUENCE: 18
cgaatcgtgt cgggtgcgcc a                           21

<210> SEQ ID NO 19
<211> LENGTH: 21
<212> TYPE: DNA
<213> ORGANISM: Bradyrhizobium japonicum

<400> SEQUENCE: 19
cgagcccacc caactgtacc a                           21

<210> SEQ ID NO 20
<211> LENGTH: 21
<212> TYPE: DNA
<213> ORGANISM: Bradyrhizobium japonicum

<400> SEQUENCE: 20
cgagccctgc cactcctgcc a                           21

<210> SEQ ID NO 21
<211> LENGTH: 21
<212> TYPE: DNA
<213> ORGANISM: Bradyrhizobium japonicum

<400> SEQUENCE: 21
cgagtcatcc cgggatcgcc a                           21

<210> SEQ ID NO 22
<211> LENGTH: 21
<212> TYPE: DNA
<213> ORGANISM: Bradyrhizobium japonicum

<400> SEQUENCE: 22
cgagtccctc cgagcgcacc a                           21

<210> SEQ ID NO 23
<211> LENGTH: 21
<212> TYPE: DNA
<213> ORGANISM: Bradyrhizobium japonicum

<400> SEQUENCE: 23
cgatcccgtc tggctccacc a                           21

<210> SEQ ID NO 24
<211> LENGTH: 21
<212> TYPE: DNA
<213> ORGANISM: Bradyrhizobium japonicum

<400> SEQUENCE: 24
cgatccctgt cgtgcccacc a                           21

<210> SEQ ID NO 25
<211> LENGTH: 21

```
<212> TYPE: DNA
<213> ORGANISM: Bradyrhizobium japonicum

<400> SEQUENCE: 25
cgatcccttg tgcgcccacc a                                         21

<210> SEQ ID NO 26
<211> LENGTH: 21
<212> TYPE: DNA
<213> ORGANISM: Bradyrhizobium japonicum

<400> SEQUENCE: 26
cgattccctt cacccgctcc a                                         21

<210> SEQ ID NO 27
<211> LENGTH: 21
<212> TYPE: DNA
<213> ORGANISM: Bradyrhizobium japonicum

<400> SEQUENCE: 27
cgattccctt cgcccgctcc a                                         21

<210> SEQ ID NO 28
<211> LENGTH: 21
<212> TYPE: DNA
<213> ORGANISM: Bradyrhizobium japonicum

<400> SEQUENCE: 28
cgattccgcc cctgggcacc a                                         21

<210> SEQ ID NO 29
<211> LENGTH: 21
<212> TYPE: DNA
<213> ORGANISM: Bradyrhizobium japonicum

<400> SEQUENCE: 29
gcgctcgtgg cggaactggt a                                         21

<210> SEQ ID NO 30
<211> LENGTH: 21
<212> TYPE: DNA
<213> ORGANISM: Bradyrhizobium japonicum

<400> SEQUENCE: 30
gcgggtgtag ctcagtggta g                                         21

<210> SEQ ID NO 31
<211> LENGTH: 21
<212> TYPE: DNA
<213> ORGANISM: Bradyrhizobium japonicum

<400> SEQUENCE: 31
tcctcggtag ctcagcggta g                                         21

<210> SEQ ID NO 32
<211> LENGTH: 21
<212> TYPE: DNA
<213> ORGANISM: Bradyrhizobium japonicum

<400> SEQUENCE: 32
tggggaatgg tgtaacggta g                                         21

<210> SEQ ID NO 33
```

```
<211> LENGTH: 21
<212> TYPE: DNA
<213> ORGANISM: Bradyrhizobium japonicum

<400> SEQUENCE: 33
ttggtagacg caagggactt a                                              21

<210> SEQ ID NO 34
<211> LENGTH: 21
<212> TYPE: DNA
<213> ORGANISM: Rhizobium etli

<400> SEQUENCE: 34
caaatccctc ctccgctacc a                                              21

<210> SEQ ID NO 35
<211> LENGTH: 21
<212> TYPE: DNA
<213> ORGANISM: Rhizobium etli

<400> SEQUENCE: 35
caagtcttcc cgggcccacc a                                              21

<210> SEQ ID NO 36
<211> LENGTH: 21
<212> TYPE: DNA
<213> ORGANISM: Rhizobium etli

<400> SEQUENCE: 36
cgagtccagg ttccccagcc a                                              21

<210> SEQ ID NO 37
<211> LENGTH: 21
<212> TYPE: DNA
<213> ORGANISM: Rhizobium etli

<400> SEQUENCE: 37
agtaggtcag agcagaggaa t                                              21

<210> SEQ ID NO 38
<211> LENGTH: 21
<212> TYPE: DNA
<213> ORGANISM: Rhizobium etli

<400> SEQUENCE: 38
agtaggtcag agcagaggaa t                                              21

<210> SEQ ID NO 39
<211> LENGTH: 21
<212> TYPE: DNA
<213> ORGANISM: Rhizobium etli

<400> SEQUENCE: 39
agtaggtcag agcagaggaa t                                              21

<210> SEQ ID NO 40
<211> LENGTH: 21
<212> TYPE: DNA
<213> ORGANISM: Rhizobium etli

<400> SEQUENCE: 40
caagtcttcc cgggcccacc a                                              21
```

```
<210> SEQ ID NO 41
<211> LENGTH: 21
<212> TYPE: DNA
<213> ORGANISM: Rhizobium etli

<400> SEQUENCE: 41
cgaatcactc cactccgacc a                                              21

<210> SEQ ID NO 42
<211> LENGTH: 21
<212> TYPE: DNA
<213> ORGANISM: Rhizobium etli

<400> SEQUENCE: 42
cgaatccggc ccggggagcc a                                              21

<210> SEQ ID NO 43
<211> LENGTH: 21
<212> TYPE: DNA
<213> ORGANISM: Rhizobium etli

<400> SEQUENCE: 43
cgagccctgc tgcccctgcc a                                              21

<210> SEQ ID NO 44
<211> LENGTH: 21
<212> TYPE: DNA
<213> ORGANISM: Rhizobium etli

<400> SEQUENCE: 44
cgagtctctc atcgcccacc a                                              21

<210> SEQ ID NO 45
<211> LENGTH: 21
<212> TYPE: DNA
<213> ORGANISM: Rhizobium etli

<400> SEQUENCE: 45
gattttcatt ctgtaaagag g                                              21

<210> SEQ ID NO 46
<211> LENGTH: 21
<212> TYPE: DNA
<213> ORGANISM: Rhizobium etli

<400> SEQUENCE: 46
gattttcatt ctgtaaagag g                                              21

<210> SEQ ID NO 47
<211> LENGTH: 21
<212> TYPE: DNA
<213> ORGANISM: Rhizobium etli

<400> SEQUENCE: 47
gtaggtcaga gcagaggaat c                                              21

<210> SEQ ID NO 48
<211> LENGTH: 21
<212> TYPE: DNA
<213> ORGANISM: Rhizobium etli

<400> SEQUENCE: 48
gtaggtcaga gcagaggaat c                                              21
```

```
<210> SEQ ID NO 49
<211> LENGTH: 21
<212> TYPE: DNA
<213> ORGANISM: Rhizobium etli

<400> SEQUENCE: 49
gtaggtcaga gcagaggaat c                                              21

<210> SEQ ID NO 50
<211> LENGTH: 21
<212> TYPE: RNA
<213> ORGANISM: Bradyrhizobium japonicum

<400> SEQUENCE: 50
caaauccuau ccccgcaacc a                                              21

<210> SEQ ID NO 51
<211> LENGTH: 21
<212> TYPE: RNA
<213> ORGANISM: Bradyrhizobium japonicum

<400> SEQUENCE: 51
caaauccucu cgcuccgacc a                                              21

<210> SEQ ID NO 52
<211> LENGTH: 21
<212> TYPE: RNA
<213> ORGANISM: Bradyrhizobium japonicum

<400> SEQUENCE: 52
caauccuguc uggcagcacc a                                              21

<210> SEQ ID NO 53
<211> LENGTH: 21
<212> TYPE: RNA
<213> ORGANISM: Bradyrhizobium japonicum

<400> SEQUENCE: 53
cgaauccagc ugccccgacc a                                              21

<210> SEQ ID NO 54
<211> LENGTH: 21
<212> TYPE: RNA
<213> ORGANISM: Bradyrhizobium japonicum

<400> SEQUENCE: 54
cgaauccagg uuccccagcc a                                              21

<210> SEQ ID NO 55
<211> LENGTH: 21
<212> TYPE: RNA
<213> ORGANISM: Bradyrhizobium japonicum

<400> SEQUENCE: 55
cgaaucccac ucucuccgcc a                                              21

<210> SEQ ID NO 56
<211> LENGTH: 21
<212> TYPE: RNA
<213> ORGANISM: Bradyrhizobium japonicum

<400> SEQUENCE: 56
cgaaucccuc ccucuccgcc a                                              21
```

<210> SEQ ID NO 57
<211> LENGTH: 21
<212> TYPE: RNA
<213> ORGANISM: Bradyrhizobium japonicum

<400> SEQUENCE: 57
cgaauccugc cacuccgacc a                                              21

<210> SEQ ID NO 58
<211> LENGTH: 21
<212> TYPE: RNA
<213> ORGANISM: Bradyrhizobium japonicum

<400> SEQUENCE: 58
cgaaucgugu cgggugcgcc a                                              21

<210> SEQ ID NO 59
<211> LENGTH: 21
<212> TYPE: RNA
<213> ORGANISM: Bradyrhizobium japonicum

<400> SEQUENCE: 59
cgagcccacc caacuguacc a                                              21

<210> SEQ ID NO 60
<211> LENGTH: 21
<212> TYPE: RNA
<213> ORGANISM: Bradyrhizobium japonicum

<400> SEQUENCE: 60
cgagcccugc cacuccugcc a                                              21

<210> SEQ ID NO 61
<211> LENGTH: 21
<212> TYPE: RNA
<213> ORGANISM: Bradyrhizobium japonicum

<400> SEQUENCE: 61
cgagucaucc cgggaucgcc a                                              21

<210> SEQ ID NO 62
<211> LENGTH: 21
<212> TYPE: RNA
<213> ORGANISM: Bradyrhizobium japonicum

<400> SEQUENCE: 62
cgagucccuc cgagcgcacc a                                              21

<210> SEQ ID NO 63
<211> LENGTH: 21
<212> TYPE: RNA
<213> ORGANISM: Bradyrhizobium japonicum

<400> SEQUENCE: 63
cgaucccguc uggcuccacc a                                              21

<210> SEQ ID NO 64
<211> LENGTH: 21
<212> TYPE: RNA
<213> ORGANISM: Bradyrhizobium japonicum

<400> SEQUENCE: 64
cgaucccugu cgugcccacc a                                              21

<210> SEQ ID NO 65
<211> LENGTH: 21
<212> TYPE: RNA
<213> ORGANISM: Bradyrhizobium japonicum

<400> SEQUENCE: 65
cgauucccuu cgcccgcucc a                                              21

<210> SEQ ID NO 66
<211> LENGTH: 21
<212> TYPE: RNA
<213> ORGANISM: Bradyrhizobium japonicum

<400> SEQUENCE: 66
cgauuccgcc ccugggcacc a                                              21

<210> SEQ ID NO 67
<211> LENGTH: 21
<212> TYPE: RNA
<213> ORGANISM: Bradyrhizobium japonicum

<400> SEQUENCE: 67
gcgcucgugg cggaacuggu a                                              21

<210> SEQ ID NO 68
<211> LENGTH: 21
<212> TYPE: RNA
<213> ORGANISM: Bradyrhizobium japonicum

<400> SEQUENCE: 68
gcggguguag cucaguggua g                                              21

<210> SEQ ID NO 69
<211> LENGTH: 21
<212> TYPE: RNA
<213> ORGANISM: Bradyrhizobium japonicum

<400> SEQUENCE: 69
uccucgguag cucagcggua g                                              21

<210> SEQ ID NO 70
<211> LENGTH: 21
<212> TYPE: RNA
<213> ORGANISM: Bradyrhizobium japonicum

<400> SEQUENCE: 70
uugguagacg caagggacuu a                                              21

<210> SEQ ID NO 71
<211> LENGTH: 75
<212> TYPE: RNA
<213> ORGANISM: Bradyrhizobium japonicum

<400> SEQUENCE: 71
gggcgcauag cucagcggga gagcguuccc uucacacggg agagguccaa gguucgaucc     60
cuugugcgcc cacca                                                     75

<210> SEQ ID NO 72
<211> LENGTH: 74
<212> TYPE: RNA
<213> ORGANISM: Bradyrhizobium japonicum

<400> SEQUENCE: 72
gcggguguag cucaauggua gagcagcagc cuuccaagcu gaauacgagg guucgauucc    60
cuucacccgc ucca    74

<210> SEQ ID NO 73
<211> LENGTH: 74
<212> TYPE: RNA
<213> ORGANISM: Bradyrhizobium japonicum

<400> SEQUENCE: 73
uggggaaugg uguaacggua gcacaacaga cucugacucu guuugucuug guucgaaucc    60
agguucccca gcca    74

<210> SEQ ID NO 74
<211> LENGTH: 33
<212> TYPE: DNA
<213> ORGANISM: Artificial Sequence
<220> FEATURE:
<223> OTHER INFORMATION: a forward primer for an overexpression construct for target gene RHD3b

<400> SEQUENCE: 74
gcgcgtcgac atggcaaata gtgagacttg ttg    33

<210> SEQ ID NO 75
<211> LENGTH: 34
<212> TYPE: DNA
<213> ORGANISM: Artificial Sequence
<220> FEATURE:
<223> OTHER INFORMATION: a reverse primer for an overexpression construct for target gene RHD3b

<400> SEQUENCE: 75
gcgctctaga ctactcatct tttaatggac ttgc    34

<210> SEQ ID NO 76
<211> LENGTH: 34
<212> TYPE: DNA
<213> ORGANISM: Artificial Sequence
<220> FEATURE:
<223> OTHER INFORMATION: a forward primer for an overexpression construct for target gene HAM4a

<400> SEQUENCE: 76
ttgcctcgag atgagagttc ccgttccctc atcc    34

<210> SEQ ID NO 77
<211> LENGTH: 35
<212> TYPE: DNA
<213> ORGANISM: Artificial Sequence
<220> FEATURE:
<223> OTHER INFORMATION: a reverse primer for an overexpression construct for target gene HAM4a

<400> SEQUENCE: 77
gcttggtacc ctaacagcgc catgctgacg tggca    35

<210> SEQ ID NO 78
<211> LENGTH: 35
<212> TYPE: DNA
<213> ORGANISM: Artificial Sequence
<220> FEATURE:
<223> OTHER INFORMATION: a forward primer for an overexpression construct for target gene LRX5

```
<400> SEQUENCE: 78
gcgcgtcgac atgatgatga tgatgaagaa gaagg                              35

<210> SEQ ID NO 79
<211> LENGTH: 35
<212> TYPE: DNA
<213> ORGANISM: Artificial Sequence
<220> FEATURE:
<223> OTHER INFORMATION: a reverse primer for an overexpression
      construct for target gene LRX5

<400> SEQUENCE: 79
gcaatctaga ctaataaaag ggtggtggtg gaggc                              35

<210> SEQ ID NO 80
<211> LENGTH: 808
<212> TYPE: PRT
<213> ORGANISM: Glycine max

<400> SEQUENCE: 80
```

Met Ala Asn Ser Glu Thr Cys Cys Ser Thr Gln Leu Ile Asp Gly Asp
1               5                   10                  15

Gly Thr Phe Asn Val Phe Gly Val Glu Asn Phe Met Lys Glu Val Lys
                20                  25                  30

Leu Ala Glu Cys Gly Leu Ser Tyr Ala Val Val Ser Ile Met Gly Pro
            35                  40                  45

Gln Ser Ser Gly Lys Ser Thr Leu Leu Asn His Leu Phe Gly Thr Asn
        50                  55                  60

Phe Arg Glu Met Asp Ala Phe Lys Gly Arg Ser Gln Thr Thr Lys Gly
65                  70                  75                  80

Ile Trp Met Ala Arg Cys Ala Gly Ile Glu Pro Cys Thr Leu Val Met
                85                  90                  95

Asp Leu Glu Gly Thr Asp Gly Arg Glu Arg Gly Glu Asp Asp Thr Ala
            100                 105                 110

Phe Glu Lys Gln Ser Ala Leu Phe Ala Leu Ala Val Ser Asp Ile Val
        115                 120                 125

Leu Ile Asn Met Trp Cys His Asp Ile Gly Arg Glu Gln Ala Ala Asn
130                 135                 140

Lys Pro Leu Leu Lys Thr Val Phe Gln Val Met Met Arg Leu Phe Ser
145                 150                 155                 160

Pro Arg Lys Thr Thr Leu Leu Phe Val Ile Arg Asp Lys Thr Arg Thr
                165                 170                 175

Pro Leu Glu Asn Leu Glu Pro Val Leu Arg Glu Asp Ile Gln Lys Ile
            180                 185                 190

Trp Asp Ser Val Pro Lys Pro Gln Ala His Lys Glu Thr Pro Leu Ser
        195                 200                 205

Glu Phe Phe Asn Val Glu Val Val Ala Leu Ser Ser Tyr Glu Glu Lys
210                 215                 220

Glu Glu Gln Phe Lys Asp Gln Val Ala Ser Leu Arg Gln Arg Phe His
225                 230                 235                 240

His Ser Ile Ala Pro Gly Gly Leu Ala Gly Asp Arg Arg Gly Val Val
                245                 250                 255

Pro Ala Ser Gly Phe Ser Phe Ser Ser Glu His Ile Trp Lys Val Ile
            260                 265                 270

Lys Glu Asn Lys Asp Leu Asp Leu Pro Ala His Lys Val Met Val Ala
        275                 280                 285

```
Thr Val Arg Cys Glu Glu Ile Ala Asn Glu Lys Tyr Val Ser Phe Val
    290                 295                 300

Ala Asn Glu Asp Trp Cys Gln Leu Glu Glu Ala Val Gln Ser Gly Pro
305                 310                 315                 320

Ile Pro Gly Phe Gly Lys Lys Leu Ser Ser Leu Leu Asp Ile Cys Phe
                325                 330                 335

Ser Glu Tyr Asp Ala Glu Ala Thr Tyr Phe Asp Glu Gly Val Arg Ser
            340                 345                 350

Ser Lys Gln Lys Gln Leu Gln Glu Lys Leu Phe Gln Leu Val Gln Pro
        355                 360                 365

Ala Phe Gln Ser Ala Leu Gly His Ile Arg Ser Gly Thr Leu Asp Lys
    370                 375                 380

Phe Lys Glu Ala Phe Asp Lys Thr Leu Lys Gly Gly Glu Gly Phe Ser
385                 390                 395                 400

Val Ala Ala Asn Asn Cys Ile Gly Ser Cys Met Val Gln Phe Asp Glu
                405                 410                 415

Ala Cys Thr Asp Val Val Ile Glu Gln Thr Asn Trp Asp Thr Ser Lys
            420                 425                 430

Val Arg Glu Lys Leu Leu Arg Asp Ile Asp Ala His Val Ala Thr Val
        435                 440                 445

Arg Ala Thr Lys Ile Ser Glu Leu Thr Ser Ser Tyr Glu Glu Lys Leu
    450                 455                 460

Lys Gln Ala Leu Ser Gly Pro Val Glu Ala Leu Leu Asp Gly Ala Asn
465                 470                 475                 480

Ser Asp Thr Trp Pro Ser Ile Arg Asn Leu Phe Arg Arg Glu Thr Glu
                485                 490                 495

Ser Ala Val Ser Gly Phe Ser Ala Ala Leu Thr Gly Phe Asp Met Asp
            500                 505                 510

Glu Glu Thr Arg Gln Lys Ile Ile Leu Ser Leu Glu Asp Tyr Ala Arg
        515                 520                 525

Gly Leu Val Glu Gly Lys Ala Arg Glu Glu Ala Gly Arg Val Leu Ile
    530                 535                 540

Arg Met Lys Asp Arg Phe Thr Met Leu Phe Ser His Asp Ser Asp Ser
545                 550                 555                 560

Met Pro Arg Val Trp Thr Gly Lys Glu Asp Ile Arg Ala Ile Thr Lys
                565                 570                 575

Thr Ala Arg Ser Ser Ser Leu Lys Leu Leu Ser Val Met Ala Ala Ile
            580                 585                 590

Arg Leu Asp Asp Asp Thr Asp Asn Ile Glu Lys Val Leu Ala Val
        595                 600                 605

Ala Leu Val Asp Ser Ser Pro Asn Ser Asn Ala Thr Arg Ser Met Thr
    610                 615                 620

Met Val Asp Pro Leu Ala Ser Ser Ser Trp Glu Gln Val Ser Ser Ser
625                 630                 635                 640

Lys Thr Leu Ile Thr Pro Val Gln Cys Lys Ser Leu Trp Arg Gln Phe
                645                 650                 655

Lys Thr Glu Thr Glu Tyr Ser Val Ser Gln Ala Ile Ser Ala Gln Glu
            660                 665                 670

Ala Asn Lys Arg Asn Asn Asn Trp Leu Pro Pro Trp Ala Ile Val
    675                 680                 685

Ala Leu Val Ile Leu Gly Phe Asn Glu Phe Met Thr Leu Leu Arg Asn
        690                 695                 700
```

-continued

```
Pro Leu Tyr Leu Gly Val Ile Phe Val Gly Phe Leu Leu Ile Lys Ala
705                 710                 715                 720

Leu Trp Val Gln Leu Asp Val Ser Gly Glu Phe Arg Asn Gly Ala Leu
                725                 730                 735

Pro Gly Ile Ile Ser Leu Ser Ser Lys Phe Ile Pro Thr Ile Met Asn
                740                 745                 750

Leu Met Lys Lys Leu Ala Glu Glu Gly Gln Asn Pro Ala Ala Asn Asn
                755                 760                 765

Pro Gln Arg Thr Pro Ser Lys Ser Ser Tyr Asn Glu Gly His Ala Val
                770                 775                 780

Ser Ser Ser Ala Ser Ser Asn Leu Thr Arg Leu Asp Asn Gly Thr Glu
785                 790                 795                 800

Tyr Ala Ser Pro Leu Lys Asp Asp
                805

<210> SEQ ID NO 81
<211> LENGTH: 808
<212> TYPE: PRT
<213> ORGANISM: Glycine max

<400> SEQUENCE: 81

Met Ala Asn Ser Glu Thr Cys Cys Ser Thr Gln Leu Ile Asp Gly Asp
1               5                   10                  15

Gly Thr Phe Asn Val Ser Gly Leu Glu Ser Phe Met Lys Glu Val Lys
                20                  25                  30

Leu Ala Glu Cys Gly Leu Ser Tyr Ala Val Val Ser Ile Met Gly Pro
            35                  40                  45

Gln Ser Ser Gly Lys Ser Thr Leu Leu Asn Asn Leu Phe Gly Thr Asn
50                  55                  60

Phe Arg Glu Met Asp Ala Phe Lys Gly Arg Ser Gln Thr Thr Lys Gly
65                  70                  75                  80

Ile Trp Met Ala Arg Cys Ala Asp Ile Glu Pro Cys Thr Leu Val Met
                85                  90                  95

Asp Leu Glu Gly Thr Asp Gly Arg Glu Arg Gly Glu Asp Asp Thr Ala
                100                 105                 110

Phe Glu Lys Gln Ser Ala Leu Phe Ala Leu Ala Val Ser Asp Ile Val
            115                 120                 125

Leu Ile Asn Met Trp Cys His Asp Ile Gly Arg Glu Gln Ala Ala Asn
            130                 135                 140

Lys Pro Leu Leu Lys Thr Val Phe Gln Val Met Met Arg Leu Phe Ser
145                 150                 155                 160

Pro Arg Lys Thr Thr Leu Leu Phe Val Ile Arg Asp Lys Thr Arg Thr
                165                 170                 175

Pro Leu Glu Asn Leu Glu Pro Val Leu Arg Glu Asp Ile Gln Lys Ile
                180                 185                 190

Trp Asp Ser Val Pro Lys Pro Gln Ala His Lys Glu Thr Pro Leu Ser
            195                 200                 205

Glu Phe Phe Asn Val Glu Val Val Ala Leu Ser Ser Tyr Glu Glu Lys
210                 215                 220

Glu Glu Gln Phe Lys Glu Gln Val Ala Ser Leu Gln Lys Arg Phe His
225                 230                 235                 240

His Ser Ile Ala Pro Gly Gly Leu Ala Gly Asp Arg Arg Gly Val Val
                245                 250                 255

Pro Ala Ser Gly Phe Ser Phe Ser Glu His Ile Trp Lys Val Ile
                260                 265                 270
```

```
Lys Glu Asn Lys Asp Leu Asp Leu Pro Ala His Lys Val Met Val Ala
            275                 280                 285

Thr Val Arg Cys Glu Glu Ile Ala Asn Glu Lys Tyr Ala Ser Phe Val
    290                 295                 300

Ala Asn Glu Asp Trp Cys Gln Leu Glu Glu Ala Val Gln Ser Gly Pro
305                 310                 315                 320

Ile Pro Gly Phe Gly Lys Lys Leu Ser Ser Leu Leu Asp Thr Cys Phe
                325                 330                 335

Ser Glu Tyr Asp Ala Glu Ala Thr Tyr Phe Asp Glu Gly Val Arg Ser
                340                 345                 350

Ser Lys Gln Lys Gln Leu Gln Glu Lys Leu Phe Gln Leu Val Gln Pro
                355                 360                 365

Ala Phe Gln Ser Ala Leu Gly His Ile Arg Ser Gly Thr Leu Asp Lys
    370                 375                 380

Phe Lys Glu Ala Phe Asp Lys Ala Leu Lys Gly Gly Glu Gly Phe Ser
385                 390                 395                 400

Val Ala Ala Asn Asn Cys Ile Gly Ser Gly Leu Val Gln Phe Asp Glu
                405                 410                 415

Ala Cys Thr Asp Val Val Ile Glu Gln Thr Asn Trp Asp Thr Ser Lys
                420                 425                 430

Val Arg Glu Lys Leu Leu Arg Asp Ile Asp Ala Tyr Val Ala Thr Val
    435                 440                 445

Arg Ala Thr Lys Ile Ser Glu Leu Thr Ser Ser Tyr Glu Glu Lys Leu
    450                 455                 460

Lys Gln Ala Leu Ser Gly Pro Val Glu Ala Leu Leu Asp Gly Ala Asn
465                 470                 475                 480

Arg Asp Thr Trp Pro Ser Ile Arg Asn Leu Leu Arg Arg Glu Thr Glu
                485                 490                 495

Ser Ala Val Ser Gly Phe Ser Ala Ala Leu Thr Gly Phe Asp Met Asp
                500                 505                 510

Glu Glu Thr Arg Gln Lys Met Ile Leu Ser Leu Glu Ala Tyr Ala Arg
    515                 520                 525

Gly Leu Val Glu Gly Lys Ala Arg Glu Glu Ala Gly Arg Val Leu Met
    530                 535                 540

Arg Met Lys Asp Arg Phe Thr Met Leu Phe Ser His Asp Ser Asp Ser
545                 550                 555                 560

Met Pro Arg Val Trp Thr Gly Lys Glu Asp Ile Arg Ala Ile Thr Lys
                565                 570                 575

Thr Ala Arg Ser Ser Ser Leu Lys Leu Leu Ser Val Met Ala Ala Ile
                580                 585                 590

Arg Leu Asp Asp Asp Thr Asp Asn Ile Glu Lys Val Leu Ala Val
                595                 600                 605

Ala Leu Val Asp Ser Ser Pro Ser Ser Asn Ala Thr Arg Ser Ile Thr
    610                 615                 620

Met Val Asp Pro Leu Ala Ser Ser Ser Trp Glu Gln Val Ser Ser Ser
625                 630                 635                 640

Lys Thr Leu Ile Thr Pro Val Gln Cys Lys Ser Leu Trp Arg Gln Phe
                645                 650                 655

Lys Thr Glu Thr Glu Tyr Ser Val Ser Gln Ala Ile Ser Ala Gln Glu
                660                 665                 670

Ala Asn Lys Arg Asn Asn Asn Trp Leu Pro Pro Trp Ala Ile Val
    675                 680                 685
```

```
Ala Leu Val Ile Leu Gly Phe Asn Glu Phe Met Thr Leu Leu Arg Asn
    690                 695                 700

Pro Leu Tyr Leu Gly Val Ile Phe Val Gly Phe Leu Leu Ile Lys Ala
705                 710                 715                 720

Leu Trp Val Gln Leu Asp Val Ser Gly Glu Phe Arg Asn Gly Ala Leu
                725                 730                 735

Pro Gly Ile Ile Ser Leu Ser Ser Lys Phe Ile Pro Thr Ile Met Asn
                740                 745                 750

Leu Met Arg Lys Leu Ala Glu Gly Gln Asn Pro Ala Ala Asn Asn
            755                 760                 765

Pro Gln Arg Thr Pro Ser Lys Asn Ser Tyr Asn Asp Gly His Ala Val
770                 775                 780

Ser Ser Ser Ala Ser Ser Asn Leu Thr Ala Leu Asp Asn Gly Thr Glu
785                 790                 795                 800

Tyr Ala Ser Pro Leu Lys Asp Glu
                805

<210> SEQ ID NO 82
<211> LENGTH: 525
<212> TYPE: PRT
<213> ORGANISM: Glycine max

<400> SEQUENCE: 82

Met Arg Val Pro Val Pro Ser Ser Pro Gln Ala Asn Pro Lys Pro Thr
1               5                   10                  15

Asn Asn Val Val Arg Thr Ile Ala Leu Pro Asn Leu Asn Asn Ser Thr
                20                  25                  30

Thr Pro Pro Thr Gly Leu Cys Tyr Glu Pro Thr Ser Val Leu Asp Leu
            35                  40                  45

Cys Arg Ser Pro Ser Pro Gly Thr Glu Lys Pro Thr Thr Asp His Ser
    50                  55                  60

Val Leu Val Thr Asn Ser Gln Asp Tyr Leu Asp Leu Glu Asp His Ala
65                  70                  75                  80

Leu His Asn Leu Asp Trp Asp Ser Ile Met Lys Asp Leu Gly Leu His
                85                  90                  95

Asp Asp Ser Ala Thr Pro Val Leu Lys Thr Phe Leu His Pro Asp Asp
            100                 105                 110

Asp Asp Asp Asp Asn Asn Asn Asn Pro Ser Cys Asp Phe Thr
        115                 120                 125

Leu Phe Asp His Ala Leu Glu Phe Thr Thr Leu Ser Asp Ile Tyr Ser
    130                 135                 140

Asn Gln Asn Phe Ala Phe Asp Phe Asn His Leu Pro His Asp Phe Asn
145                 150                 155                 160

His Leu Asn Gly Phe Asp Phe Ile Glu Glu Leu Ile Arg Ala Ala Asp
                165                 170                 175

Cys Phe Asp Thr Lys Gln Leu His Val Ala Gln Leu Ile Leu Glu Arg
            180                 185                 190

Leu Asn Gln Arg Leu Arg Ser Pro Val Gly Lys Pro Leu His Arg Ala
        195                 200                 205

Ala Phe Tyr Leu Lys Glu Ala Leu Gln Ser Leu Ser Gly Ser Asn
    210                 215                 220

Arg Thr Pro Arg Ile Ser Ser Leu Val Glu Ile Val His Ser Ile Arg
225                 230                 235                 240

Thr Phe Lys Ala Phe Ser Gly Ile Ser Pro Ile Pro Met Phe Ser Ile
                245                 250                 255
```

```
Phe Thr Thr Asn Gln Ile Val Leu Asp His Ala Ala Ser Ser Phe Met
            260                 265                 270

His Val Ile Asp Phe Asp Ile Gly Leu Gly Ile Gln Tyr Ala Ser Leu
        275                 280                 285

Met Lys Glu Ile Ala Glu Lys Ala Ala Asp Ser Pro Val Leu Arg Ile
290                 295                 300

Thr Ala Val Val Pro Glu Glu Tyr Ala Val Glu Ser Thr Leu Val Arg
305                 310                 315                 320

Asp Asn Leu Ala Gln Phe Ala Leu Asp Leu Arg Ile Arg Val Gln Val
                325                 330                 335

Glu Phe Val Pro Leu Arg Thr Phe Glu Asn Leu Ser Phe Lys Ala Val
            340                 345                 350

Lys Phe Val Asn Gly Glu Asn Thr Ala Val Leu Leu Ser Pro Ala Ile
            355                 360                 365

Phe Arg His Leu Gly Asn Ala Ala Ala Phe Leu Ala Asp Val Arg Arg
    370                 375                 380

Ile Ser Pro Ser Val Val Phe Val Asp Gly Glu Gly Trp Ala Glu
385                 390                 395                 400

Thr Ala Thr Ala Ser Ala Ala Ser Phe Arg Arg Gly Val Val Ser Ser
                405                 410                 415

Leu Glu Tyr Tyr Ser Met Met Leu Glu Ser Leu Asp Ala Ser Thr Val
                420                 425                 430

Gly Gly Gly Gly Glu Trp Val Arg Arg Ile Glu Met Met Gln Leu Arg
                435                 440                 445

Pro Lys Ile Leu Ala Ala Val Glu Ser Ala Trp Arg Arg Val Pro Pro
450                 455                 460

Trp Arg Glu Ala Phe Tyr Gly Ala Gly Met Arg Pro Val Gln Leu Ser
465                 470                 475                 480

Gln Phe Ala Asp Phe Gln Ala Glu Cys Leu Leu Ala Lys Ser Gln Ile
                485                 490                 495

Arg Gly Phe His Val Ala Lys Arg Gln Asn Glu Leu Val Leu Phe Trp
            500                 505                 510

His Asp Arg Ala Ile Val Ala Thr Ser Ala Trp Arg Cys
            515                 520                 525

<210> SEQ ID NO 83
<211> LENGTH: 516
<212> TYPE: PRT
<213> ORGANISM: Glycine max

<400> SEQUENCE: 83

Met Arg Val Pro Val Pro Ser Ser Pro Gln Ala Asn Pro Lys Pro Thr
1               5                   10                  15

Asn Asn Val Val Arg Thr Ile Ala Leu Pro Asn Leu Asn Thr Thr Thr
            20                  25                  30

Thr Thr Thr Thr Thr Ser Leu Cys Tyr Glu Pro Thr Ser Val Leu Asp
        35                  40                  45

Leu Cys Arg Ser Pro Ser Pro Ser Pro Gly Thr Glu Lys Pro Thr Asn
    50                  55                  60

Asp His Ala Val Leu Asp Leu Asp His Ala Leu His Asn Leu Asp
65                  70                  75                  80

Trp Asp Ser Ile Met Lys Asp Leu Gly Leu His Asp Asp Ser Ala Thr
                85                  90                  95

Pro Val Leu Lys Thr Phe Leu His Pro Asp Asp Asp Asn Asn Asn Pro
```

```
                100                 105                 110
Ser Cys Asp Asp Phe Thr Pro Phe Asp His Ala Leu Glu Phe Thr Ser
            115                 120                 125

Leu Ser Asp Ile Tyr Ser Asn Gln Asn Leu Ala Phe Asp Phe Asn His
130                 135                 140

Leu Pro His Asp Phe Asn His His Leu Asn Gly Phe Asp Phe Ile Glu
145                 150                 155                 160

Glu Leu Ile Arg Ala Ala Asp Cys Phe Asp Thr Lys Gln Leu His Val
                165                 170                 175

Ala Gln Val Ile Leu Glu Arg Leu Asn Gln Arg Leu Arg Ser Pro Val
            180                 185                 190

Gly Lys Pro Leu Gln Arg Ala Ala Phe Tyr Phe Lys Glu Ala Leu Gln
        195                 200                 205

Ser Leu Leu Ser Gly Ser Asn Arg Thr Pro Arg Ile Ser Ser Leu Val
    210                 215                 220

Glu Ile Val His Ser Ile Arg Thr Phe Lys Ala Phe Ser Gly Ile Ser
225                 230                 235                 240

Pro Ile Pro Met Phe Ser Ile Phe Thr Thr Asn Gln Ile Val Leu Asp
                245                 250                 255

His Ala Ala Cys Ser Phe Met His Val Ile Asp Phe Asp Ile Gly Leu
            260                 265                 270

Gly Ile Gln Tyr Ala Ser Leu Met Lys Glu Ile Ala Glu Lys Ala Ala
        275                 280                 285

Glu Ser Pro Val Leu Arg Ile Thr Ala Val Pro Glu Glu Tyr Ala
    290                 295                 300

Val Glu Ser Thr Leu Val His Asp Asn Leu Ala Gln Phe Ala Leu Glu
305                 310                 315                 320

Leu Arg Ile Arg Val Gln Val Glu Phe Val Ala Leu Arg Thr Phe Glu
                325                 330                 335

Asn Leu Ser Phe Lys Ser Val Lys Phe Val Asp Gly Glu Asn Thr Thr
            340                 345                 350

Val Leu Leu Ser Pro Ala Ile Phe Gly His Leu Gly Asn Ala Ala Ala
        355                 360                 365

Phe Leu Ala Asp Val Arg Arg Ile Ser Pro Ser Met Val Val Phe Val
    370                 375                 380

Asp Gly Glu Gly Trp Ala Glu Thr Ala Thr Ala Ser Ala Ala Ser Phe
385                 390                 395                 400

Arg Arg Gly Val Val Ser Ser Leu Glu Tyr Tyr Ser Met Met Leu Glu
                405                 410                 415

Ser Leu Asp Ala Ser Thr Val Gly Gly Gly Gly Glu Trp Val Arg Arg
            420                 425                 430

Ile Glu Met Met Gln Leu Gly Pro Lys Ile Leu Ala Ala Val Glu Ser
        435                 440                 445

Ala Trp Arg Lys Leu Pro Pro Trp Arg Glu Ala Phe Tyr Gly Ala Gly
    450                 455                 460

Met Arg Pro Val Gln Leu Ser Gln Phe Ala Asp Phe Gln Ala Glu Cys
465                 470                 475                 480

Leu Leu Ala Lys Ser Gln Ile Arg Gly Phe His Val Ala Arg Arg Gln
                485                 490                 495

Asn Glu Leu Val Leu Phe Trp His Asp Arg Ala Met Val Ala Thr Ser
            500                 505                 510

Ala Trp Arg Cys
        515
```

<210> SEQ ID NO 84
<211> LENGTH: 735
<212> TYPE: PRT
<213> ORGANISM: Glycine max

<400> SEQUENCE: 84

```
Met Met Met Met Met Lys Lys Lys Asp Ala Ala Tyr Ser Ser Ile Leu
1               5                   10                  15

Thr Leu Leu Leu Ile Ala Thr Leu Leu Ser Leu Thr Val Ser Ala Ser
            20                  25                  30

Ser Leu Ser Asp Ala Glu Ala Met Tyr Val Lys Gln Arg Gln Leu Leu
        35                  40                  45

Tyr Tyr Arg Asp Glu Phe Gly Asp Arg Gly Glu Asn Val Ile Val Asp
    50                  55                  60

Pro Ser Leu Ala Phe Glu Asn Asp Arg Leu Arg Asn Ala Tyr Ile Ala
65                  70                  75                  80

Leu Gln Ala Trp Lys Gln Ala Ile Leu Ser Asp Pro Arg Asn Gln Thr
                85                  90                  95

Ala Asp Trp Val Gly Ser Asp Val Cys Ser Tyr Thr Gly Val Tyr Cys
            100                 105                 110

Ala Pro Ala Leu Asp Ile Pro Lys Ile Arg Thr Val Ala Gly Ile Asp
        115                 120                 125

Leu Asn His Cys Asp Ile Ala Gly Tyr Leu Pro Glu Glu Leu Gly Leu
    130                 135                 140

Leu Leu Asp Leu Ala Leu Phe His Val Asn Ser Asn Arg Phe Cys Gly
145                 150                 155                 160

Thr Val Pro His Lys Phe Glu Arg Leu Lys Leu Leu Tyr Glu Leu Asp
                165                 170                 175

Leu Ser Asn Asn Arg Phe Ala Gly Asn Phe Pro Glu Val Val Leu Arg
            180                 185                 190

Leu Pro Ser Leu Lys Phe Leu Asp Leu Arg Phe Asn Glu Phe Glu Gly
        195                 200                 205

Thr Val Pro Arg Glu Leu Phe Asp Lys Asp Leu Asp Ala Ile Phe Ile
    210                 215                 220

Asn Asp Asn Arg Phe Val Phe Asp Leu Pro Asp Asn Phe Gly Asn Ser
225                 230                 235                 240

Pro Val Ser Val Ile Val Leu Ala Asn Asn Arg Phe His Gly Cys Ile
                245                 250                 255

Pro Ala Ser Leu Gly Asn Met Ser Asn Leu Asn Glu Ile Ile Leu Met
            260                 265                 270

Asn Asn Ala Phe Arg Ser Cys Leu Pro Ser Glu Ile Gly Leu Leu Lys
        275                 280                 285

Asn Leu Thr Val Phe Asp Val Ser Phe Asn Gln Leu Leu Gly Pro Ile
    290                 295                 300

Pro Asn Ala Val Gly Asn Ala Val Ser Leu Glu Gln Leu Asn Val Ala
305                 310                 315                 320

His Asn Leu Leu Ser Gly Gln Ile Pro Ala Ser Ile Cys Met Leu Pro
                325                 330                 335

His Leu Gln Asn Phe Thr Tyr Ser Phe Asn Phe Thr Gly Glu Pro
            340                 345                 350

Pro Ala Cys Leu Ala Leu Pro Ala Phe Asp Asp Arg Val Asn Cys Leu
        355                 360                 365

Pro Ala Arg Pro Leu Gln Arg Pro Pro Ala Gln Cys Lys Ser Phe Leu
```

```
                370             375             380
Ser Lys Pro Val Asp Cys Asn Ser Phe Lys Cys Lys His Phe Val Pro
385             390             395             400

Ser Pro Pro Ser Pro Ser Pro Phe Pro Ser Pro Thr Ala Pro Val Thr
                405             410             415

Pro Ser Pro Ser Pro Ser Thr Pro Ser Pro Phe Pro Ser Pro Thr Thr
                420             425             430

Pro Val Thr Pro Pro Ser Pro Ser His Ser Pro Ser Pro Ser Pro Thr
            435             440             445

Pro Ser Pro Thr Thr Pro Val Thr Pro Ser Pro Ser His Ser Pro Pro
        450             455             460

Ser Pro Ala Thr Pro Ser Pro Phe Pro Ser Pro Thr Thr Pro Val Thr
465             470             475             480

Pro Ser Pro Ser His Ser Pro Pro Ser Pro Ala Thr Pro Ser Pro Phe
                485             490             495

Pro Ser Pro Thr Thr Pro Val Thr Pro Ser Pro Ser His Ser Pro Pro
            500             505             510

Ser Pro Ala Thr Pro Thr Thr Pro Val Thr Pro Ser Pro Ser His Ser
        515             520             525

Pro Pro Ser Pro Ala Thr Pro Ser Pro Phe Pro Ser Pro Thr Thr Pro
    530             535             540

Val Thr Pro Ser Pro Ser His Ser Pro Pro Ser Pro Ala Thr Pro Ser
545             550             555             560

Pro Phe Pro Ser Pro Thr Thr Pro Val Thr Pro Ser Pro Pro Ser Pro
                565             570             575

Ser Thr Pro Ser Pro Phe Pro Ser Pro Thr Thr Pro Val Thr Pro Ser
            580             585             590

Pro Val His Ser Pro Pro Ser Pro Val Tyr Leu Pro Pro Pro His Ser
        595             600             605

Ser Pro Thr Pro Pro Ala His Asn Tyr Gly Ser Pro Pro Pro His His
    610             615             620

Ser Pro Ala Gln Pro Val Tyr Pro Tyr Leu Ser Pro Pro Pro Pro Pro
625             630             635             640

Ser Val His Ser Ser Pro Pro Pro Pro Pro Pro Pro Cys Ile Glu
                645             650             655

Leu Pro Pro Pro Pro Gln Ser Thr Pro Ser Pro Thr Pro Tyr Leu
            660             665             670

Pro Pro Pro Ser Pro Ser Pro Pro Pro Pro Pro Pro Val Tyr His
        675             680             685

Ser Pro Pro Ala Ser Pro Pro Pro Cys Glu Thr Pro Pro Ser Val
    690             695             700

Ser Pro Pro Pro Pro Ala Pro Val Tyr Glu Gly Pro Leu Pro Pro
705             710             715             720

Ile Val Gly Leu Pro Tyr Ala Ser Pro Pro Pro Pro Phe Tyr
            725             730             735
```